US009399670B2

(12) United States Patent
Krell et al.

(10) Patent No.: US 9,399,670 B2
(45) Date of Patent: Jul. 26, 2016

(54) METHOD FOR OBTAINING IMMUNOGLOBULIN ENCODING NUCLEIC ACID

(75) Inventors: Hans-Willi Krell, Penzberg (DE); Alexander Lifke, Penzberg (DE); Valeria Lifke, Penzberg (DE); Kairat Madin, Penzberg (DE); Christian Weilke, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 339 days.

(21) Appl. No.: 13/202,446

(22) PCT Filed: Feb. 18, 2010

(86) PCT No.: PCT/EP2010/001008
§ 371 (c)(1),
(2), (4) Date: Aug. 19, 2011

(87) PCT Pub. No.: WO2010/094475
PCT Pub. Date: Aug. 26, 2010

(65) Prior Publication Data
US 2011/0306094 A1 Dec. 15, 2011

(30) Foreign Application Priority Data
Feb. 20, 2009 (EP) ..................... 09002396

(51) Int. Cl.
C12Q 1/68 (2006.01)
C07K 16/00 (2006.01)

(52) U.S. Cl.
CPC .............. *C07K 16/00* (2013.01); *C12Q 1/6858* (2013.01); *C12Q 1/6881* (2013.01); *C07K 2317/21* (2013.01); *C07K 2317/55* (2013.01); *C12Q 2600/16* (2013.01)

(58) Field of Classification Search
None
See application file for complete search history.

(56) References Cited

U.S. PATENT DOCUMENTS

| 5,202,238 A | 4/1993 | Fell et al. |
| 5,204,244 A | 4/1993 | Fell et al. |
| 5,478,730 A | 12/1995 | Alakhov et al. |
| 5,571,690 A | 11/1996 | Hecht |

FOREIGN PATENT DOCUMENTS

| EP | 0307434 B1 | 3/1989 |
| EP | 0932664 B1 | 9/2001 |
| JP | 2008/295415 | 6/2004 |
| WO | 98/31827 | 7/1998 |
| WO | 99/50436 | 10/1999 |
| WO | 00/55353 | 9/2000 |
| WO | 00/58493 | 10/2000 |
| WO | 02/13862 A2 | 2/2002 |
| WO | 2004/094475 A2 | 11/2004 |
| WO | 2004/094475 A3 | 11/2004 |
| WO | 2005/040396 | 5/2005 |
| WO | 2005/116645 A2 | 12/2005 |
| WO | 2008/104184 A2 | 9/2008 |
| WO | 2010/094475 | 8/2010 |
| WO | 2011/086006 | 7/2011 |

OTHER PUBLICATIONS

MacFerrin et al. Proceedings of the National Academy of Sciences, USA (1990) 87: 1937-1941.*
Kim et al. Methods in Molecular Medicine (2007) 2: 25-37.*
Roux, K.H. Optimization and troubleshooting in PCR. Genome Research 4: S185-S194 (1995).*
Ausubel et al. Current Protocols of Molecular Biology (Table of Contents),John Wiley & Sons, Inc., vol. 3:4 (2007).
Bertrand et al., "Ig D(H) gene segment transcription and rearrangement before surface expression of the pan-B-cell marker CD19 in normal human bone marrow" Blood 90(2):736-44 (Jul. 15, 1977).
Bird, R. E. et al., Science 242:423-426 (1988).
Boerner et al., "Production of antigen-specific human monoclonal antibodies from in vitro-primed human splenocytes" J Immunol. 147(1):86-95 (Jul. 1, 1991).
Brauninger et al., "Molecular analysis of single B cells from T-cell-rich B-cell lymphoma shows the derivation of the tumor cells from mutating germinal center B cells and exemplifies means by which immunoglobulin genes are modified in germinal center B cells" Blood 93(3):2679-87 (Apr. 1999).
Cole et al. Monoclonal Antibodies and Cander Therapy "The EBV-hybridoma technique and its application to human lung cancer" New York:Alan R. Liss, Inc.,:77-96 ( 1985).
Coronella et al., "Apliification of IgG VH and VL (Fab) from single human plasma cells and B cells" Nucleic Acids Res. 28(20):E85 ( 2000).
De Wildt et al., "Analysis of Heavy and Light chain pairings indicates that receptor editing shapes the human antibody repertoire" J Mol Biol. 285:895-901 ( 1999).
European Search Reprot for EP 09 00 2396, Jul. 16, 2009.
Farner et al., "Molecular mechanisms and selection influence the generation of the human V lambda J lambda repertoire" J Immunol. 4(162:2137-45 ( 1999).
Foster et al., "Molecular mechanisms and selective influences that shape the kappa gene repertoire of IgM+ B cells" J Clin Invest. 99(7):1614-1627 ( 1997).
Fresno et al., "Initiation of the polypeptide chain by reticulocyte cell-free systems. Survey of different inhibitors of translation" Eur J Biochem. 68(2):355-64 ( 1976).
Frippiat et al., "Organization of the human immunoglobulin lambda light-chain locus on chromosome 22q11.2" Hum Mol Genet. 5(6):983-97 ( 1995).

(Continued)

*Primary Examiner* — Angela M Bertagna

(57) ABSTRACT

The current invention is directed to a method for obtaining a nucleic acid encoding an immunoglobulin variable domain from a single cell comprising the following steps: —performing a first polymerase chain reaction with three to six 5'-primer and one 3'-primer, performing with the product of the first polymerase chain reaction a second polymerase chain reaction with thirteen to sixteen 5'-primer and one 3'-primer, whereby the distance of the binding locations of the primer employed in the second polymerase chain reaction is reduced compared to the first polymerase chain reaction.

8 Claims, 18 Drawing Sheets

(56) References Cited

OTHER PUBLICATIONS

Hood et al. Immunology 2nd edition,Benjamin NY,:2 pages ( 1984).
Hoogenboom and Winter, "By-passing immunisation human antibodies from synthetic repertoires of germline $V_H$ gene segments rearranged in vitro" J. Mol. Biol. 227:381-388 ( 1992).
Hunkapiller et al., "The growing immunoglobulien gene superfamily" Nature 323:15-6 ( 1986).
Huston et al., "Protein engineering of antibody biding sites: recovery of specific activity in an anti-dgoxin single-chain Fv analogue produced in *Escherichia coli*" Proc Natl Acad Sci U S A. 85(16):5879-83 ( 1988).
Jiang et al., "A novel strategy for generation of monoclonal antibodies fron single B cells using rt-PCR technique and in vitro expression" Biotechnol Prog. 22(4):979-88 ( 2006)
Johnson et al. et al., "Kabat Database and its applications: 30 years after the first variability plot" Nucleic Acids Res 28(1):214-218 ( 2000).
Lefranc, "Nomenclature of the human immunoglobulin kappa (IGK) genes" Exp Clin Immunogenet 18(3):161-74 ( 2001).
Lefranc, "Nomenclature of the human immunoglobulin lambda (IGL) genes" Exp Clin Immunogenet 18(4):):242-54 ( 2001).
Lonberg, "Human antibodies from transgenic animals" Nat Biotechnol. 23(9):1117-25 ( 2005).
Lund et al., "Oligosaccharide-protein interactions in IgG can modulate recognition by Fc gamma receptors"FASEB J. 9(2):115-9 ( 1995).
Marks et al., "By-passing immuniztion, Human antibodies from V-gene libraries displayed on phage" J. Mol. Biol. 222:581-597 ( 1991).
Matsuda et al., "The complete nucleotide sequence of the human immunoglobulin heavy chain variable region locus" J Exp Med. 188(11):2151-62 ( 1998).
Meijer et al., "Isolation of human antibody repertoires with preservation of the natural heavy and light chain paring" J Mol Biol. 358(3):764-72 ( 2006).
Morgan et al. et al., "The N-terminal end of the $C_H2$ Domain of Chimeric Human IgG1 anti-HLA-DR is Necessry for C1q, FcγRI and FcγRIII Binding" Immunology 86:319-324 ( 1995).
Morrison et al., "Chimeric human antibody molecules: mouse antigen-binding domains with human constant region domains" Proc. Natl. Acad. Sci. USA 81:6851-6855 (Nov. 1984).
Neuberger et al. et al., "A hapten-specific chimaeric IgE antibody with human physiological effector function" Nature 314:268-270 (Mar. 21, 1985).
PCT ISR for PCT/EP2010/001008, Apr. 20, 2010.
Pelham & Jackson, "An Efficient mRNA-Dependent Translation System for Reticulocyte Lysates" Eur J Biochem 67:247-256 ( 1976).
Pratt et al. Transcription and Translation: A Practical Approach Hames and Higgins edition,IRL Press,:179-209 ( 1984).
Pratt et al., "Identification of gene products programmed by restriction endonuclease DNA fragments using an *E. coli* in vitro system" Nucleic Acids Res. 9(18):4459-74 ( 1981).
Riechmann et al., "Reshaping human antibodies for therapy" NATURE 332(6162):323-327 (Mar. 24, 2988).
Rohatgi et al., "Systematic design and testing of nested (RT-)PCR primers for specific amplification of mouse rearranged/expressed immunoglobulin variabble region genes from small number of B cells" J Immunol Methods 339(2):205-19 (Dec. 2008).
Sambrook et al. Molecular Cloning 2nd edition,Cold Spring Harbor Laboratory Press, ( 1989), 2 pages.
Schable et al., "The variable genes of the human immunoglobulin kappa locus" Biol Chem Hoppe Seyler 374(11):1001-22 ( 1993).
Shields et al., "High resolution mapping of the binding site on human IgG1 for FcγRI, FcγRII, FcγRIII, and FcRn and design of IgG1 variants with improved binding to the FcγR" J Biol. Chem. 276(9):6591-6604 (Mar. 2, 2001).
Skup et al., "Highly efficient translation of messenger RNA in cell-free extracts prepared form L-cells" Nucleic Acids Res. 4(10):3581-7 ( 1977).
Spirin et al., "Continuous Cell-Free Translation System Capable of Producing Polypeptides in High Yield" Science 243(4882):1162-1164 (Nov. 25, 1988).
Tiller et al., "Efficient generation of monoclonal antibodies from single human B cells by single cell RT-PCR and expression vector cloning" J Immunol Methods 329(1-2):112-24 (Jan. 2008).
Vijayalakshmi, "Antibody Purification Methods" Appl Biochem Biotech 75:93-102 ( 1998).
Wang et al., "Human immunoglobulin variable region gene analysis by single cell RT-PCR" J Immunol Methods 244(1-2):217-25 (Oct. 2000).
Winkler t al., "Transcription termination at the tryptophan operon attenuator is decreased in vitro by an oligomer complementary to a segment of the leader transcript" Proc Natl Acad Sci U S A. 79(7):2181-5 (Apr. 1982).
Winter et al., "Antibody-Based Therapy—Humanized Antibodies" Immunology Today 14(6):243-246 ( 1993).
Zubay, "In vitro synthesis of protein in microbial systems" Ann Rev Genet 7:267-287 ( 1973).
Boddicker et al., "Real-Time Reverse Transcription-PCR Assay for Detection of Mumps Virus RNA in Clinical Specimens" Journal of Clinical Microbiology 45(9):2902-2908 (Sep. 2007).
Hindiyeh et al., "Evaluation of a Multiplex Real-Time Reverse Transcriptase PCR Assay for Detection and Differentiation of Influenza Viruses A and B during the 2001-2002 Influenza Season in Israel"πJournal of Clinical Microbiology 43(2):589-595 (Feb. 2005).
Holland et. et al., "Detection of specific polymerase chain reaction product by utilizing the 5'—3' exonuclease activity of Thermus acquaticus DNA polymerase" P Natl Acad Sci USA 88(16):7276-7280 (Aug. 15, 1991).

\* cited by examiner (A)

(B)

METHOD FOR OBTAINING IMMUNOGLOBULIN ENCODING NUCLEIC ACID

CROSS REFERENCE TO RELATED APPLICATIONS

This application is a 35 U.S.C. 371 national stage of PCT/EP2010/001008, filed Feb. 18, 2010, which in turn claims priority to EP 09002396.1, filed Feb. 20, 2009, the contents of both which are hereby incorporated by reference in their entireties.

The present invention relates to a method and means for obtaining immunoglobulin encoding nucleic acid from a single immunoglobulin producing cell with a multiplexed polymerase chain reaction (PCR), and also to a method for producing an immunoglobulin whereby the immunoglobulin encoding nucleic acid is obtained from a single immunoglobulin producing cell in combination with in vitro translation. Also encompassed by the current invention is a method for characterization of recombinantly produced human Fab-fragments.

BACKGROUND OF THE INVENTION

Since the establishment of hybridoma technology (Cole, S. P. C., et al., Monoclonal Antibodies and Cancer Therapy, Alan R. Liss, p. 77 (1985); and Boerner, P., et al., J. Immunol. 147 (1991) 86-95), monoclonal immunoglobulins have emerged to play a pivotal role in scientific research, human healthcare and diagnostics. Consequently, the generation of monoclonal, especially therapeutic, immunoglobulins is a field undergoing intensive research. In this respect, the hybridoma technology and phage display technology (Hoogenboom, H. R., and Winter, G., J. Mol. Biol. 227 (1992) 381-388; Marks, J. D., et al., J. Mol. Biol. 222 (1991) 581-597) are, amongst others, two commonly used technologies for the generation of monoclonal immunoglobulins. In hybridoma technology obtaining of stable clones is a hurdle, thus, diminishing diversity of the antibodies, as only a limited number of B-cells are successfully fused, propagated and thereafter characterized. Similarly, a drawback of phage or yeast display-based combinatorial library approaches is the random pairing of the immunoglobulin heavy and light chains. The dissociation of the original heavy and light chain pairing, and non-cognate pairing, necessitate the screening of a large number of immunoglobulin producing cells in order to identify heavy and light chain pairs of high affinity. In addition, such non-cognate pairs may display unwanted cross-reactivity to human antigens. Finally, the genetic diversity of target-specific immunoglobulins identified by selection and screening of combinatorial libraries is commonly limited due to inherent selection biases.

Generation of immunoglobulins from immunoglobulin producing cell can be performed according to methods known in the art. Such methods are e.g. hybridoma technique. A different method is based on the identification of the nucleic acid sequence of the immunoglobulin. Usually it is sufficient to identify the sequence of the variable regions or even only the CDR regions or only the CDR3 region. For example, the mRNA is isolated from a pool of immunoglobulin producing cells and is used for the construction of a cDNA-library encoding the CDR regions of the immunoglobulin. The cDNA-library is then transfected into a suitable host cell, such as NS0 or CHO, and screened for specific immunoglobulin production.

WO 2008/104184 reports a method for cloning cognate antibodies. The efficient generation of monoclonal antibodies from single human B cells is reported by Tiller et al. (Tiller, T., et al., J. Immunol. Meth. 329 (2007) 112-124). Braeuninger et al. (Braeuninger, A., et al., Blood 93 (1999) 2679-2687) report the molecular analysis of single B cells from T-cell-rich B-cell lymphoma. Systematic design and testing of nested (RT-) PCR primer is reported by Rohatgi et al. (Rohatgi, S., et al, J. Immunol. Meth. 339 (2008) 205-219). In WO 02/13862 a method and composition for altering a B-cell mediated pathology are reported. Haurum et al. (Meijer, P. J. and Haurum, J. S., J. Mol. Biol. 358 (2006) 764-772) report a one-step RT-multiplex overlap extension PCR. Stollar et al. and Junghans et al. report the sequence analysis by single cell PCR reaction (Wang, X. and Stollar, B. D., J. Immunol. Meth. 244 (2000) 217-225; Coronella, J. A. and Junghans, R. P., Nucl. Acids Res. 28 (2000) E85). Jiang, X. and Nakano, H., et al. (Biotechnol. Prog. 22 (2006) 979-988) report the construction of a linear expression element for in vitro transcription and translation.

SUMMARY OF THE INVENTION

The current invention is directed in specific embodiments of an aspect to a method for providing a human monoclonal antibody comprising the in vitro translation of a nucleic acid encoding human immunoglobulin G fragments whereby the nucleic acid is obtained by specific amplification of cDNA fragments obtained from the mRNA of a single immunoglobulin producing human B-cell, plasmablast or plasma cell or a B-cell of an animal comprising a human immunoglobulin locus.

With this method it is possible to characterize each of a number of provided B-cells with respect to the antigen binding characteristics of the produced immunoglobulin. Thus, no loss of immunoglobulin diversity occurs. As the analyzed B-cells are mature B-cells obtained after the in vivo maturation process it is very unlikely that their produced immunoglobulins show cross-reactivity with other antigens.

The invention comprises a method for the multiplex semi-nested PCR and multiplex one tube RT-GSP-PCR (RT-Gene Specific Primer-PCR) for the amplification of cognate IgG HC and IgG LC chains (human IgG isotype) from a single B-cell or plasmablast or plasma cell. The Fab PCR product is subsequently transcribed to mRNA and translated in vitro in E. coli lysate. The expression was examined using ELISA and Western blot.

The current invention comprises as first aspect a method for obtaining a nucleic acid encoding an immunoglobulin variable domain from a single cell comprising the following steps:
  obtaining a first nucleic acid composition by performing a first polymerase chain reaction with three to six 5'-primer and one 3'-primer,
  obtaining a nucleic acid encoding an immunoglobulin variable domain by performing with the composition obtained in the first polymerase chain reaction a second polymerase chain reaction with thirteen to sixteen 5'-primer and one 3'-primer,
  whereby, when bound to the nucleic acid to be amplified, the distance of the binding locations of the 5'-primer to the binding location of the 3'-primer employed in the second polymerase chain reaction is reduced compared to that of the first polymerase chain reaction.

A second aspect of the current invention is a method for obtaining a nucleic acid encoding an immunoglobulin variable domain from a single cell comprising the following steps:
  obtaining a nucleic acid composition by performing a first polymerase chain reaction with four to six 5'-primer and one 3'-primer,
  obtaining a nucleic acid encoding an immunoglobulin variable domain by performing with the composition obtained in the first polymerase chain reaction a second polymerase chain reaction with thirteen to fifteen 5'-primer and one 3'-primer,
  whereby in the second polymerase chain reaction either the 5'-primer are the same as that in the first polymerase chain reaction and the 3'-primer is changed or the 3'-primer is the same as in the first polymerase chain reaction and at least one 5'-primer is changed,
  whereby, when bound to the nucleic acid to be amplified, the number of nucleotides between the 5'-end of each of the 5'-primer and the 3'-end of the 3'-primer in the second polymerase chain reaction is reduced compared to the number of nucleotides between the 5'-end of each of the 5'-primer and the 3'-end of the 3'-primer in the first polymerase chain reaction.

A further aspect of the current invention is a method for obtaining a nucleic acid encoding an immunoglobulin variable domain from a single cell by a multiplex one tube RT-GSP-PCR comprising the following step:
  performing a reverse transcription and polymerase chain reaction in one step with one 5'-primer and one 3'-primer.

In one embodiment the methods according to the invention are characterized in that the 5'-primer employed in the first polymerase chain reaction bind in the coding region for the leader peptide of the immunoglobulin. In another embodiment the methods according to the invention are characterized in that the 5'-primer employed in the second polymerase chain reaction or the 5'-primer employed in a multiplex one tube RT-GSP-PCR bind in the coding region of the first framework region of the immunoglobulin. In a further embodiment the methods according to the invention are characterized in that the primer employed in the second polymerase chain reaction provide for overhangs encoding the translational start codon ATG for 5'-primer and/or the translational stop codon TTA for 3'-primer. In still a further embodiment the methods according to the invention are characterized in comprising the additional step of:
  providing a single cell and obtaining the mRNA of this cell.

In a further embodiment the methods according to the previous embodiment are characterized in comprising the following second step:
  obtaining cDNA from the provided mRNA with a reverse transcriptase polymerase chain reaction (RT-PCR).

In another embodiment the methods according to the invention are characterized in that six 5'-primer and one 3'-primer are employed in the first polymerase chain reaction. In still a further embodiment the methods according to the invention are characterized in that four 5'-primer and one 3'-primer are employed in the second polymerase chain reaction. In a further embodiment of the current invention the methods are characterized in that
  a) for obtaining a nucleic acid encoding an immunoglobulin heavy chain variable domain the primer in the first polymerase chain reaction comprise the nucleic acids of SEQ ID NO: 05 and/or 06, 07 and/or 08, 09, 10 and/or 11, 12, 13, and 104 and/or 105 and/or 106, and the primer in the second polymerase chain reaction comprise the nucleic acids of SEQ ID NO: 128, 129, 130, 131, 132, 133, 134, 135, 136, 137, 138, 139, 140, 141, and 104 and/or 105 and/or 106, and/or 142, and/or 143,
  b) for obtaining a nucleic acid encoding an immunoglobulin kappa light chain variable domain the primer in the first polymerase chain reaction comprise the nucleic acids of SEQ ID NO: 16, 17, 18, 19, and 115, and the primer in the second polymerase chain reaction comprise the nucleic acids of SEQ ID NO: 53 and/or 54, 55 and/or 56, 57 and/or 58, 59, 60, 61 and/or 62, 63 and/or 64, 65, 66, 67, 68, 69, 70, and/or 115, and/or 144, and/or 145,
  c) for obtaining a nucleic acid encoding an immunoglobulin lambda light chain variable domain the primer in the first polymerase chain reaction comprise the nucleic acids of SEQ ID NO: 21, 22, 23 and/or 24 and/or 25 and/or 26, and 120 and/or 121 and/or 122 and/or 123 and/or 124 and/or 125, and the primer in the second polymerase chain reaction comprise the nucleic acids of SEQ ID NO: 72, 73 and/or 74, 75, 76, 77 and/or 78, 79, 80, 81, 82 and/or 83, 84 and/or 85, 86, 87 and/or 88, 89, 90 and/or 91, 92, and 120 and/or 121 and/or 122 and/or 123 and/or 124 and/or 125.

In one embodiment of the methods according to the invention the immunoglobulin variable domain is an immunoglobulin heavy chain variable domain or an immunoglobulin kappa light chain variable domain or an immunoglobulin lambda light chain variable domain.

A further aspect of the current invention is a method for producing an immunoglobulin Fab-fragment comprising the following steps:
  providing a single immunoglobulin producing cell,
  obtaining from the cell the nucleic acid encoding the immunoglobulin light and heavy chain variable domains, optionally also encoding a part of the light chain constant domain and a part of the heavy chain $C_H 1$ domain,
  generating a linear expression matrix comprising the obtained nucleic acid,
  translating in vitro the nucleic acid and thereby producing the immunoglobulin Fab fragment.

Another aspect of the current invention is a method for producing an immunoglobulin comprising the following steps:
  providing a single immunoglobulin producing cell,
  obtaining from the cell the nucleic acid encoding the immunoglobulin light and heavy chain variable domains,
  linking the nucleic acid encoding the light chain variable domain with a nucleic acid encoding an immunoglobulin light chain constant domain in operable form, and linking the nucleic acid encoding the heavy chain variable domain with a nucleic acid encoding an immunoglobulin heavy chain constant region in operable form,
  transfecting a eukaryotic or a prokaryotic cell with the nucleic acids obtained in the previous step,
  cultivating the transfected cell, in one embodiment under conditions suitable for the expression of the immunoglobulin,
  recovering the immunoglobulin from the cell or the cultivation medium and thereby producing an immunoglobulin.

In one embodiment of all methods according to the invention is the immunoglobulin an immunoglobulin of class G (IgG). In one embodiment of the methods for producing an immunoglobulin Fab fragment or an immunoglobulin is the obtaining of the nucleic acid by a method according to an aspect of the current invention.

DESCRIPTION OF THE INVENTION

One aspect of the current invention is a method for obtaining a nucleic acid encoding an immunoglobulin variable domain from a single cell comprising the following steps:
performing a first polymerase chain reaction with three to six 5'-primer and one 3'-primer,
performing with the product of the first polymerase chain reaction a second polymerase chain reaction with thirteen to sixteen 5'-primer and one 3'-primer, thereby obtaining a nucleic acid encoding an immunoglobulin variable domain,
whereby the distance of the binding locations of the primer employed in the second polymerase chain reaction is reduced compared to the first polymerase chain reaction.

By employing magnetic micro-beads coated with the human pan B-cell marker, CD19 (see e.g. Bertrand, F. E., III, et al., Blood 90 (1997) 736-744), B-cells were isolated from peripheral blood. With the limited dilution approach, single cells were placed in a 96 well microtiter plate. The mRNA of these cells was extracted.

It has been found that by performing the IgG-specific PCR amplification according to the current invention for obtaining nucleic acid encoding an immunoglobulin variable domain from a single cell in a thereafter following production of the respective immunoglobulin or Fab-fragment in one embodiment OD-values in the range of from 0.5 to 2.0 were obtained, and concomitantly, e.g., Fab-fragment yields of from 180 to 310 ng/ml were obtained.

With the methods according to the current invention a multiplex polymerase chain reaction is used for the amplification of heavy and light chain variable domains simultaneously in the same polymerase chain reaction. In contrast to the amplification of the heavy chain variable domain and the light chain variable domain in separate reactions the current approach provides for an increased sensitivity and an increased amount of amplified sequences. The use of gene-specific primer in both, i.e. all, polymerase chain reactions enhances the specificity and accuracy of the methods.

More complex gene structure in the case of human IgG requires a different strategy for the primer design, placement and polymerase chain reaction for the sensitivity and accuracy required.

Thus, herein is employed a multiplex polymerase chain reaction either without or with the linkage of the heavy and light chain regions that are amplified. For the in vitro translation of the obtained nucleic acids it is beneficial that the encoded domains comprise cysteine residues suitable for the formation of interchain disulfide bonds.

Methods and techniques known to a person skilled in the art, which are useful for carrying out the current invention, are described e.g. in Ausubel, F. M., ed., Current Protocols in Molecular Biology, Volumes I to III (1997), Wiley and Sons; Sambrook, J., et al., Molecular Cloning: A Laboratory Manual, Second Edition, Cold Spring Harbor Laboratory Press, Cold Spring Harbor, N.Y. (1989), Morrison, S. L., et al., Proc. Natl. Acad. Sci. USA 81 (1984) 6851-6855; U.S. Pat. No. 5,202,238 and U.S. Pat. No. 5,204,244.

The term "immunoglobulin" denotes a protein consisting of one or more polypeptide(s) substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)$_2$ as well as single chains (scFv) or diabodies (e.g. Huston, J. S., et al., Proc. Natl. Acad. Sci. USA 85 (1988) 5879-5883; Bird, R. E., et al., Science 242 (1988) 423-426; Hood, L. E. et al., Immunology, Benjamin N.Y., 2nd edition (1984); Hunkapiller, T. and Hood, L., Nature 323 (1986) 15-16).

An immunoglobulin in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of an immunoglobulin's light or heavy chain in turn comprises different segments, i.e. four framework regions (FR) and three hypervariable regions (CDR).

Genetic engineering of immunoglobulins is e.g. described in Morrison, S. L., et al., Proc. Natl. Acad. Sci. USA 81 (1984) 6851-6855; U.S. Pat. No. 5,202,238 and U.S. Pat. No. 5,204, 244; Riechmann, L., et al., Nature 332 (1988) 323-327; Neuberger, M. S., et al., Nature 314 (1985) 268-270; Lonberg, N., Nat. Biotechnol. 23 (2005) 1117-1125.

The term "chimeric immunoglobulin" denotes an immunoglobulin, preferably a monoclonal immunoglobulin, comprising a variable domain, i.e. binding region, from a first non-human species and at least a portion of a constant region derived from a second different source or species. Chimeric immunoglobulins are generally prepared by recombinant DNA techniques. In one embodiment chimeric immunoglobulins comprise a mouse, rat, hamster, rabbit, or sheep variable domain and a human constant region. In one embodiment the human heavy chain constant region is a human IgG constant region. In another embodiment the human light chain constant region is a kappa chain or a lambda chain.

Other forms of chimeric immunoglobulins encompassed by the present invention are those in which the class or subclass of the non-human immunoglobulin from which the variable domain is derived has been changed. Such immunoglobulins are also referred to as "class-switched immunoglobulins". Forms of "class-switched immunoglobulins" encompassed by the present invention are also those in which the constant region has differences from the wild-type constant region sequence that result in an immunoglobulin with different properties, e.g. in regard to C1q binding and/or Fc receptor (FcR) binding. The "Fc part" of an immunoglobulin is not directly involved in binding to the antigen, but exhibit various effector functions. Depending on the amino acid sequence of the constant region of the heavy chain, immunoglobulins are divided in the classes: IgA, IgD, IgE, IgG, and IgM. Some of these classes are further divided into subclasses, i.e. IgG in IgG1, IgG2, IgG3, and IgG4, or IgA in IgA1 and IgA2. According to the immunoglobulin class to which an immunoglobulin belongs the heavy chain constant regions of immunoglobulins are called α (IgA), δ (IgD), ε (IgE), γ (IgG), and μ (IgM), respectively. The immunoglobulins according to the invention belong in one embodiment to the IgG class. An "Fc part of an immunoglobulin" is a term well known to the skilled artisan and defined on basis of the papain cleavage of immunoglobulins. In one embodiment of the invention the immunoglobulin contains as Fc part a human Fc part or an Fc part derived from human origin. In a further embodiment of the invention is the Fc part either an Fc part of a human immunoglobulin of the subclass IgG4 or IgG1 or is an Fc part of a human antibody of the subclass IgG1, IgG2, or IgG3, which is modified in such a way that no Fcγ receptor (e.g. FcγRIIIa) binding and/or no C1q binding as defined below can be detected. In one embodiment the Fc part is a human Fc part, in another embodiment a human IgG4 or IgG1 subclass Fc part or a mutated Fc part from human IgG1 subclass. In a further embodiment the Fc part is from human IgG1 subclass with mutations L234A and L235A. While IgG4 shows reduced Fcγ receptor (FcγRIIIa) binding, immunoglobulins of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, or/and His435 are residues which, if altered, provide also reduced Fcγ receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434). In one embodiment the immunoglobulin is in regard to Fcγ receptor binding of IgG4 or IgG1 subclass or of IgG1 or IgG2 subclass, with a mutation in L234, L235, and/or D265, and/or contains the PVA236 mutation. In another embodiment the mutations are S228P, L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA). In a further embodiment the mutations are S228P of IgG4, and L234A and L235A of IgG1. The Fc part of an immunoglobulin is directly involved in ADCC (antibody-dependent cell-mediated cytotoxicity) and CDC (complement-dependent cytotoxicity). An immunoglobulin which does not bind Fcγ receptor and/or complement factor C1q does not elicit antibody-dependent cellular cytotoxicity (ADCC) and/or complement dependent cytotoxicity (CDC). In one embodiment the heavy chain constant region has an amino acid sequences of SEQ ID NO: 01, or SEQ ID NO: 02, or SEQ ID NO: 01 with mutations L234A and L235A, or SEQ ID NO: 02 with mutation S228P, and the light chain constant region has an amino acid sequence of SEQ ID NO: 03 or SEQ ID NO: 04.

"Humanized" or "CDR-grafted" forms of non-human (e.g. rodent or rabbit) immunoglobulins are immunoglobulins that contain partial sequences derived from a non-human immunoglobulin and partial sequences derived from a human immunoglobulin. For the most part, humanized immunoglobulins are derived from a human immunoglobulin (recipient or acceptor immunoglobulin), in which residues from a hypervariable region are replaced by residues from a hypervariable region of a non-human species (donor immunoglobulin), such as mouse, rat, hamster, rabbit, or non-human primate, having the desired specificity and affinity (see e.g. Morrison, S. L., et al., Proc. Natl. Acad. Sci. USA 81 (1984) 6851-6855; U.S. Pat. No. 5,202,238; U.S. Pat. No. 5,204,244). In some instances, framework region (FR) residues of the acceptor immunoglobulin are replaced by corresponding non-human residues. Furthermore, humanized immunoglobulins may comprise further modifications, e.g. amino acid residues that are not found in the acceptor immunoglobulin or in the donor immunoglobulin. Such modifications result in variants of such recipient or donor immunoglobulin, which are homologous but not identical to the corresponding parent sequence.

Methods for humanizing non-human immunoglobulin have been described in the art. Generally, a humanized immunoglobulin comprises one or more amino acid residues introduced into it from a source which is non-human. These non-human amino acid residues are often referred to as "import" residues, which are typically taken from an "import" variable domain. Humanization can be essentially performed following the method of Winter and co-workers by substituting hypervariable region sequences for the corresponding sequences of a non-human immunoglobulin (see e.g. Winter, G. and Harris, W. J., Immunol. Today 14 (1993) 243-246).

The term "human immunoglobulin" as used herein, denotes an immunoglobulin having variable and constant regions (domains) derived from human germ line immunoglobulin sequences and having high sequence similarity or identity with these germ line sequences. The variable heavy chain region is in one embodiment derived from germline sequence DP-50 (GenBank L06618) and the variable light chain region is derived from germline sequence L6 (GenBank X01668) or the variable heavy chain region is derived DP-61 (GenBank M99682) and the variable light chain region is derived from germline sequence L15 (GenBank K01323). The constant regions of the antibody are constant regions of human IgG1 or IgG4 type or a variant thereof. Such regions can be allotypic and are described by, e.g., Johnson, G. and Wu, T. T., Nucleic Acids Res. 28 (2000) 214-218, and the databases referenced therein.

The term "recombinant immunoglobulin" as used herein denotes an immunoglobulin that is prepared, expressed, or created by recombinant means, such as immunoglobulins isolated from host cells, such as E. coli, NS0, BHK, or CHO cells, or from an animal (e.g. a mouse or rabbit) that is transgenic for human immunoglobulin genes. "Recombinant human immunoglobulins" according to the invention have in one embodiment variable and constant regions in a rearranged form. The recombinant human immunoglobulins according to the invention have been subjected to in vivo somatic hypermutation. Thus, the amino acid sequences of the VH and VL regions of the recombinant human immunoglobulins are sequences that can be assigned to defined human germ line VH and VL sequences, but may not naturally exist within the human antibody germ line repertoire in vivo.

The term "monoclonal immunoglobulin" as used herein refers to an immunoglobulin obtained from a population of substantially homogeneous immunoglobulins, i.e. the individual immunoglobulins of the population are identical except for naturally occurring mutations that may be present in minor amounts. Monoclonal immunoglobulins are highly specific, being directed against a single antigenic site. Furthermore, in contrast to polyclonal immunoglobulin preparations, which include different immunoglobulins directed against different antigenic sites (determinants or epitopes), each monoclonal immunoglobulin is directed against a single antigenic site. In addition to their specificity, the monoclonal immunoglobulins are advantageous in that they may be synthesized uncontaminated by other immunoglobulins. The modifier "monoclonal" indicates the character of the immunoglobulin as being obtained from a substantially homogeneous population of immunoglobulins and is not to be construed as requiring production of the immunoglobulin by any particular method.

Immunoglobulins having "conservative sequence modifications", which are amino acid sequence modifications which do not affect or alter the characteristics of the immunoglobulin, are denoted as "variant immunoglobulins". Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), non-polar side chains (e.g. alanine, valine, leucine, isoleucine, proline, phenylalanine, methionine), beta-branched side chains (e.g. threonine, valine, isoleucine), and aromatic side chains (e.g. tyrosine, phenylalanine, tryptophan, histidine). Thus, a predicted amino acid residue not essential for antigen binding in an immunoglobulin can be replaced with another amino acid residue from the same side chain family.

The term "variable domain" (variable domain of a light chain ($V_L$), variable domain of a heavy chain ($V_H$)) as used herein denotes each of the individual domains of a pair of light and heavy chains of an immunoglobulin which are directly involved in the binding of the target antigen. The variable domains are generally the N-terminal domains of light and heavy chains. The variable domains of the light and heavy chain have the same general structure, i.e. they possess an "immunoglobulin framework", and each domain comprises four "framework regions" (FR), whose sequences are widely conserved, connected by three "hypervariable regions" (or "complementarity determining regions", CDRs). The terms "complementary determining region" (CDR) or "hypervariable region" (HVR), which are used interchangeably within the current application, denote the amino acid residues of an antibody which are mainly involved in antigen-binding. "Framework" regions (FR) are those variable domain regions other than the hypervariable regions. Therefore, the light and heavy chain variable domains of an immunoglobulin comprise from N- to C-terminus the regions FR1, CDR1, FR2, CDR2, FR3, CDR3, and FR4. The framework regions adopt a β-sheet conformation and the CDRs form loops connecting the β-sheet structure. The CDRs in each chain are held in their three-dimensional structure by the framework regions and form together with the CDRs from the other chain the antigen binding site. The immunoglobulin heavy and light chain CDR3 region plays a particularly important role in the binding specificity/affinity of the immunoglobulin. CDR and FR regions are determined according to the standard definition of Kabat, E. A., et al., Sequences of Proteins of Immunological Interest, 5th ed., Public Health Service, National Institutes of Health, Bethesda, Md. (1991).

The term "amino acid" as used within this application denotes the group of carboxy α-amino acids, which directly or in form of a precursor can be encoded by nucleic acid. The individual amino acids are encoded by nucleic acids consisting of three nucleotides, so called codons or base-triplets. Each amino acid is encoded by at least one codon. The encoding of the same amino acid by different codons is known as "degeneration of the genetic code". The term "amino acid" as used within this application denotes the naturally occurring carboxy α-amino acids and comprises alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A "nucleic acid" or a "nucleic acid sequence", which terms are used interchangeably within this application, refers to a polymeric molecule consisting of the individual nucleotides (also called bases) 'a', 'c', 'g', and T (or 'u' in RNA), i.e. to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid, or the chromosome of a host cell. A nucleic acid is characterized by its nucleic acid sequence consisting of individual nucleotides.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

It has now been found that a nucleic acid encoding a monoclonal immunoglobulin can be obtained from a single cell with a method according to the invention comprising a polymerase chain reaction (PCR). Further it has been found that with a combination of the PCR method according to the invention and an in vitro translation method the nucleic acid encoding a monoclonal immunoglobulin can be obtained from a single cell and the encoded immunoglobulin can be provided in quantities sufficient for the characterization of the immunoglobulin's binding properties. In order to amplify the very low amount of mRNA obtained from a single cell, the individual PCR (polymerase chain reaction) has to be very sensitive and a combination of more than one PCR has to be performed.

Thus, it has been found that based on the amplification of nucleic acid encoding cognate IgG HC (immunoglobulin G heavy chain) and IgG LC (immunoglobulin G light chain) of an IgG isotype immunoglobulin from a single cell with subsequent in vitro translation of the obtained amplified nucleic acid Fab fragments or complete immunoglobulins can be provided. With this method a high sensitive method for obtaining information about an immunoglobulin produced by a single cell is provided. This is possible even from the minute amounts of mRNA of a single cell. The method according to the invention allows for the biochemical characterization of the binding characteristics of an immunoglobulin expressed by a single B-cell. Thus, with this method characterization of a higher diversity as opposed to the hybridoma technology is possible. Furthermore, as the cognate immunoglobulin chains are obtained from mature B-cells after antigen contact, selectively the nucleic acids encoding high specific and correctly assembled immunoglobulins are obtained.

The method according to the current invention for obtaining the nucleic acid encoding an immunoglobulin form a single cell comprises a multiplex semi-nested PCR for the amplification of cognate IgG HC and IgG LC (human IgG isotype) from a single B-cell. For characterization of the binding characteristics of the immunoglobulin encoded by the obtained nucleic acid, the PCR product was transformed to a nucleic acid encoding the corresponding Fab-fragment. Thereafter the Fab-fragment was translated in vitro in *E. coli* lysate. The expression was confirmed using ELISA and Western blot methods.

In general one aspect of the current invention is a method employing the following steps i) isolating with magnetic micro-beads coated with human CD 19 B-cells from peripheral blood, ii) depositing single cells e.g. by limited dilution or FACS, iii) extracting the mRNA of the individualized B-cells, iv) obtaining one or more nucleic acids encoding at least the variable domains (VH and VL) of the immunoglobulin produced by the individualized B-cell, v) translating in vitro a linear RNA template, and optionally vi) characterizing the binding properties of the immunoglobulin or immunoglobulin fragment.

The IgG-specific PCR amplification according to the current invention was optimized and modified resulting in an increase in determined OD-values and, thus, obtained immunoglobulin or immunoglobulin fragment after in vitro translation.

Three novel PCR-based approaches were established which are highly sensitive and result in high recovery of the amplified nucleic acids encoding the immunoglobulin's heavy and light chains or fragments thereof. Also provided is a method for the expression of functional and stable Fab fragments after in vitro translation of nucleic acid obtained with the PCR-based method according to the invention.

The terms "polymerase chain reaction" and "PCR", which are used interchangeably in this application, denote a method for specifically amplifying a region of nucleic acids, e.g. of DNA or RNA. This method has been developed by K. Mullis (see e.g. Winkler, M. E., et al., Proc. Natl. Acad. Sci. USA 79 (1982) 2181-2185). The region can be a single gene, a part of a gene, a coding or a non-coding sequence. Most PCR methods typically amplify DNA fragments of hundreds of base pairs (bp), although some techniques allow for amplification of fragments up to 40 kilo base pairs (kb) in size. A basic PCR set up requires several components and reagents. These components include a nucleic acid template that contains the region to be amplified, two primer complementary to the 5'- and 3'-end of the region to be amplified, a polymerase, such as Taq polymerase or another thermostable polymerase, deoxynucleotide triphosphates (dNTPs) from which the polymerase synthesizes a new strand, a buffer solution providing a suitable chemical environment for optimum activity and stability of the polymerase, divalent cations, generally $Mg^{2+}$, and finally, monovalent cations like potassium ions.

The term "semi-nested PCR" denotes two successive polymerase chain reactions each employing at least a pair of PCR primer, wherein in the first polymerase chain reaction a first pair of primer is employed and in the second polymerase chain reaction a second pair of primer is employed. In the first and second pair of primer one of the primer is the same and the other primer is changed, whereby the distance, i.e. the number of nucleotides, between the 3'-end of the first primer and the 5'-end of the second primer is reduced in the pair of primer used in the second polymerase chain reaction compared to the pair of primer used in the first polymerase chain reaction. The changed primer is either the sense primer or the anti-sense primer. The first PCR amplifies a sequence as seen in any PCR experiment. One primer of the second pair of primer, i.e. the nested primer, for the second PCR binds within the first PCR product and produces a second PCR product that is shorter than the first one. The technique, because it uses four specific primer, rather than two, has greater specificity than regular PCR. It can also yield detectable product in cases where simple PCR fails to do so.

The terms "multiplex polymerase chain reaction" or "multiplex PCR", which are used interchangeably within the current application, denote a polymerase chain reaction employing multiple, unique primer in a single PCR reaction/mixture to produce amplicons of varying sizes specific to different DNA sequences. By targeting multiple genes at once, additional information can be obtained from a single test run that otherwise would require several times the reagents and more time to perform. Annealing temperatures for each primer sets must be optimized to work correctly within a single reaction. Besides, amplicon sizes should be different enough to form distinct bands when visualized by gel electrophoresis.

In the human genome the chromosomal loci containing the immunoglobulin encoding genes are located on chromosomes 2, 14, and 22 (see FIG. 1). The human immunoglobulin G heavy chain locus can be found on chromosome 14 (14q32.2) with the chromosomal orientation in the locus: telomere-5'-end-$V_H$-D-$J_H$-$C_H$-3'-end-centromere. The $V_H$ segments on the chromosome are classified as depicted in the following Table 1.

TABLE 1

Grouping of the $V_H$-genes into $V_H$ families according to Matsuda, F., et al., J. Exp. Med. 188 (1998) 2151-2162 and Tomlinson, I. M., et al., V Base sequence directory 1999.

| $V_H$ family | Number of family members | Genes with open reading frame |
| --- | --- | --- |
| $V_H1$ | 14 | 9/11 |
| $V_H2$ | 4 | 3 |
| $V_H3$ | 65 | 22 |
| $V_H4$ | 32 | 7/11 |
| $V_H5$ | 2 | 2 |
| $V_H6$ | 1 | 1 |
| $V_H7$ | 5 | 1 |

The human immunoglobulin G heavy chain locus comprises overall 123-129 $V_H$-genes, of which 51 are functional, 23 functional D-genes (D=diversity), grouped in seven families, 6 functional $J_H$-genes (J=joining) and in the most frequent haplotype 9 functional $C_H$-genes (C=constant).

The locus for the human immunoglobulin G light chains of the types kappa (κ) and lambda (λ) is located on two different chromosomes, chromosomes 2 and 22. The kappa light chain locus can be found on the short arm of chromosome 2 (2p11.2) and comprises 40 functional $V_\kappa$-gene segments. These are grouped in seven families. The locus also comprises 5 $J_\kappa$-genes and a single $C_\kappa$-gene (Schable, K. F. and Zachau, H. G., Biol. Chem. Hoppe Seyler 374 (1993) 1001-1022; Lefranc, M. P., Exp. Clin. Immunogenet. 18 (2001) 161-174).

TABLE 2

Grouping of the $V_\kappa$-genes into $V_\kappa$ families according to Foster, S. J., et al., J. Clin. Invest. 99 (1997) 1614-1627.

| $V_\kappa$ family | Number of functional genes |
| --- | --- |
| $V_\kappa1$ | 19 |
| $V_\kappa2$ | 9 |
| $V_\kappa3$ | 7 |
| $V_\kappa4$ | 1 |
| $V_\kappa5$ | 1 |
| $V_\kappa6$ | 3 |

The lambda light chain locus can be found on the long arm of chromosome 22 (22p11.2) and comprises 73-74 $V_\lambda$-gene of which 30 are functional. These are grouped in ten families which in addition are grouped in three clusters. The locus also comprises 7 $J_\lambda$-genes, of which 5 are functional.

TABLE 3

Grouping of the $V_\lambda$-genes into $V_\lambda$ families according to Frippiat, J. P., et al., Hum. Mol. Genet. 4 (1995) 983-991; Farner, N. L., et al., J. Immunol. 162 (1999) 2137-2145; Lefranc, M. P., Exp. Clin. Immunogenet. 18 (2001) 242-254.

| $V_\lambda$ family | Number of functional genes | Cluster |
|---|---|---|
| $V_\lambda 1$ | 5 | B |
| $V_\lambda 2$ | 5 | A |
| $V_\lambda 3$ | 8 | A |
| $V_\lambda 4$ | 3 | A-C |
| $V_\lambda 5$ | 3 | B |
| $V_\lambda 6$ | 1 | C |
| $V_\lambda 7$ | 2 | B |
| $V_\lambda 8$ | 1 | C |
| $V_\lambda 9$ | 1 | B |
| $V_\lambda 10$ | 1 | C |

The PCR-based amplification of the nucleic acid encoding an IgG HC and LC or at least the variable domain thereof from a single immunoglobulin producing cell, e.g. from a single B-cell, is based on the single cell deposition of B-lymphocytes followed by a PCR based nucleic acid amplification with specific primer for the variable domain of the heavy and light chain. The outcome of the PCR is essentially depending on the employed PCR primer. At best the employed primer should cover all V-genes, should not be prone to dimer formation and should specifically bind to the cDNA encoding the immunoglobulin. Thus, in one embodiment the nucleic acid encoding an immunoglobulin variable domain is obtained from cDNA.

Due to the large number of functional genes on the human immunoglobulin G locus it is necessary to employ different primer in the PCR reaction in order to cover as many known genes as possible. Therefore, a set of degenerated primer has been established which is also an aspect of the current invention. In one embodiment the amplification of the nucleic acid encoding the heavy and light chain is performed in one polymerase chain reaction. In this embodiment the primer are chosen in order to provide for the amplification of nucleic acids of approximately the same length in order to allow for the same PCR conditions. In this embodiment primer for the nucleic acid encoding the heavy chain are employed whereof one is binding in the heavy chain $C_H 1$ region, thus, providing for a nucleic acid fragment of comparable size to that of the corresponding nucleic acid encoding the light chain.

One aspect of the current invention is a method for obtaining a nucleic acid encoding at least an immunoglobulin variable domain from a single cell comprising the following steps:
  obtaining a first nucleic acid composition by performing a first polymerase chain reaction with three to six 5'-primer and one 3'-primer,
  obtaining a nucleic acid encoding an immunoglobulin variable domain by performing with the composition obtained in the first polymerase chain reaction a second polymerase chain reaction with thirteen to sixteen 5'-primer and one 3'-primer,
whereby the distance of the binding locations of the primer employed in the second polymerase chain reaction is reduced compared to the first polymerase chain reaction.

In one embodiment of this method the 5'-primer employed in the first polymerase chain reaction bind in the coding region for the leader peptide of the immunoglobulin. In another embodiment the 5'-primer employed in the second polymerase chain reaction bind in the coding region for the first framework region of the immunoglobulin. In another embodiment the primer employed in the second polymerase chain reaction provide for overhangs encoding the translational start codon ATG for 5'-primer and/or the translational stop codon TTA for 3'-primer. This overhang is useful in an optional following overlapping polymerase chain reaction for the generation of nucleic acids for the in vitro translation of the obtained nucleic acid. In one embodiment the immunoglobulin variable domain is an immunoglobulin heavy chain variable domain or an immunoglobulin kappa light chain variable domain or an immunoglobulin lambda light chain variable domain.

In one embodiment of the methods according to the invention the primer employed in the first polymerase chain reaction for obtaining a nucleic acid encoding an immunoglobulin heavy chain variable domain have the nucleic acid sequence of SEQ ID NO: 05 and/or 06, and SEQ ID NO: 07 and/or 08, and SEQ ID NO: 09, and SEQ ID NO: 10 and/or 11, and SEQ ID NO: 12, and SEQ ID NO: 13, and SEQ ID NO: 14 and/or 15.

TABLE 4

Primer employed in the first polymerase chain reaction for obtaining a nucleic acid encoding an immunoglobulin heavy chain variable domain.

| Primer description | Sequence | Denotation | SEQ ID NO: |
|---|---|---|---|
| $V_H$ primer binding in the leader peptide coding region | TCACCATGGACTG(C/G)ACCTGGA | $V_H$L-1 | 05, 06 |
| | CCATGGACACACTTTG(C/T)TCCAC | $V_H$L-2 | 07, 08 |
| | TCACCATGGAGTTTGGGCTGAGC | $V_H$L-3 | 09 |
| | AGAACATGAAACA(C/T)CTGTGGTTCTT | $V_H$L-4 | 10, 11 |
| | ATGGGGTCAACCGCCATCCT | $V_H$L-5 | 12 |
| | ACAATGTCTGTCTCCTTCCTCAT | $V_H$L-6 | 13 |
| primer binding in the constant region coding region | GCCAGGGGGAAGAC(C/G)GATG | hu$C_H$-II | 14, 15 |

In one embodiment of the methods according to the invention the primer employed in the first polymerase chain reaction for obtaining a nucleic acid encoding an immunoglobulin kappa light chain variable domain have the nucleic acid sequence of SEQ ID NO: 16 to 20.

TABLE 5

Primer employed in the first polymerase chain reaction for obtaining a nucleic acid encoding an immunoglobulin kappa light chain variable domain.

| Primer description | Sequence | Denotation | SEQ ID NO: |
|---|---|---|---|
| $V_\kappa$ primer binding in the leader peptide coding region | GCTCAGCTCCTGGGGCTCCTG<br>CTGGGGCTGCTAATGCTCTGG<br>TTCCTCCTGCTACTCTGGCTC<br>CAGACCCAGGTCTTCATTTCT | $V_\kappa L$-1<br>$V_\kappa L$-2<br>$V_\kappa L$-3<br>$V_\kappa L$-4 | 16<br>17<br>18<br>19 |
| primer binding in the constant region coding region | TTTCAACTGCTCATCAGATGGCGG | $huC_\kappa$-II | 20 |

In one embodiment of the methods according to the invention the primer employed in the first polymerase chain reaction for obtaining a nucleic acid encoding an immunoglobulin lambda light chain variable domain have the nucleic acid sequence of SEQ ID NO: 21, and SEQ ID NO: 22, and SEQ ID NO: 23 and/or 24 and/or 25 and/or 26, and SEQ ID NO: 27 and/or 28.

TABLE 6

Primer employed in the first polymerase chain reaction for obtaining a nucleic acid encoding an immunoglobulin lambda light chain variable domain.

| Primer description | sequence | denotation | SEQ ID NO: |
|---|---|---|---|
| $V_\lambda$ primer binding in the leader peptide coding region | CCTCTCCTCCTCACCCTCCT<br>CTCCTCACTCAGGGCACA<br>ATGGCCTGGA(T/C)C(C/G)CTCTCC | $V_\lambda L$-1<br>$V_\lambda L$-2<br>$V_\lambda L$-3 | 21<br>22<br>23, 24, 25, 26 |
| primer binding in the constant region coding region | AGCTCCTCAGAGGAGGG(C/T)GG | $C_\lambda II$ | 27, 28 |

In one embodiment of the methods according to the invention the primer employed in the second polymerase chain reaction for obtaining a nucleic acid encoding an immunoglobulin heavy chain variable domain have the nucleic acid sequence of SEQ ID NO: 29 and/or 30, and SEQ ID NO: 31, and SEQ ID NO: 32 and/or 33, and SEQ ID NO: 34 and/or 35, and SEQ ID NO: 36, and SEQ ID NO: 37 and/or 38, and SEQ ID NO: 39 and/or 40, and SEQ ID NO: 41, and SEQ ID NO: 42, and SEQ ID NO: 43 and/or 44, and SEQ ID NO: 45, and SEQ ID NO: 46 and/or 47, and SEQ ID NO: 48, and SEQ ID NO: 49 and/or 50, and SEQ ID NO: 51 and/or 52.

TABLE 7

Primer employed in the second polymerase chain reaction for obtaining a nucleic acid encoding an immunoglobulin heavy chain variable domain.

| Primer description | Sequence | Denotation | SEQ ID NO: |
|---|---|---|---|
| $V_H$ primer binding in the FR1 coding region | CTTTAAGAAGGAGATATACCATGGT(G/T)CAGCTGGTGCAG | $V_H L$-1a | 29, 30 |
| | CTTTAAGAAGGAGATATACCATGCAGGTCCAGCTTGTGCAG | $V_H L$-1b | 31 |
| | CTTTAAGAAGGAGATATACCATG(G/C)AGGTCCAGCTGGTACAG | $V_H L$-1c | 32, 33 |
| | CTTTAAGAAGGAGATATACCATGCA(A/G)ATGCAGCTGGTGCAG | $V_H L$-1d | 34, 35 |
| | CTTTAAGAAGGAGATATACCATGCAG ATCACCTTGAAGGAG | $V_H L$-2a | 36 |

TABLE 7-continued

Primer employed in the second polymerase chain reaction for obtaining a nucleic acid encoding an immunoglobulin heavy chain variable domain.

| Primer description | Sequence | Denotation | SEQ ID NO: |
|---|---|---|---|
| | CTTTAAGAAGGAGATATACCATGCAG GTCACCTTGA(A/G)GGAG | $V_HL$-2b | 37, 38 |
| | CTTTAAGAAGGAGATATACCATGGA(A/G)GTGCAGCTGGTGGAG | $V_HL$-3a | 39, 40 |
| | CTTTAAGAAGGAGATATACCATGCAG GTGCAGCTGGTGGAG | $V_HL$-3b | 41 |
| | CTTTAAGAAGGAGATATACCATGGAG GTGCAGCTGTTGGAG | $V_HL$-3c | 42 |
| | CTTTAAGAAGGAGATATACCATGCAG (C/G)TGCAGCTGCAGGAG | $V_HL$-4a | 43, 44 |
| | CTTTAAGAAGGAGATATACCATGCAG GTGCAGCTACAGCAG | $V_HL$-4b | 45 |
| | CTTTAAGAAGGAGATATACCATGGA(A/G)GTGCAGCTGGTGCAG | $V_HL$-5a | 46, 47 |
| | CTTTAAGAAGGAGATATACCATGCAG GTACAGCTGCAGCAG | $V_HL$-6a | 48 |
| | CTTTAAGAAGGAGATATACCATGCAG GT(C/G)CAGCTGGTGCAA | $V_HL$-7a | 49, 50 |
| primer binding in the constant region coding region | ATCGTATGGGTAGCTGGTCCCTTAG AC(C/G)GATGGGCCCTTGGTGGA | $huC_H$-III | 51, 52 |

In one embodiment of the methods according to the invention the primer employed in the second polymerase chain reaction for obtaining a nucleic acid encoding an immunoglobulin kappa light chain variable domain have the nucleic acid sequence of SEQ ID NO: 53 and/or 54, and SEQ ID NO: 55 and/or 56, and SEQ ID NO: 57 and/or 58, and SEQ ID NO: 59, and SEQ ID NO: 60, and SEQ ID NO: 61 and/or 62, and SEQ ID NO: 63 and/or 64, and SEQ ID NO: 65, and SEQ ID NO: 66, and SEQ ID NO: 67, and SEQ ID NO: 68, and SEQ ID NO: 69, and SEQ ID NO: 70, and SEQ ID NO: 71.

TABLE 8

Primer employed in the second polymerase chain reaction for obtaining a nucleic acid encoding an immunoglobulin kappa light chain variable domain.

| Primer description | Sequence | Denotation | SEQ ID NO: |
|---|---|---|---|
| $V_\kappa$ primer binding in the FR1 coding region | CTTTAAGAAGGAGATATACCATG(A/G)ACATCCAGATGACCCAG | $V_\kappa L$-1a | 53, 54 |
| | CTTTAAGAAGGAGATATACCATGG(A/C)CATCCAGTTGACCCAG | $V_\kappa L$-1b | 55, 56 |
| | CTTTAAGAAGGAGATATACCATGGCCATCC(A/G)GATGACCCAG | $V_\kappa L$-1c | 57, 58 |
| | CTTTAAGAAGGAGATATACCATGGTCATCTGGATGACCCAG | $V_\kappa L$-1d | 59 |
| | CTTTAAGAAGGAGATATACCATGGATATTGTGATGACCCAG | $V_\kappa L$-2a | 60 |
| | CTTTAAGAAGGAGATATACCATGGAT(A/G)TTGTGATGACTCAG | $V_\kappa L$-2b | 61, 62 |
| | CTTTAAGAAGGAGATATACCATGGAAATTGTGTTGAC(A/G)CAG | $V_\kappa L$-3a | 63, 64 |
| | CTTTAAGAAGGAGATATACCATGGAAATAGTGATGACGCAG | $V_\kappa L$-3b | 65 |
| | CTTTAAGAAGGAGATATACCATGGAAATTGTAATGACACAG | $V_\kappa L$-3c | 66 |
| | CTTTAAGAAGGAGATATACCATGGACATCGTGATGACCCAG | $V_\kappa L$-4a | 67 |
| | CTTTAAGAAGGAGATATACCATGGAAACGACACTCACGCAG | $V_\kappa L$-5a | 68 |
| | CTTTAAGAAGGAGATATACCATGGAAATTGTGCTCACTCAG | $V_\kappa L$-6a | 69 |
| | CTTTAAGAAGGAGATATACCATGGATGTTGTGATGACACAG | $V_\kappa L$-6b | 70 |

TABLE 8-continued

Primer employed in the second polymerase chain reaction for obtaining a nucleic acid encoding an immunoglobulin kappa light chain variable domain.

| Primer description | Sequence | Denotation | SEQ ID NO: |
|---|---|---|---|
| primer binding in the constant region coding region | ATCGTATGGGTAGCTGGTCCCTTAA AGATGAAGACAGATGGTGC | $huC_k$-III | 71 |

In one embodiment of the methods according to the invention the primer employed in the second polymerase chain reaction for obtaining a nucleic acid encoding an immunoglobulin lambda light chain variable domain have the nucleic acid sequence of SEQ ID NO: 72, and SEQ ID NO: 73 and/or 74, and SEQ ID NO: 75, and SEQ ID NO: 76, and SEQ ID NO: 77 and/or 78, and SEQ ID NO: 79, and SEQ ID NO: 80, and SEQ ID NO: 81, and SEQ ID NO: 82 and/or 83, and SEQ ID NO: 84 and/or 85, and SEQ ID NO: 86, and SEQ ID NO: 87 and/or 88, and SEQ ID NO: 89, and SEQ ID NO: 90 and/or 91, and SEQ ID NO: 92, and SEQ ID NO: 93.

A further aspect of the current invention is a method for obtaining a nucleic acid encoding at least an immunoglobulin variable domain from a single cell comprising the following step:
   obtaining a first nucleic acid composition by performing a first polymerase chain reaction with three or four 5'-primer and one 3'-primer,
   obtaining a nucleic acid encoding at least an immunoglobulin variable domain by performing with the composition obtained in the first polymerase chain reaction a second polymerase chain reaction with one 5'-primer and one 3'-primer,

TABLE 9

Primer employed in the second polymerase chain reaction for obtaining a nucleic acid encoding an immunoglobulin lambda light chain variable domain.

| Primer description | Sequence | Denotation | SEQ ID NO: |
|---|---|---|---|
| $V_\lambda$ primer binding in the FR1 coding region | CTTTAAGAAGGAGATATACCATGCA GTCTGTGCTGACTCAG | $V_\lambda$L-1a | 72 |
| | CTTTAAGAAGGAGATATACCATGCA GTCTGTG(C/T)TGACGCAG | $V_\lambda$L-1b | 73, 74 |
| | CTTTAAGAAGGAGATATACCATGCA GTCTGTCGTGACGCAG | $V_\lambda$L-1c | 75 |
| | CTTTAAGAAGGAGATATACCATGCA GTCTGCCCTGACTCAG | $V_\lambda$L-2a | 76 |
| | CTTTAAGAAGGAGATATACCATGTC CTATG(A/T)GCTGACTCAG | $V_\lambda$L-3a | 77, 78 |
| | CTTTAAGAAGGAGATATACCATGTC CTATGAGCTGACACAG | $V_\lambda$L-3b | 79 |
| | CTTTAAGAAGGAGATATACCATGTC TTCTGAGCTGACTCAG | $V_\lambda$L-3c | 80 |
| | CTTTAAGAAGGAGATATACCATGTC CTATGAGCTGATGCAG | $V_\lambda$L-3d | 81 |
| | CTTTAAGAAGGAGATATACCATGCA GC(C/T)TGTGCTGACTCAA | $V_\lambda$L-4a | 82, 83 |
| | CTTTAAGAAGGAGATATACCATGCAG (C/G)CTGTGCTGACTCAG | $V_\lambda$L-5a | 84, 85 |
| | CTTTAAGAAGGAGATATACCATGAA TTTTATGCTGACTCAG | $V_\lambda$L-6a | 86 |
| | CTTTAAGAAGGAGATATACCATGCAG (A/G)CTGTGGTGACTCAG | $V_\lambda$L-7a | 87, 88 |
| | CTTTAAGAAGGAGATATACCATGCAG ACTGTGGTGACCCAG | $V_\lambda$L-8a | 89 |
| | CTTTAAGAAGGAGATATACCATGC (A/T)GCCTGTGCTGACTCAG | $V_\lambda$L-4/9a | 90, 91 |
| | CTTTAAGAAGGAGATATACCATGCAG GCAGGGCTGACTCAG | $V_\lambda$L-10a | 92 |
| primer binding in the constant region coding region | ATCGTATGGGTAGCTGGTCCCTTAG GGAACAGAGTGACCG | $huC_\lambda$-III | 93 | whereby primer employed in the first and in the second polymerase chain reaction can be the same.

In one embodiment the primer employed in the polymerase chain reaction provide for overhangs encoding the translational start codon ATG for 5'-primer and/or the translational stop codon TTA for 3'-primer. This overhang is useful in an optional following overlapping polymerase chain reaction for the generation of nucleic acids for the in vitro translation of the obtained nucleic acid. In one embodiment the immunoglobulin variable domain is an immunoglobulin heavy chain variable domain or an immunoglobulin kappa light chain variable domain or an immunoglobulin lambda light chain variable domain.

In one embodiment of this method the primer employed in the first two-step polymerase chain reaction for obtaining a nucleic acid encoding an immunoglobulin heavy chain variable domain have the nucleic acid sequence of SEQ ID NO: 94, and SEQ ID NO: 95, and SEQ ID NO: 96 and/or 97 and/or 98 and/or 99, and SEQ ID NO: 100 and/or 101 and/or 102 and/or 103, and SEQ ID NO: 104 and/or 105 and/or 106.

TABLE 10

Primer employed in the first two-step polymerase chain reaction for obtaining a nucleic acid encoding an immunoglobulin heavy chain variable domain.

| Primer description | Sequence | Denotation | SEQ ID NO: |
|---|---|---|---|
| $V_H$ primer binding in the FR1 coding region | CTTTAAGAAGGAGATATACCATGCA GGTGCAGCTGGTGCAGTC | $huV_H$-1 | 94 |
| | CTTTAAGAAGGAGATATACCATGCA GGTCAACTTAAGGGAGTCTGG | $huV_H$-2 | 95 |
| | CTTTAAGAAGGAGATATACCATGAG GTGCAGCTG(C/G)TG(C/G)AGTC | $huV_H$-3 | 96, 97, 98, 99 |
| | CTTTAAGAAGGAGATATACCATGCA GGT(A/G)CAGCTGCAG(C/G)AGTC | $huV_H$-4 | 100, 101, 102, 103 |
| primer binding in the constant region coding region | ATCGTATGGGTAGCTGGTCCCTTA GTGGTGGTGGTGGTGGTGAACT (C/G/T)TCTTGTCCACCTTGGTGTTG | $huC_H$-2 | 104, 105, 106 |

In one embodiment of this method the primer employed in the first two-step polymerase chain reaction for obtaining a nucleic acid encoding an immunoglobulin kappa light chain variable domain have the nucleic acid sequence of SEQ ID NO: 107 and/or 108 and/or 109 and/or 110, and SEQ ID NO: 111 and/or 112, and SEQ ID NO: 113, and SEQ ID NO: 114, and SEQ ID NO: 115.

TABLE 11

Primer employed in the first two-step polymerase chain reaction for obtaining a nucleic acid encoding an immunoglobulin kappa light chain variable domain.

| Primer description | Sequence | Denotation | SEQ ID NO: |
|---|---|---|---|
| $V_\kappa$ primer binding in the FR1 coding region | CTTTAAGAAGGAGATATACCATGG A CATC(C/G)(A/T)GATGACCCAGTCT | $huV_\kappa$-1 | 107, 108, 109, 110 |
| | CTTTAAGAAGGAGATATACCATGG A TATTGTG(A/C)TGACTCAGTCTCC | $huV_\kappa$-2 | 111, 112 |
| | CTTTAAGAAGGAGATATACCATGG A AATTGTGTTGACGCAGTCTCC | $huV_\kappa$-3 | 113 |
| | CTTTAAGAAGGAGATATACCATGG A AACGACACTCACGCAGTCTC | $huV_\kappa$-4 | 114 |
| primer binding in the constant region coding region | ATCGTATGGGTAGCTGGTCCCTTAA CACTCTCCCCTGTTGAAGCTC | $huC_\kappa$-2 | 115 |

In one embodiment of this method the primer employed in the first two-step polymerase chain reaction for obtaining a nucleic acid encoding an immunoglobulin lambda light chain variable domain have the nucleic acid sequence of SEQ ID NO: 116, and SEQ ID NO: 117, and SEQ ID NO: 118 and/or 119, and SEQ ID NO: 120 and/or 121 and/or 122 and/or 123 and/or 124 and/or 125.

TABLE 12

Primer employed in the first two-step polymerase chain reaction for obtaining a nucleic acid encoding an immunoglobulin lambda light chain variable domain.

| Primer description | Sequence | Denotation | SEQ ID NO: |
|---|---|---|---|
| $V_\lambda$ primer binding in the FR1 coding region | CTTTAAGAAGGAGATATACCATG CAGTCTGTGCTGACTCAGCC | $huV_\lambda$-1 | 116 |
|  | CTTTAAGAAGGAGATATACCATG CAGTCTGCCCTGACTCAGCC | $huV_\lambda$-2 | 117 |
|  | CTTTAAGAAGGAGATATACCATG TCCTATGAGCTGAC(A/T)CAGCC | $huV_\lambda$-3 | 118, 119 |
| primer binding in the constant region coding region | ATCGTATGGGTAGCTGGTCCCTTA TGAACATTC(C/T)G(C/T)AGGGGC (A/T)ACT | $huC_\lambda$-2 | 120, 121, 122, 123, 124, 125 |

In one embodiment of this method the primer employed in the second two-step polymerase chain reaction have the nucleic acid sequence of SEQ ID NO: 126 and SEQ ID NO: 127.

TABLE 13

Primer employed in the second two-step polymerase chain reaction.

| Primer description | Sequence | Denotation | SEQ ID NO: |
|---|---|---|---|
| first primer | CTTTAAGAAGGAGATATACCATG | LTGS-1fp | 126 |
| second primer | ATCGTATGGGTAGCTGG | LTGS-rfp | 127 |

Another aspect of the current invention is a method for obtaining a nucleic acid encoding at least an immunoglobulin variable domain from a single cell comprising the following steps:
  obtaining a first nucleic acid composition by performing a first polymerase chain reaction with four to six 5'-primer and one 3'-primer,
  obtaining a nucleic acid encoding at least an immunoglobulin variable domain by performing with the composition obtained in the first polymerase chain reaction a second polymerase chain reaction with thirteen to fifteen 5'-primer and one 3'-primer,
whereby in the second polymerase chain reaction either the 5'-primer are the same as in the first polymerase chain reaction and the 3'-primer is different or the 3'-primer is the same as in the first polymerase chain reaction and at least one 5'-primer is different, and whereby in the second polymerase chain reaction the number of nucleotides between the 5'-end of each of the 5'-primer and the 3'-end of the 3'-primer is smaller compared to the number of nucleotides between the 5'-end of each of the 5'-primer and the 3'-end of the 3'-primer in the first polymerase chain reaction.

In one embodiment of this method the 5'-primer employed in the first polymerase chain reaction bind in the coding region for the leader peptide of the immunoglobulin. In another embodiment the 5'-primer employed in the second polymerase chain reaction bind in the coding region for the first framework region of the immunoglobulin. In another embodiment the primer employed in the second polymerase chain reaction provide for overhangs encoding the translational start codon ATG for 5'-primer and/or the translational stop codon TTA for 3'-primer. This overhang is useful in an optional following overlapping polymerase chain reaction for the generation of nucleic acids for the in vitro translation of the obtained nucleic acid. In one embodiment of this method for obtaining an immunoglobulin variable domain encoding nucleic acid six 5'-primer and one 3'-primer are employed in the first polymerase chain reaction. In another embodiment four 5'-primer and one 3'-primer are employed in the second polymerase chain reaction. In one embodiment the immunoglobulin variable domain is an immunoglobulin heavy chain variable domain or an immunoglobulin kappa light chain variable domain or an immunoglobulin lambda light chain variable domain.

In one embodiment of the methods according to the invention the primer employed in the first polymerase chain reaction for obtaining a nucleic acid encoding an immunoglobulin heavy chain variable domain have the nucleic acid sequence of SEQ ID NO: 05 and/or 06, and SEQ ID NO: 07 and/or 08, and SEQ ID NO: 09, and SEQ ID NO: 10 and/or 11, and SEQ ID NO: 12, and SEQ ID NO: 13, and SEQ ID NO: 104 and/or 105 and/or 106.

TABLE 14

Primer employed in the first polymerase chain reaction for obtaining a nucleic acid encoding an immunoglobulin heavy chain variable domain.

| Primer description | Sequence | Denotation | SEQ ID NO: |
|---|---|---|---|
| $V_H$ primer binding in the | TCACCATGGACTG(C/G)ACCTGGA | $V_H$L-1 | 05, 06 |
|  | CCATGGACACACTTTG(C/T)TCCAC | $V_H$L-2 | 07, 08 |

TABLE 14-continued

Primer employed in the first polymerase chain reaction for obtaining a nucleic acid encoding an immunoglobulin heavy chain variable domain.

| Primer description | Sequence | Denotation | SEQ ID NO: |
|---|---|---|---|
| leader peptide coding region | TCACCATGGAGTTTGGGCTGAGC<br>AGAACATGAAACA(C/T)CTGTGGTTCTT<br>ATGGGGTCAACCGCCATCCT<br>ACAATGTCTGTCTCCTTCCTCAT | $V_HL$-3<br>$V_HL$-4<br>$V_HL$-5<br>$V_HL$-6 | 09<br>10, 11<br>12<br>13 |
| primer binding in the constant region coding region | TCGTATGGGTAGCTGGTCCCTTAGTGGT<br>GGTGGTGGTGGTGAACT(C/G/T)TCTTG<br>TCCACCTTGGTGTTG | $huC_H$-2 | 104,<br>105,<br>106 |

In one embodiment of the methods according to the invention the primer employed in the first polymerase chain reaction for obtaining a nucleic acid encoding an immunoglobulin kappa light chain variable domain have the nucleic acid sequence of SEQ ID NO: 16, and SEQ ID NO: 17, and SEQ ID NO: 18, and SEQ ID NO: 19, and SEQ ID NO: 115.

In one embodiment of the methods according to the invention the primer employed in the second polymerase chain reaction for obtaining a nucleic acid encoding an immunoglobulin heavy chain variable domain have the nucleic acid

TABLE 15

Primer employed in the first polymerase chain reaction for obtaining a nucleic acid encoding an immunoglobulin kappa light chain variable domain.

| Primer description | Sequence | Denotation | SEQ ID NO: |
|---|---|---|---|
| $V_\kappa$ primer binding in the leader peptide coding region | GCTCAGCTCCTGGGGCTCCTG<br>CTGGGGCTGCTAATGCTCTGG<br>TTCCTCCTGCTACTCTGGCTC<br>CAGACCCAGGTCTTCATTTCT | $V_\kappa L$-1<br>$V_\kappa L$-2<br>$V_\kappa L$-3<br>$V_\kappa L$-4 | 16<br>17<br>18<br>19 |
| primer binding in the constant region coding region | ATCGTATGGGTAGCTGGTCCC<br>TTAACACTCTCCCCTGTTGAA<br>GCTC | $huC_\kappa$-2 | 115 |

In one embodiment of the methods according to the invention the primer employed in the first polymerase chain reaction for obtaining a nucleic acid encoding an immunoglobulin lambda light chain variable domain have the nucleic acid sequence of SEQ ID NO: 21, and SEQ ID NO: 22, and SEQ ID NO: 23 and/or 24 and/or 25 and/or 26, and SEQ ID NO: 120 and/or 121 and/or 122 and/or 123 and/or 124 and/or 125.

sequence of SEQ ID NO: 128, and SEQ ID NO: 129, and SEQ ID NO: 130, and SEQ ID NO: 131, and SEQ ID NO: 132, and SEQ ID NO: 133, and SEQ ID NO: 134, and SEQ ID NO: 135, and SEQ ID NO: 136, and SEQ ID NO: 137, and SEQ ID NO: 138, and SEQ ID NO: 139, and SEQ ID NO: 140, SEQ and ID NO: 141, and SEQ ID NO: 104 and/or 105 and/or 106.

TABLE 16

Primer employed in the first polymerase chain reaction for obtaining a nucleic acid encoding an immunoglobulin lambda light chain variable domain.

| Primer description | Sequence | Denotation | SEQ ID NO: |
|---|---|---|---|
| $V_\lambda$ primer binding in the leader peptide coding region | CCTCTCCTCCTCACCCTCCT<br>CTCCTCACTCAGGGCACA<br>ATGGCCTGGA(T/C)C(C/G)CTCTCC | $V_\lambda L$-1<br>$V_\lambda L$-2<br>$V_\lambda L$-3 | 21<br>22<br>23, 24,<br>25, 26 |
| primer binding in the constant region coding region | ATCGTATGGGTAGCTGGTCCCTTA<br>TGAACATTC(C/T)G(C/T)AGGGGC<br>(A/T)ACT | $huC_\lambda$-2 | 120, 121,<br>122, 123,<br>124, 125 |

TABLE 17

Primer employed in the second polymerase chain reaction for obtaining a nucleic acid encoding an immunoglobulin heavy chain variable domain.

| Primer description | Sequence | Denotation | SEQ ID NO: |
|---|---|---|---|
| $V_H$ primer binding in the FR1 coding region | CTTTAAGAAGGAGATATACCATGCA GGTKCAGCTGGTGCAG | $V_H$-1a | 128 |
| | CTTTAAGAAGGAGATATACCATGCA GGTCCAGCTTGTGCAG | $V_H$-1b | 129 |
| | CTTTAAGAAGGAGATATACCATGSA GGTCCAGCTGGTACAG | $V_H$-1c | 130 |
| | CTTTAAGAAGGAGATATACCATGCA RATGCAGCTGGTGCAG | $V_H$-1d | 131 |
| | CTTTAAGAAGGAGATATACCATGCA GATCACCTTGAAGGAG | $V_H$-2a | 132 |
| | CTTTAAGAAGGAGATATACCATGCA GGTCACCTTGARGGAG | $V_H$-2b | 133 |
| | CTTTAAGAAGGAGATATACCATGGA RGTGCAGCTGGTGGAG | $V_H$-3a | 134 |
| | CTTTAAGAAGGAGATATACCATGCA GGTGCAGCTGGTGGAG | $V_H$-3b | 135 |
| | CTTTAAGAAGGAGATATACCATGGA GGTGCAGCTGTTGGAG | $V_H$-3c | 136 |
| | CTTTAAGAAGGAGATATACCATGCA GSTGCAGCTGCAGGAG | $V_H$-4a | 137 |
| | CTTTAAGAAGGAGATATACCATGCA GGTGCAGCTACAGCAG | $V_H$-4b | 138 |
| | CTTTAAGAAGGAGATATACCATGGA RGTGCAGCTGGTGCAG | $V_H$-5a | 139 |
| | CTTTAAGAAGGAGATATACCATGCA GGTACAGCTGCAGCAG | $V_H$-6a | 140 |
| | CTTTAAGAAGGAGATATACCATGCA GGTACAGCTGGTGCAA | $V_H$-7a | 141 |
| primer binding in the constant region coding region | ATCGTATGGGTAGCTGGTCCCTTAGT | $huC_H$-2 | 104, |
| | GGTGGTGGTGGTGGTGAACT(C/G/T)T | | 105, |
| | CTTGTCCACCTTGGTGTTG | | 106 |

In one embodiment of the methods according to the invention the primer employed in the second polymerase chain reaction for obtaining a nucleic acid encoding an immunoglobulin kappa light chain variable domain have the nucleic acid sequence of SEQ ID NO: 53 and/or 54, and SEQ ID NO: 55 and/or 56, and SEQ ID NO: 57 and/or 58, and SEQ ID NO: 59, and SEQ ID NO: 60, and SEQ ID NO: 61 and/or 62, SEQ ID NO: 63 and/or 64, and SEQ ID NO: 65, and SEQ ID NO: 66, and SEQ ID NO: 67, and SEQ ID NO: 68, and SEQ ID NO: 69, and SEQ ID NO: 70, and SEQ ID NO: 115.

TABLE 18

Primer employed in the second polymerase chain reaction for obtaining a nucleic acid encoding an immunoglobulin kappa light chain variable domain.

| Primer description | Sequence | Denotation | SEQ ID NO: |
|---|---|---|---|
| $V_\kappa$ primer binding in the FR1 coding region | CTTTAAGAAGGAGATATACCATG(A/G) ACATCCAGATGACCCAG | $V_\kappa$L-1a | 53, 54 |
| | CTTTAAGAAGGAGATATACCATGG(A/ C)CATCCAGTTGACCCAG | $V_\kappa$L-1b | 55, 56 |
| | CTTTAAGAAGGAGATATACCATGGCC ATCC(A/G)GATGACCCAG | $V_\kappa$L-1c | 57, 58 |
| | CTTTAAGAAGGAGATATACCATGGTC ATCTGGATGACCCAG | $V_\kappa$L-1d | 59 |
| | CTTTAAGAAGGAGATATACCATGGAT ATTGTGATGACCCAG | $V_\kappa$L-2a | 60 |
| | CTTTAAGAAGGAGATATACCATGGAT (A/G)TTGTGATGACTCAG | $V_\kappa$L-2b | 61, 62 |
| | CTTTAAGAAGGAGATATACCATGGA AATTGTGTTGAC(A/G)CAG | $V_\kappa$L-3a | 63, 64 |
| | CTTTAAGAAGGAGATATACCATGGA AATAGTGATGACGCAG | $V_\kappa$L-3b | 65 |
| | CTTTAAGAAGGAGATATACCATGGA AATTGTAATGACACAG | $V_\kappa$L-3c | 66 |
| | CTTTAAGAAGGAGATATACCATGGA CATCGTGATGACCCAG | $V_\kappa$L-4a | 67 |

TABLE 18-continued

Primer employed in the second polymerase chain reaction for obtaining a nucleic acid encoding an immunoglobulin kappa light chain variable domain.

| Primer description | Sequence | Denotation | SEQ ID NO: |
|---|---|---|---|
|  | CTTTAAGAAGGAGATATACCATGGAAACGACACTCACGCAG | $V_\kappa$L-5a | 68 |
|  | CTTTAAGAAGGAGATATACCATGGAAATTGTGCTGACTCAG | $V_\kappa$L-6a | 69 |
|  | CTTTAAGAAGGAGATATACCATGGATGTTGTGATGACACAG | $V_\kappa$L-6b | 70 |
| primer binding in the constant region coding region | ATCGTATGGGTAGCTGGTCCCTTAACACTCTCCCTGTTGAAGCTC | $huC_\kappa$-2 | 115 |

In one embodiment of the methods according to the invention the primer employed in the second polymerase chain reaction for obtaining a nucleic acid encoding an immunoglobulin lambda light chain variable domain have the nucleic acid sequence of SEQ ID NO: 72, and SEQ ID NO: 73 and/or 74, and SEQ ID NO: 75, and SEQ ID NO: 76, and SEQ ID NO: 77 and/or 78, and SEQ ID NO: 79, and SEQ ID NO: 80, and SEQ ID NO: 81, and SEQ ID NO: 82 and/or 83, and SEQ ID NO: 84 and/or 85, and SEQ ID NO: 86, and SEQ ID NO: 87 and/or 88, and SEQ ID NO: 89, and SEQ ID NO: 90 and/or 91, and SEQ ID NO: 92, and SEQ ID NO: 120 or 121 or 122 or 123 or 124 or 125.

TABLE 19

Primer employed in the second polymerase chain reaction for obtaining a nucleic acid encoding an immunoglobulin lambda light chain variable domain.

| Primer description | Sequence | Denotation | SEQ ID NO: |
|---|---|---|---|
| $V_\lambda$ primer binding in the FR1 coding region | CTTTAAGAAGGAGATATACCATGCAGTCTGTGCTGACTCAG | $V_\lambda$L-1a | 72 |
|  | CTTTAAGAAGGAGATATACCATGCAGTCTGTG(C/T)TGACGCAG | $V_\lambda$L-1b | 73, 74 |
|  | CTTTAAGAAGGAGATATACCATGCAGTCTGTCGTGACGCAG | $V_\lambda$L-1c | 75 |
|  | CTTTAAGAAGGAGATATACCATGCAGTCTGCCCTGACTCAG | $V_\lambda$L-2 | 76 |
|  | CTTTAAGAAGGAGATATACCATGTCCTATG(A/T)GCTGACTCAG | $V_\lambda$L-3a | 77, 78 |
|  | CTTTAAGAAGGAGATATACCATGTCCTATGAGCTGACACAG | $V_\lambda$L-3b | 79 |
|  | CTTTAAGAAGGAGATATACCATGTCTTCTGAGCTGACTCAG | $V_\lambda$L-3c | 80 |
|  | CTTTAAGAAGGAGATATACCATGTCCTATGAGCTGATGCAG | $V_\lambda$L-3d | 81 |
|  | CTTTAAGAAGGAGATATACCATGCAGC(C/T)TGTGCTGACTCAA | $V_\lambda$L-4 | 82, 83 |
|  | CTTTAAGAAGGAGATATACCATGCAG(C/G)CTGTGCTGACTCAG | $V_\lambda$L-5 | 84, 85 |
|  | CTTTAAGAAGGAGATATACCATGAATTTTATGCTGACTCAG | $V_\lambda$L-6 | 86 |
|  | CTTTAAGAAGGAGATATACCATGCAG(A/G)CTGTGGTGACTCAG | $V_\lambda$L-7 | 87, 88 |
|  | CTTTAAGAAGGAGATATACCATGCAGACTGTGGTGACCCAG | $V_\lambda$L-8 | 89 |
|  | CTTTAAGAAGGAGATATACCATGC(A/T)GCCTGTGCTGACTCAG | $V_\lambda$L-4/9 | 90, 91 |
|  | CTTTAAGAAGGAGATATACCATGAGGCAGGGCTGACTCAG | $V_\lambda$L-10 | 92 |
| primer binding in the constant region coding region | ATCGTATGGGTAGCTGGTCCCTTATGAACATTC(C/T)G(C/T)AGGGGC(A/T)ACT | $huC_\lambda$-2 | 120, 121, 122, 123, 124, 125 |

In one embodiment of the methods according to the invention the nucleic acid encoding the light chain variable domain and nucleic acid encoding the heavy chain variable domain are obtained in one polymerase chain reaction by a combination of the different 5'- and 3'-primer in a single multiplex polymerase chain reaction.

Another aspect of the current invention is a method for obtaining a nucleic acid encoding at least an immunoglobulin variable domain from a single cell comprising the following step:
performing a reverse transcription and polymerase chain reaction in one step with a set of primer comprising one 5'-primer and one 3'-primer.

In one embodiment of this method the 5'-primer employed in the multiplex one tube reverse transcription gene specific primer polymerase chain reaction (RT-GSP-PCR) binds in the coding region for the first framework region of the immunoglobulin. In another embodiment the primer employed in the RT-GSP-PCR reaction provide for overhangs encoding the translational start codon ATG for the 5'-primer and/or the translational stop codon TTA for the 3'-primer. This overhang is useful in an optional following overlapping polymerase chain reaction for the generation of nucleic acids for the in vitro translation of the obtained nucleic acid. In one embodiment this method is for obtaining an immunoglobulin heavy chain variable domain with a RT-GSP-PCR reaction. In one embodiment the immunoglobulin variable domain is an immunoglobulin heavy chain variable domain or an immunoglobulin kappa light chain variable domain or an immunoglobulin lambda light chain variable domain.

In one embodiment the primer employed in the multiplex one tube RT-GSP-PCR for obtaining a nucleic acid encoding an immunoglobulin heavy chain variable domain have the nucleic acid sequence of SEQ ID NO: 142 and 143.

TABLE 20

Primer employed in the multiplex one tube RT-GSP-PCR reaction for obtaining a nucleic acid encoding an immunoglobulin heavy chain variable domain.

| Primer description | Sequence | Denotation | SEQ ID NO: |
|---|---|---|---|
| $V_H$ primer binding in the FR1 coding region | CTTTAAGAAGGAGATATACCAT GAACTBTCTTGTCCACCTTGGT GTTG | $V_H$-lfp | 142 |
| primer binding in the constant region coding region | ATCGTATGGGTAGCTGGTCCCTT AAACTBTCTTGTCCACCTTGGTG TTG | $V_H$-rfp | 143 |

In one embodiment of the methods according to the invention the primer employed in the multiplex one tube RT-GSP-PCR for obtaining a nucleic acid encoding an immunoglobulin kappa light chain variable domain have the nucleic acid sequence of SEQ ID NO: 144 and 145.

TABLE 21

Primer employed in the multiplex one tube RT-GSP-PCR reaction for obtaining a nucleic acid encoding an immunoglobulin kappa light chain variable domain.

| Primer description | Sequence | Denotation | SEQ ID NO: |
|---|---|---|---|
| $V_\kappa$ primer binding in the FR1 coding region | CTTTAAGAAGGAGATATACCAT GACACTCTCCCCTGTTGAAGCTC | VL(k)-lfp | 144 |
| primer binding in the constant region coding region | ATCGTATGGGTAGCTGGTCCCTT AACACTCTCCCCTGTTGAAGCTC | VL(k)-rfp | 145 |

Further it has been found that with a combination of the PCR method according to the invention and a cell-free in vitro translation system the nucleic acids encoding the cognate immunoglobulin VH and VL domains can be obtained from a single cell whereby the encoded immunoglobulin variable domain is provided as Fab fragment in quantities sufficient for the characterization of the immunoglobulin's binding properties. In order to amplify the very low amount of mRNA obtained from a single cell, the individual PCR (polymerase chain reaction) has to be very sensitive and a combination of more than one PCR has to be performed.

A "cell-free in vitro translation system" according to the invention denotes a cell-free lysate of a prokaryotic or eukaryotic, preferably of a prokaryotic, cell containing ribosomes, tRNA, ATP, CGTP, nucleotides, and amino acids. In one embodiment the prokaryote is *E. coli*.

Cell-free in vitro translation is a method which has been known in the state of the art for a long time. Spirin et al. developed in 1988 a continuous-flow cell-free (CFCF) translation and coupled transcription/translation system in which a relatively high amount of protein synthesis occurs (Spirin, A. S., et al., Science 242 (1988) 1162-1164). For such cell-free in vitro translation, cell lysates containing ribosomes were used for translation or transcription/translation. Such cell-free extracts from *E. coli* were developed by, for example, Zubay (Zubay, G., et al., Ann. Rev. Genetics 7 (1973) 267-287) and were used by Pratt (Pratt, J. M., et al., Nucleic Acids Research 9 (1981) 4459-4474; and Pratt, J. M., et al., Transcription and Translation: A Practical Approach, Hames and Higgins (eds.), 179-209, IRL Press, 1984). Further developments of the cell-free protein synthesis are reported in U.S. Pat. No. 5,478,730, U.S. Pat. No. 5,571,690, EP 0 932 664, WO 99/50436, WO 00/58493, and WO 00/55353. Eukaryotic cell-free expression systems are reported by, for example, Skup, D. and Millward, S., Nucleic Acids Research 4 (1977) 3581-3587; Fresno, M., et al., Eur. J. Biochem. 68 (1976) 355-364; Pelham, H. R. and Jackson, R. J., Eur. J. Biochem. 67 (1976) 247-256 and in WO 98/31827.

It has been found that based on the amplification of nucleic acid encoding cognate IgG HC (immunoglobulin G heavy chain) and IgG LC (immunoglobulin G light chain) of an IgG isotype immunoglobulin from a single cell and the subsequent in vitro translation of the obtained nucleic acid to provide Fab fragments of said immunoglobulin a high sensitive method for obtaining information about an immunoglobulin produced by a single cell from the minute amounts of mRNA obtainable is provided. The method according to the invention permits the investigation of the expressed immunoglobulin from a single B-cell, thus, providing higher diversity as opposed to the hybridoma technology. Furthermore, since the cognate immunoglobulin variable domains or immunoglobulin chains are obtained from mature B-cells after antigen contact, selectively the nucleic acid encoding high specific and correctly assembled immunoglobulins can be obtained.

Therefore, one aspect of the current invention is a method for producing an immunoglobulin Fab fragment comprising the following steps:
  providing a single immunoglobulin producing cell,
  obtaining from the cell the nucleic acid encoding the immunoglobulin light and heavy chain variable domains, optionally also encoding a part of the light chain constant domain and a part of the heavy chain $C_H1$ domain,
  optionally generating a linear expression matrix comprising the obtained nucleic acid,
  translating in vitro the nucleic acid and thereby producing the immunoglobulin Fab fragment.

In one embodiment the nucleic acid encoding the immunoglobulin variable domains is obtained with a method according to the previous aspects of the current invention. In one embodiment of method according to the invention the obtaining the nucleic acid encoding the immunoglobulin light and heavy chain variable domain form a single cell comprises a multiplex polymerase chain reaction according to the invention for the amplification of cognate IgG HC and IgG LC (human IgG isotype) from a single B-cell. For characterization of the binding characteristics of the immunoglobulin encoded by the obtained nucleic acid the nucleic acid is subsequently translated in vitro in an *E. coli* lysate to an immunoglobulin Fab fragment.

In general one aspect of the current invention is a method employing the following steps i) isolating with magnetic micro-beads coated with the human CD19 B-cells from peripheral blood, ii) depositing single cells by limited dilution or FACS, iii) extracting the mRNA of the individualized B-cells, iv) obtaining the nucleic acid encoding at least the variable domains of the immunoglobulin produced by the individualized B-cell, v) in vitro translating the linear mRNA template, and optionally vi) characterizing the binding properties of the immunoglobulin or immunoglobulin fragment.

For the recombinant production of an immunoglobulin comprising the variable domains obtained from a single cell with a method according to the invention the obtained nucleic acids encoding the variable domain of the light and heavy immunoglobulin chain are further modified. At first the nucleic acid encoding the variable domain is combined with a nucleic acid encoding an immunoglobulin constant region. In one embodiment the nucleic acid encoding the light chain variable domain is combined with a nucleic acid encoding human kappa light chain constant domain of SEQ ID NO: 03 or with a nucleic acid encoding human lambda light chain variable domain of SEQ ID NO: 04. In another embodiment the nucleic acid encoding the heavy chain variable domain is combined with a nucleic acid encoding human immunoglobulin G1 (IgG1) constant region of SEQ ID NO: 01 or with a nucleic acid encoding human immunoglobulin G4 (IgG4) constant region of SEQ ID NO: 02. In another embodiment the nucleic acid encoding the heavy chain variable domain is combined with a nucleic acid encoding human immunoglobulin G1 (IgG1) constant region 1 ($C_H1$).

The nucleic acid molecules encoding the complete immunoglobulin heavy and light chain or a fragment thereof are in the following referred to as structural genes. They can be located on the same expression plasmid or can alternatively be located on different expression plasmids. The assembly of the immunoglobulin or Fab-fragment takes place before the secretion of the immunoglobulin to the cultivation medium and, thus, within the expressing cell. Therefore, the nucleic acid molecules encoding the immunoglobulin chains are in one embodiment expressed in the same host cell. If after recombinant expression a mixture of immunoglobulins is obtained, these can be separated and purified by methods known to a person skilled in the art. These methods are well established and widespread used for immunoglobulin purification and are employed either alone or in combination. Such methods are, for example, affinity chromatography using microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)— and Cu(II)-affinity material), size exclusion chromatography, and preparative electrophoretic methods (such as gel electrophoresis, capillary electrophoresis) (Vijayalakshmi, M. A., Appl. Biochem. Biotech. 75 (1998) 93-102).

With recombinant engineering methods known to a person skilled in the art the conjugates can be tailor-made on the nucleic acid/gene level. The nucleic acid sequences encoding immunoglobulin light and heavy chains are known and can be obtained for example from genomic databases. The elements required for the construction of an expression plasmid for the expression of the immunoglobulin obtained with a method according to the invention are, for example, an expression cassette for the immunoglobulin light chain, an expression cassette for the immunoglobulin heavy chain (alternatively the light chain and the heavy chain structural genes can be contained in the same expression cassette, e.g. as bicistronic expression element), a selection marker, and an E. coli replication as well as selection unit. An expression cassette comprises in general a promoter, a DNA segment encoding a secretion signal sequence, the structural gene, and a terminator/polyadenylation signal. The elements are assembled in an operatively linked form either on one plasmid encoding all chains of the immunoglobulin, or on two plasmids each encoding one chain of the immunoglobulin. For the expression of the structural genes the plasmid(s) is (are) introduced into a suitable host cell. Proteins are produced in mammalian cells such as CHO cells, NS0 cells, Sp2/0 cells, COS cells, HEK cells, K562 cells, BHK cells, PER.C6® cells, and the like. In one embodiment the conjugate is expressed in a CHO cell, or a BHK cell, or a HEK cell, or NS0 cell. The regulatory elements of the plasmid have to be selected in a way that they are functional in the selected host cell. For expression the host cell is cultivated under conditions suitable for the expression of the immunoglobulin, which are known to a person of skill in the art. The expressed immunoglobulin chains are functionally assembled and the fully processed immunoglobulin is secreted into the medium.

An "expression plasmid" is a nucleic acid providing all required elements for the expression of the comprised structural gene(s) in a host cell. Typically, an expression plasmid comprises a prokaryotic plasmid propagation unit, e.g. for E. coli, comprising an origin of replication, and a selectable marker, an eukaryotic selection marker, and one or more expression cassettes for the expression of the structural gene(s) of interest each comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

"Operably linked" refers to a juxtaposition of two or more components, wherein the components so described are in a relationship permitting them to function in their intended manner. The term "linking . . . in operable form" denotes the combination of two or more individual nucleic acids in a way that the individual nucleic acids are operably linked in the final nucleic acid. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as first domain and a second domain, e.g. an immunoglobulin variable domain and an immunoglobbulin constant domain or constant region, contiguous and in (reading) frame. A polyadenylation site is operably linked to a coding sequence if it is located at the downstream end of the coding sequence such that transcription proceeds through the coding sequence into the polyadenylation sequence. A translation stop codon is operably linked to an exonic nucleic acid sequence if it is located at the downstream end (3' end) of the coding sequence such that translation proceeds through the coding sequence to the stop codon and is terminated there. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

Thus, one aspect of the current invention is a method for producing an immunoglobulin comprising the following steps:

providing a single immunoglobulin producing cell, obtaining from this cell the nucleic acid encoding the immunoglobulin light and heavy chain variable domains, linking the nucleic acid encoding the light chain variable domain with a nucleic acid encoding an immunoglobulin light chain constant domain of SEQ ID NO: 03 or SEQ ID NO: 04 in operable form and linking the nucleic acid encoding the heavy chain variable domain with a nucleic acid encoding an immunoglobulin heavy chain constant region of SEQ ID NO: 01 or SEQ ID NO: 02 in operable form, transfecting a eukaryotic or prokaryotic cell with the nucleic acids of the previous step, cultivating the transfected cell under conditions suitable for the expression of the immunoglobulin, recovering the immunoglobulin from the cell or the cultivation medium and thereby producing an immunoglobulin.

The term "under conditions suitable for the expression of" denotes conditions which are used for the cultivation of a cell capable of expressing a heterologous polypeptide and which are known to or can easily be determined by a person skilled in the art. It is known to a person skilled in the art that these conditions may vary depending on the type of cell cultivated and type of polypeptide expressed. In general the cell is cultivated at a temperature, e.g. between 20° C. and 40° C., and for a period of time sufficient to allow effective production of the conjugate, e.g. for of from 4 days to 28 days, in a volume of 0.01 liter to $10^7$ liter.

The following examples, sequence listing and figures are provided to aid the understanding of the present invention, the true scope of which is set forth in the appended claims. It is understood that modifications can be made in the procedures set forth without departing from the spirit of the invention.

Description of the Sequence Listing

| | |
|---|---|
| SEQ ID NO: 01 | human IgG1 heavy chain constant region |
| SEQ ID NO: 02 | human IgG4 heavy chain constant region |
| SEQ ID NO: 03 | human IgG kappa light chain constant domain |
| SEQ ID NO: 04 | human IgG lambda light chain constant domain |
| SEQ ID NO: 05 | primer $V_HL$-1 variant 1 |
| SEQ ID NO: 06 | primer $V_HL$-1 variant 2 |
| SEQ ID NO: 07 | primer $V_HL$-2 variant 1 |
| SEQ ID NO: 08 | primer $V_HL$-2 variant 2 |
| SEQ ID NO: 09 | primer $V_HL$-3 |
| SEQ ID NO: 10 | primer $V_HL$-4 variant 1 |
| SEQ ID NO: 11 | primer $V_HL$-4 variant 2 |

| | |
|---|---|
| SEQ ID NO: 12 | primer $V_HL$-5 |
| SEQ ID NO: 13 | primer $V_HL$-6 |
| SEQ ID NO: 14 | primer $huC_H$-II variant 1 |
| SEQ ID NO: 15 | primer $huC_H$-II variant 2 |
| SEQ ID NO: 16 | primer $V_kL$-1 |
| SEQ ID NO: 17 | primer $V_kL$-2 |
| SEQ ID NO: 18 | primer $V_kL$-3 |
| SEQ ID NO: 19 | primer $V_kL$-4 |
| SEQ ID NO: 20 | primer $huC_k$-II |
| SEQ ID NO: 21 | primer $V_lL$-1 |
| SEQ ID NO: 22 | primer $V_lL$-2 |
| SEQ ID NO: 23 | primer $V_lL$-3 variant 1 |
| SEQ ID NO: 24 | primer $V_lL$-3 variant 2 |
| SEQ ID NO: 25 | primer $V_lL$-3 variant 3 |
| SEQ ID NO: 26 | primer $V_lL$-3 variant 4 |
| SEQ ID NO: 27 | primer $huC_l$-II variant 1 |
| SEQ ID NO: 28 | primer $huC_l$-II variant 2 |
| SEQ ID NO: 29 | primer $V_HL$-1a variant 1 |
| SEQ ID NO: 30 | primer $V_HL$-1a variant 2 |
| SEQ ID NO: 31 | primer $V_HL$-1b |
| SEQ ID NO: 32 | primer $V_HL$-1c variant 1 |
| SEQ ID NO: 33 | primer $V_HL$-1c variant 2 |
| SEQ ID NO: 34 | primer $V_HL$-1d variant 1 |
| SEQ ID NO: 35 | primer $V_HL$-1d variant 2 |
| SEQ ID NO: 36 | primer $V_HL$-2a |
| SEQ ID NO: 37 | primer $V_HL$-2b variant 1 |
| SEQ ID NO: 38 | primer $V_HL$-2b variant 2 |
| SEQ ID NO: 39 | primer $V_HL$-3a variant 1 |
| SEQ ID NO: 40 | primer $V_HL$-3a variant 2 |
| SEQ ID NO: 41 | primer $V_HL$-3b |
| SEQ ID NO: 42 | primer $V_HL$-3c |
| SEQ ID NO: 43 | primer $V_HL$-4a variant 1 |
| SEQ ID NO: 44 | primer $V_HL$-4a variant 2 |
| SEQ ID NO: 45 | primer $V_HL$-4b |
| SEQ ID NO: 46 | primer $V_HL$-5a variant 1 |
| SEQ ID NO: 47 | primer $V_HL$-5a variant 2 |
| SEQ ID NO: 48 | primer $V_HL$-6a |
| SEQ ID NO: 49 | primer $V_HL$-7a variant 1 |
| SEQ ID NO: 50 | primer $V_HL$-7a variant 2 |
| SEQ ID NO: 51 | primer $huC_H$-III variant 1 |
| SEQ ID NO: 52 | primer $huC_H$-III variant 2 |
| SEQ ID NO: 53 | primer $V_kL$-1a variant 1 |
| SEQ ID NO: 54 | primer $V_kL$-1a variant 2 |
| SEQ ID NO: 55 | primer $V_kL$-1b variant 1 |
| SEQ ID NO: 56 | primer $V_kL$-1b variant 2 |
| SEQ ID NO: 57 | primer $V_kL$-1c variant 1 |
| SEQ ID NO: 58 | primer $V_kL$-1c variant 2 |
| SEQ ID NO: 59 | primer $V_kL$-1d |
| SEQ ID NO: 60 | primer $V_kL$-2a |
| SEQ ID NO: 61 | primer $V_kL$-2b variant 1 |
| SEQ ID NO: 62 | primer $V_kL$-2b variant 2 |
| SEQ ID NO: 63 | primer $V_kL$-3a variant 1 |
| SEQ ID NO: 64 | primer $V_kL$-3a variant 2 |
| SEQ ID NO: 65 | primer $V_kL$-3b |
| SEQ ID NO: 66 | primer $V_kL$-3c |
| SEQ ID NO: 67 | primer $V_kL$-4a |
| SEQ ID NO: 68 | primer $V_kL$-5a |
| SEQ ID NO: 69 | primer $V_kL$-6a |
| SEQ ID NO: 70 | primer $V_kL$-6b |
| SEQ ID NO: 71 | primer $huC_k$-III |
| SEQ ID NO: 72 | primer $V_lL$-1a |
| SEQ ID NO: 73 | primer $V_lL$-1b variant 1 |
| SEQ ID NO: 74 | primer $V_lL$-1b variant 2 |
| SEQ ID NO: 75 | primer $V_lL$-1c |
| SEQ ID NO: 76 | primer $V_lL$-2a |
| SEQ ID NO: 77 | primer $V_lL$-3a variant 1 |
| SEQ ID NO: 78 | primer $V_lL$-3a variant 2 |
| SEQ ID NO: 79 | primer $V_lL$-3b |
| SEQ ID NO: 80 | primer $V_lL$-3c |
| SEQ ID NO: 81 | primer $V_lL$-3d |
| SEQ ID NO: 82 | primer $V_lL$-4 variant 1 |
| SEQ ID NO: 83 | primer $V_lL$-4 variant 2 |
| SEQ ID NO: 84 | primer $V_lL$-5 variant 1 |
| SEQ ID NO: 85 | primer $V_lL$-5 variant 2 |
| SEQ ID NO: 86 | primer $V_lL$-6 |
| SEQ ID NO: 87 | primer $V_lL$-7 variant 1 |
| SEQ ID NO: 88 | primer $V_lL$-7 variant 2 |
| SEQ ID NO: 89 | primer $V_lL$-8 |
| SEQ ID NO: 90 | primer $V_lL$-4/9 variant 1 |
| SEQ ID NO: 91 | primer $V_lL$-4/9 variant 2 |
| SEQ ID NO: 92 | primer $V_lL$-10 |
| SEQ ID NO: 93 | primer $huC_l$-III |
| SEQ ID NO: 94 | primer $huV_H$1 |
| SEQ ID NO: 95 | primer $huV_H$2 |
| SEQ ID NO: 96 | primer $huV_H$3 variant 1 |
| SEQ ID NO: 97 | primer $huV_H$3 variant 2 |
| SEQ ID NO: 98 | primer $huV_H$3 variant 3 |
| SEQ ID NO: 99 | primer $huV_H$3 variant 4 |
| SEQ ID NO: 100 | primer $huV_H$4 variant 1 |
| SEQ ID NO: 101 | primer $huV_H$4 variant 2 |
| SEQ ID NO: 102 | primer $huV_H$4 variant 3 |
| SEQ ID NO: 103 | primer $huV_H$4 variant 4 |
| SEQ ID NO: 104 | primer $huC_H$2 variant 1 |
| SEQ ID NO: 105 | primer $huC_H$2 variant 2 |
| SEQ ID NO: 106 | primer $huC_H$2 variant 3 |
| SEQ ID NO: 107 | primer $huV_k$-1 variant 1 |
| SEQ ID NO: 108 | primer $huV_k$-1 variant 2 |
| SEQ ID NO: 109 | primer $huV_k$-1 variant 3 |
| SEQ ID NO: 110 | primer $huV_k$-1 variant 4 |
| SEQ ID NO: 111 | primer $huV_k$-2 variant 1 |
| SEQ ID NO: 112 | primer $huV_k$-2 variant 2 |
| SEQ ID NO: 113 | primer $huV_k$-3 |
| SEQ ID NO: 114 | primer $huV_k$-4 |
| SEQ ID NO: 115 | primer $huC_k$-2 |
| SEQ ID NO: 116 | primer $huV_l$1 |
| SEQ ID NO: 117 | primer $huV_l$2 |
| SEQ ID NO: 118 | primer $huV_l$3 variant 1 |
| SEQ ID NO: 119 | primer $huV_l$3 variant 2 |
| SEQ ID NO: 120 | primer $huC_l$2 variant 1 |
| SEQ ID NO: 121 | primer $huC_l$2 variant 2 |
| SEQ ID NO: 122 | primer $huC_l$2 variant 3 |
| SEQ ID NO: 123 | primer $huC_l$2 variant 4 |
| SEQ ID NO: 124 | primer $huC_l$2 variant 5 |
| SEQ ID NO: 125 | primer $huC_l$2 variant 6 |
| SEQ ID NO: 126 | primer LTGS-lfp |
| SEQ ID NO: 127 | primer LTGS-rfp |
| SEQ ID NO: 128 | primer $V_H$1a |
| SEQ ID NO: 129 | primer $V_H$1b |
| SEQ ID NO: 130 | primer $V_H$1c |
| SEQ ID NO: 131 | primer $V_H$1d |
| SEQ ID NO: 132 | primer $V_H$2a |
| SEQ ID NO: 133 | primer $V_H$2b |
| SEQ ID NO: 134 | primer $V_H$3a |
| SEQ ID NO: 135 | primer $V_H$3b |
| SEQ ID NO: 136 | primer $V_H$3c |
| SEQ ID NO: 137 | primer $V_H$4a |
| SEQ ID NO: 138 | primer $V_H$4b |
| SEQ ID NO: 139 | primer $V_H$5a |
| SEQ ID NO: 140 | primer $V_H$6a |
| SEQ ID NO: 141 | primer $V_H$7a |
| SEQ ID NO: 142 | primer $V_H$-lfp |
| SEQ ID NO: 143 | primer $V_H$-rfp |
| SEQ ID NO: 144 | primer VL(k)-lfp |
| SEQ ID NO: 145 | primer VL(k)-rfp |

EXAMPLES

Figure 1A:
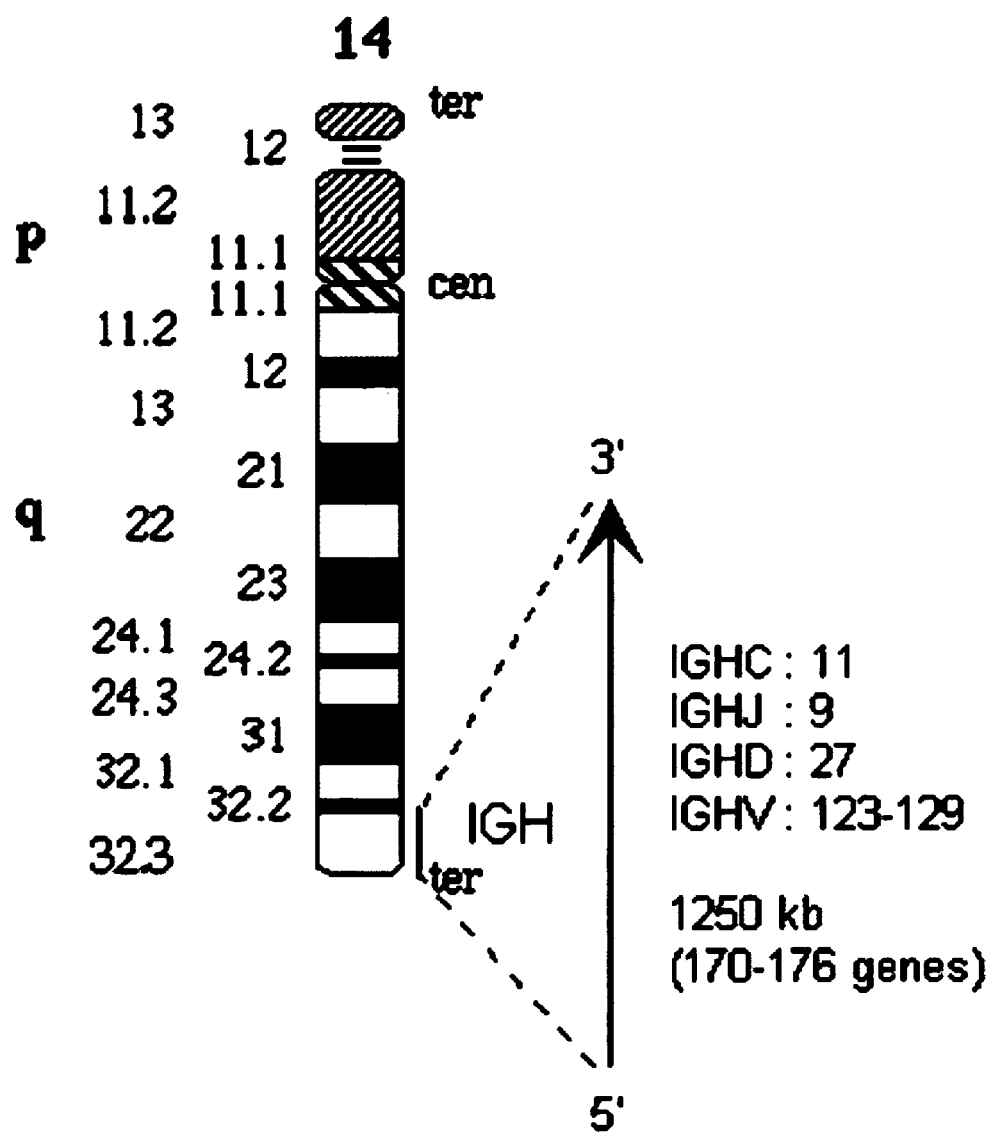
FIG. 1 Chromosomal localization of the human immunoglobulin G heavy chain locus (A), the human immunoglobulin kappa light chain locus (B) and of the human immunoglobulin lambda light chain locus (C).
Figure 1B:
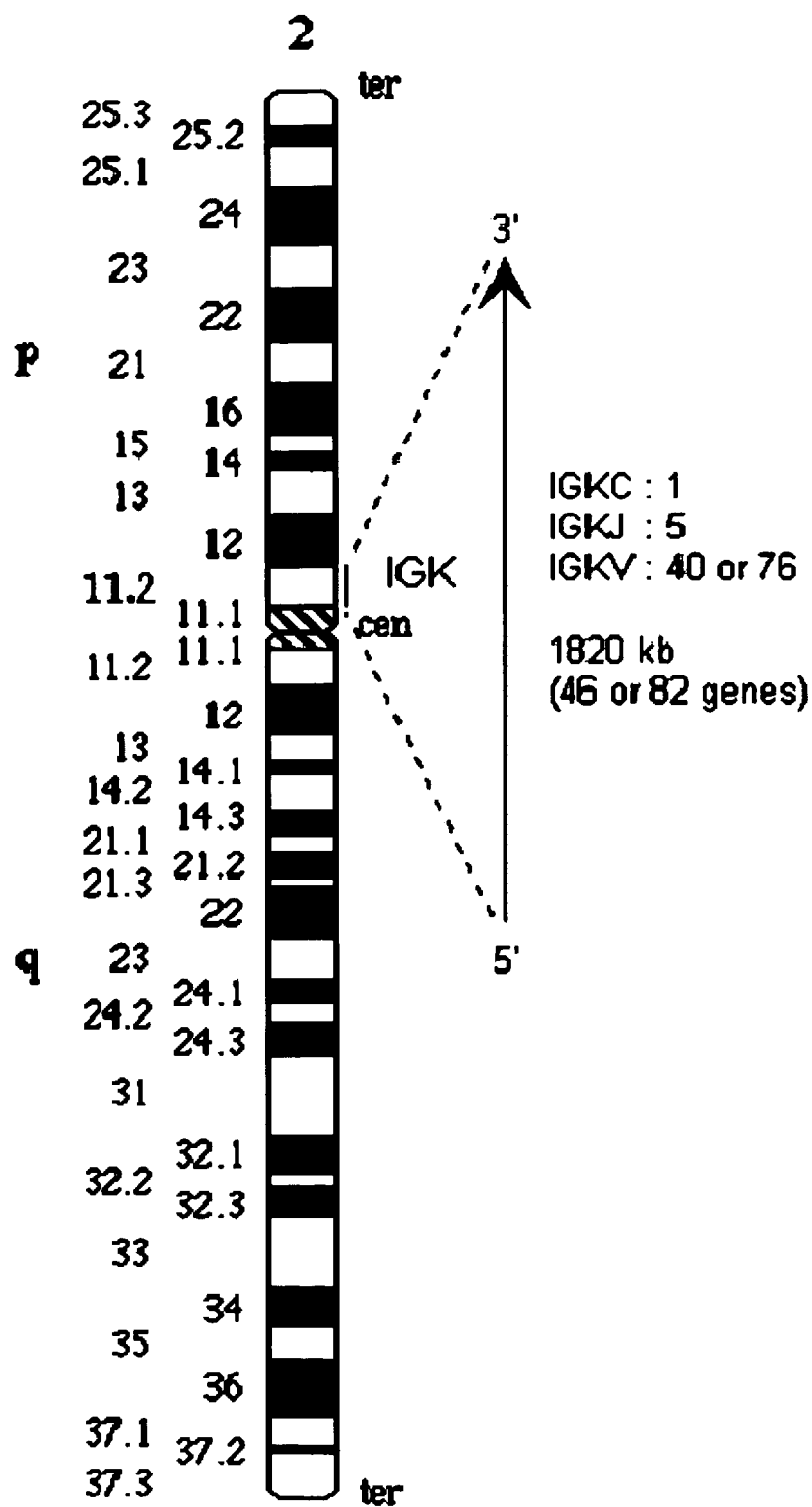
Figure 1C:
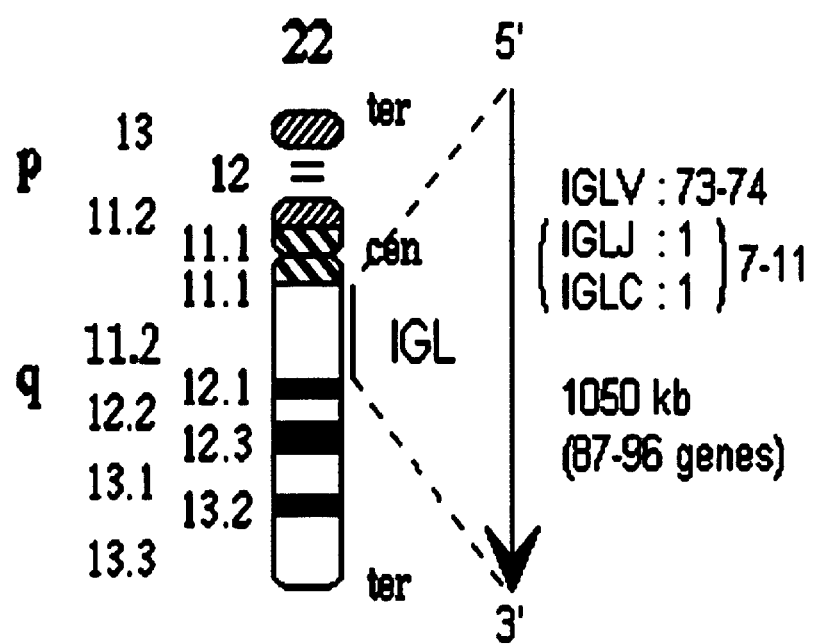

Materials & Methods
B-Cells and Plasma Cells

Samples used in this approach are B-cells and plasma cells isolated from the peripheral blood of healthy donor and tissue (spleen, bone marrow) of transgenic mice for human IgG. Solid tissue is first of all manually disaggregated in DMEM in separate tubes. In the later steps, gentle handling and low temperature minimize cell lysis, which is important for the future positive isolation of the cells of interest and to keep the source of mRNA intact. Disaggregated tissue is suspended by the delicate addition of cell separation media for making of a different cell type gradient (Leucosep-tubes (Greiner Bio-One) with Ficoll density gradient). Suspended cells are purified by centrifugation on the cold separation medium for 20 min. at 800×g and 22° C. in a centrifuge without breaking in order to enrich for plasma cells (PBMC) and lymphocytes. Cells are washed in cold buffer (PBS (phosphate buffered saline), 0.1% (w/v) BSA (bovine serum albumin), 2 mM EDTA (ethylene diamin tetra acetate)) and the supernatant is carefully discarded to keep only the lymphocytes. Lymphocytes are than resuspended in PBS and mixed by carefully pipetting. Centrifugation is effectuated for 5 min. at 800×g and 22° C. to pellet the cells. B-cells and plasma cells are pretreated with murine and human FC blocker to block unspecific binding of Abs on their cells surface. Cells are washed once with buffer (PBS, 0.1% (w/v) BSA, 2 mM EDTA), centrifuged and resuspended in PBS. Only the CD19+ B-cells and CD138+ plasma cells were used. To prevent mRNA degradation an RNAse Inhibitor is added. The positive isolation of the CD19+ B-cells (Dynal Biotech Dynabeads CD19 Pan B) from the mouse spleen has been carried out according to the manufacturer's instructions. The selection of the CD138+ plasma cells (StemCell Technologies EasySep Human CD138 Selection Kit) has been carried out following the manufacturer's instructions.

Separation into Single Cell by the Principle of the Limiting-Dilution Culture or FACS Sorting:

Cells are counted and, by the principle of the limiting-dilution culture, deposited as single cell into the wells of 96-well PCR plates or 384-well plates. Plates are sealed with PCR Film and immediately placed on ice. Sorted cells can be used immediately in RT-PCR (reverse transcriptase polymerase chain reaction) or stored at −20° C. for short-term use or −80° C. for long-term use. Single-cell sorting was performed on a FACSAria cell-sorting system (Becton Dickinson). Cells that stained positive for CD19, highly positive for CD38 and intermediately positive for CD45 were collected and designated plasma cells (PC). Additional gates on forward scatter/side scatter and side scatter width/side scatter height were included to select live lymphocytes and singlets, respectively. Single cells were distributed directly into the wells of 96-well PCR plates (Eppendorf), containing all the necessary PCR reagents in a volume of 10 μl, except for reverse transcriptase, DNA polymerase, buffer and dNTPs and frozen at −80° C. for later processing.

Cell Lysis and Reverse Transcription:

To be able to amplificate the mRNA in a polymerase chain reaction, B-cells and plasma cells must be lysed before the reverse transcription reaction.

TABLE 22

Components used for the classical lysis.

| Component | Volume (μl) | Final concentration |
|---|---|---|
| Water, PCR grade | 1.75 | |
| 5xRT Reaction Buffer | 1.00 | |
| RNAse Inhibitor (40 U/μl) | 0.25 | 5 U |
| Gene Specific antisense primer | 1.00 | 0.02 μM |
| Igepal 0.01% | 1.00 | 0.01% |
| Final volume | 5.00 | |

TABLE 23

Block cycler program for the cell lysis.

| Temperature (° C.) | Time (sec) |
|---|---|
| 65 | 60 |
| 55 | 30 |
| 45 | 30 |
| 35 | 20 |
| 23 | 120 |
| 4 | ∞ |

Plates with lysed cells are spun briefly in the centrifuge for 30 sec. to collect liquid and cells in the bottom of wells. The RT (reverse transcriptase) reaction as well as all the PCR reaction was made in a 96-well plate. To each well containing 5 μl template is added 2.5 μl of water, 1 μl cold RT reaction buffer, 1 μl dNTPs, 0.25 μl RNAse Inhibitor (40 U/μl), 0.25 μl reverse transcriptase (20 U/μl), all from the First Strand cDNA Synthesis Kit (Roche Diagnostics GmbH, Mannheim, Germany) for a total volume of 10 μl. RT plates are briefly centrifuged and placed from ice to 55° C. for 60 min. (with heated lid), heated to 85° C. for 2 min. (to inactivate the reverse transcriptase), in a Block cycler (LightCycler 480, Roche Diagnostics GmbH, Mannheim, Germany). Single-stranded cDNA was stored at −20° C. shortly after the reverse transcription reaction to avoid degradation of the cDNA. A control synthesis reaction was simultaneously performed without cells to test for contamination.

TABLE 24

Components used for the reverse transcription reaction.

| Component | Volume (μl) | Final concentration |
|---|---|---|
| Water, PCR grade | 6.8 | |
| PCR Master | 10 | |
| Semi-nested Primer IgG HC | 0.4 | 0.02 μM |
| Semi-nested Primer IgG LC (k) | 0.4 | 0.02 μM |
| Semi-nested Primer IgG LC (l) | 0.4 | 0.02 μM |
| cDNA template from RT reaction | 2 | |
| Final volume | 20 | |

Cell Lysis and Reverse Transcription:

To be able to amplificate the mRNA in a polymerase chain reaction, B-cells and plasma cells must be lysed before the reverse transcription reaction.

First PCR:

TABLE 25

Block cycler program for the first PCR.

| Temperature (° C.) | Time | Number of cycles |
|---|---|---|
| 95 | 2 min. | 1 |
| 94 | 15 sec. | 35 |
| 55 | 30 sec. | |
| 72 | 1 min. | |
| 72 | 10 min. | 1 |
| 4 | ∞ | |

TABLE 26

Primer used for the first PCR.

| Ig heavy chain primer | Ig light chain (κ) primer | Ig light chain (λ) primer |
|---|---|---|
| $V_H$L-1 | $V_\kappa$L-1 | $V_\lambda$L-1 |
| $V_H$L-2 | $V_\kappa$L-2 | $V_\lambda$L-2 |
| $V_H$L-3 | $V_\kappa$L-3 | $V_\lambda$L-3 |
| $V_H$L-4 | $V_\kappa$L-4 | $huC_\lambda$-II |
| $V_H$L-5 | $huC_\kappa$-II | |
| $V_H$L-6 | | |
| $huC_H$-II | | |

Second PCR:

The κ and λ light chains and the heavy chains were subsequently amplified with a second-round PCR according to the following protocol. Using semi-nested primer, the second PCR was performed to increase the amount of cDNA copies and to amplify only from the variable part of the light chain (LC) and heavy chain (HC) to the $C_H1$ region. The HC amplification was performed using 16 primer, the kappa LC using 17 primer, and the lambda LC using 14 primer. The genes were amplified in a total volume of 20 μl using 2 μl of the first PCR product, 10 μl of High Fidelity PCR Master (containing 0.4 μM each dNTPs, double concentrated reaction buffer (with 3 mM $MgCl_2$), 0.02 μM of each primer, all from the High Fidelity PCR Master Kit (Roche Diagnostics GmbH, Mannheim, Germany) using the following second PCR program: 2 min. at 95° C., 45 cycles of 94° C. for 15 sec., 55° C. for 30 sec., 72° C. for 1 min., following 10 min. at 72° C.

TABLE 27

Components used for the second PCR.

| Component | Volume (μl) | Final concentration |
|---|---|---|
| Water, PCR grade | 7.8 | |
| High Fidelity PCR Master | 10 | 1.8 mM $MgCl_2$ |
| Two-step Primer IgG HC | 0.4 | 0.02 μM |
| Two-step Primer IgG LC(κ) | 0.4 | 0.02 μM |
| Two-step Primer IgG LC(λ) | 0.4 | 0.02 μM |
| First PCR product | 2 | |
| Final volume | 20 | |

TABLE 28

Block cycler program for the second PCR.

| Temperature (° C.) | Time | Number of cycles |
|---|---|---|
| 95 | 2 min. | 1 |
| 94 | 15 sec. | 45 |
| 55 | 30 sec. | |
| 72 | 1 min. | |
| 72 | 10 min. | 1 |
| 4 | ∞ | |

TABLE 29

Primer used for the second PCR

| IgG heavy chain primer | IgG light chain (κ) primer | IgG light chain (λ) primer |
|---|---|---|
| $V_H$1a | $V_\kappa$1a | $V_\lambda$1a |
| $V_H$1b | $V_\kappa$1b | $V_\lambda$1b |
| $V_H$1c | $V_\kappa$1c | $V_\lambda$1c |
| $V_H$1d | $V_\kappa$1d | $V_\lambda$2 |
| $V_H$2a | $V_\kappa$2a | $V_\lambda$3a |
| $V_H$2b | $V_\kappa$2b | $V_\lambda$3b |
| $V_H$3a | $V_\kappa$3a | $V_\lambda$3c |
| $V_H$3b | $V_\kappa$3b | $V_\lambda$3d |
| $V_H$3c | $V_\kappa$3c | $V_\lambda$4 |
| $V_H$4a | $V_\kappa$4a | $V_\lambda$5 |
| $V_H$4b | $V_\kappa$5a | $V_\lambda$6 |
| $V_H$5a | $V_\kappa$6a | $V_\lambda$7 |
| $V_H$6a | $V_\kappa$6b | $V_\lambda$8 |
| $V_H$7a | $C_\kappa$III | $V_\lambda$4/9 |
| $C_H$III | | $V_\lambda$10 |
| | | $C_\lambda$III |

One Step Multiplex RT-GSP (Gene Specific Primer)-PCR Reaction:

To be able to amplificate the mRNA in a polymerase chain reaction, B-cells and plasma cells must be distributed directly into the wells of 96-well PCR plates (Eppendorf), containing all the necessary PCR reagents in a volume of 10 µl, except for reverse transcriptase, DNA polymerase, buffer and dNTPs and frozen at −80° C. for later processing.

RT-Step:

Reverse transcription and PCR were performed in one step (one step Multiplex RT-PCR). The isolated, sorted and stored cells were used as raw material for the reverse transcription or RT-PCR. All necessary reagents were thawed at room temperature. All primer were synthesized in the MOLBIOL TIB GmbH laboratories. The plates and all other reagents were kept on ice during the entire procedure. For cDNA syntheses the gene specific primer with extensions were used directly. The enzyme complex consists of two Sensiscript reverse transcriptases and one Omniscript polymerase (Qiagen OneStep RT PCR). The rewriting of the mRNA into cDNA was performed by the Sensiscript complex (Qiagen OneStep RT PCR) and the amplification of the cDNA was performed using the HotStarTaq DNA Polymerase (Qiagen OneStep RT PCR), which is a chemically form of a recombinant 94 kDa DNA polymerase (deoxynucleoside-triphosphate: DNA deoxynucleotidyltransferase, EC 2.7.7.7), originally isolated from *Thermus aquaticus* expressed in *E. coli*. The cells were sorted in a 96-well PCR plate and stored in a volume of 10 containing 5 µl PCR H$_2$O grade, 1µ10.1 µM primer for VH and VL, 1 µl RNAse inhibitor 20 U/reaction and 3 µl Tris 1.5 mM. Before adding the other 10 µl for performing the PCR reaction, the cells stored at −60° C. were briefly centrifuged (20 sec. at 1400 rpm) to collect the liquid and cells on the bottom of the wells.

TABLE 30

Master Mix 1 used for the RT-PCR.

| Master Mix 1 | Final concentration/well | volume/well (µl) |
|---|---|---|
| H$_2$O | | 5 |
| primer $V_H$/VL(k) | 0.1 µM | 1 |
| RNAse Inhibitor | 20 U/reaction | 1 |
| Tris-buffer | 1.5 mM | 3 |
| B/Plasma cells | | |
| final volume | | 10 |

TABLE 31

Master Mix 2 used for the RT-PCR.

| Master Mix 2 | Final concentration/well | volume/well (µl) |
|---|---|---|
| H$_2$O | 1x | 2.2 |
| 5x Buffer | 1x | 4 |
| dNTP 10 mM each | 400 µM each | 0.8 |
| 5x Q-Solution | 0.25x | 1 |
| One Step RT PCR Enzyme mix | | 1.2 |
| RNAse Inhibitor | 20U | 1 |
| final volume | | 10 |

10 µl per well of Master Mix 2 were added to the cells. The second Master Mix contained 2.2 µl H$_2$O PCR grade, 4 µl of 1× buffer, 0.8 µl of dNTPs 400 µM each, 1 µl of Q-solution 0.25×, 1.2 µl of the enzyme complex and 1 µl of RNAse inhibitor 20U.

TABLE 32

Primer used for the RT-PCR.

| Ig heavy chain primer | | Ig light chain (κ) primer | |
|---|---|---|---|
| $V_H$-lfp | SEQ ID NO: 142 | VL(k)-lfp | SEQ ID NO: 144 |
| $V_H$-rfp | SEQ ID NO: 143 | VL(k)-rfp | SEQ ID NO: 145 |

TABLE 33

Block cycler program for the RT-GSP-PCR.

| Temperature | Time | Step | Cycles |
|---|---|---|---|
| 50° C. | 30 min. | reverse transcription | 1 |
| 95° C. | 15 min. | denaturation | 1 |
| 94° C. | 40 sec. | denaturation | 11 |
| 52° C. | 1 min. | annealing | |
| 72° C. | 1 min. | elongation | |
| 94° C. | 41 sec. | denaturation | 29 |
| 60° C. | 1 min. | annealing | |
| 72° C. | 1 min. | elongation | |
| 72° C. | 10 min. | final elongation | 1 |
| 4° C. | ∞ | cooling | |

Purification of PCR Products:

To improve the efficiency of the generation of linear template for the in vitro translation in the next overlapping PCR (third PCR) the purification of the previously amplified PCR products was performed by removing unincorporated primer, dNTPs, DNA polymerases and salts used during PCR amplification in order to avoid interference in downstream applications. Agencourt AMPure was used. The buffer is optimized to selectively bind PCR amplicons 100 bp and larger to paramagnetic beads. Excess oligonucleotides, nucleotides, salts, and enzymes can be removed using a simple washing procedure. The resulting purified PCR product is essentially free of contaminants and can be used in the following applications: Fluorescent DNA sequencing (including capillary electrophoresis), microarray spotting, cloning and primer extension genotyping. The work flow for 96-well format started with gently shaking the beads stored in buffer to resuspend any magnetic particle that may have settled. The correct volume of 36 µl of beads solution was added to the 20 µl of sample and the mix was pipetted 10 times up and down. The following step was incubating for 10 minutes and afterwards the reaction plate was placed onto a magnetic plate for 10 minutes to separate beads from solution. The cleared solution (supernatant) was aspirated from the reaction plate and discard. For the beads-cDNA washing 200 µl of 70% ethanol were dispersed per well and incubated at room temperature for at least 30 seconds. The ethanol was aspirated out and discarded. The washing step was performed two times and then the reaction plate was left to air-dry for 20 minutes at room temperature. It followed with the addition of 40 µl of elution buffer and the mix was again pipetted 10 times up and down. After the cDNA dissociation from the magnetic beads, the purified DNA was transferred into a new plate.

Third PCR:

The amplified DNA of the second PCR was afterwards linked by an overlapping extension PCR method with the following components, necessary for the transcription/translation step: a ribosome binding site (RBS), a T7 promoter and a T7 terminator sequences. For this PCR, 2 µl of the second PCR were taken to a final volume of 20 µl containing: 10.7 µl water, 2 µl of 10× reaction buffer with MgCl$_2$ (10 mM), 0.8 µl of DMSO, 0.5 µl dNTPs (10 mM each), 1.6 µl T7 promotor and terminator primer (6 µM each), 0.4 µl C-terminal HA-Tag primer and 0.4 µl of enzyme blend, all from the RTS *E. coli* Linear Template Generation Set, HA-Tag (Roche Diagnostics GmbH, Mannheim, Germany). Finally, the overlapping PCR products were used as template for in vitro transcription using *Escherichia coli* lysate and the resulting functional Fab was screened against the F(ab')$_2$ IgG by enzyme-linked immunoadsorbent assay (ELISA).

TABLE 34

Components used for the third PCR.

| Component | Volume (µl) | Final concentration |
|---|---|---|
| Water, PCR grade | 10.7 | |
| 10× Reaction Buffer with MgCl$_2$ (10 mM) | 2 | 1× |
| DMSO | 0.8 | |
| PCR Nucleotide mix (10 mM each) | 0.5 | 250 µM |
| Working solution T7 Prom Primer (6 µM) | 1.6 | 0.48 µM |
| Working solution T7 Term Primer (6 µM) | 1.6 | 0.48 µM |
| Working solution C-term HA-tag (6 µM) | 0.4 | 0.48 µM |
| Enzyme Blend | 0.4 | |
| PCR 2 product | 2 | |
| Final volume | 20 | |

TABLE 35

Block cycler program for the third PCR.

| Temperature (° C.) | Time | Number of cycles |
|---|---|---|
| 95 | 4 min. | 1 |
| 95 | 1 min. | 45 |
| 60 | 1 min. | |

TABLE 35-continued

Block cycler program for the third PCR.

| Temperature (° C.) | Time | Number of cycles |
|---|---|---|
| 72 | 1 min. 30 sec. | |
| 72 | 7 min. | 1 |
| 4 | ∞ | |

Gel Electrophoresis:

The gel electrophoresis analysis (1% agarose gel, Invitrogen Corp., USA) was performed to evaluate the amplification and the specificity of the cDNA templates with the appropriate controls.

TABLE 36

Gel analysis protocol.

| Component | Volume (µl) | Migration time |
|---|---|---|
| H$_2$O | 6 | |
| 5× Orange G | 3 | |
| PCR product | 6 | |
| Final volume | 15 | |
| Volume for gel | 10 | 20 min. |

In Vitro Transcription and Translation:

The in vitro coupled transcription and translation was carried out following the manufacturer's protocol RTS100 *E. coli* Disulfide Kit (Roche Diagnostics GmbH, Mannheim, Germany) with components as reported (see Table 12). 4 µl of each overlapping PCR product was transcribed and translated in a total volume of 50 µl, at 37° C. for 20 hours in the RTS Proteo Master Instrument (Roche Diagnostics GmbH, Mannheim, Germany). A control reaction was performed under identical conditions without cDNA template. GFP (green fluorescent protein) vectors were added to the reaction system for autoradiography as positive control. After the in vitro transcription/translation, the 50 µl reaction mixture was transferred in 75 µl PBS (1:2.5 dilution) and incubated at 4° C. overnight for the correct folding and maturation of the protein.

TABLE 37

Components for the in vitro transcription and translation.

| Mix | Component | Volume (µl) |
|---|---|---|
| Mix 1: | *E. coli* lysate | 25 |
| | Lysate activator | 1 |
| | Final volume | 26 |
| | incubate for 10-20 min. at RT | |
| Mix 2: | Feeding mix | 640 |
| | Amino acid mix | 140 |
| | Methionine | 20 |
| | H$_2$O | 200 |
| | Final volume | 1000 |
| Mix 3: | Reaction mix | 7 |
| | Amino acid mix | 7 |
| | Methionine | 1 |
| | Mix 1 | 25 |
| | GroE Supplement | 5 |
| | RNAse inhibitor | 1 |
| | PCR 3 product | 4 |
| | Final volume | 50 |

ELISA:

A 384-well plate (Nunc GmbH & Co. KG, Thermo Fisher Scientific, Langenselbold, Germany) was coated with 50 µl (1:1000 in PBS) goat anti-human IgG Fab fragment (produced by Bethyl Laboratories Inc., obtained from Biomol GmbH, Hamburg, Germany, 1 mg/1 ml) incubated at 4° C. overnight. The plate was washed three times with washing solution (100 µl PBST (phosphate buffered saline Tween-20)) and 60 µl of Blocking solution (0.25% CroteinC (w/v)/0.5% Tween (w/v)/PBS) was added, incubated for 1 h at room temperature. Another washing step (3×100 µl PBST) was performed and 37.5 µl sample was transferred, as well as 37.5 ml negative control (negative control from the in vitro transcription/translation) and 37.5 µl positive control, containing 0.75 µl of human recombinant Fab fragment (Roche Diagnostics GmbH, Mannheim, Germany). The samples were titrated to a 1:3 dilution. The plate was incubated for 1.5 h at room temperature. After a washing step (3×100 µl PBST), 25 µl goat anti-human IgG F(ab')$_2$ (Dianova, Hamburg, Germany; 0.8 mg/ml (1:2000 diluted in Blocking Solution)) was added and incubated for 1 h at room temperature. The last washing step (3×100 µl PBST) was performed and 25 µl of TMB (POD Substrate, Roche Diagnostics GmbH, Mannheim, Germany, Art-No: 1 484 281) was pipetted into each well. After 2-3 minutes the absorption signal was detected at 405 nm and 495 nm (Tecan, Safire 2; Tecan Deutschland GmbH, Crailsheim, Germany).

Flow Cytometric Analysis and Cell Sorting:

For FACS analysis and cell sorting monoclonal antibodies, either biotinylated or conjugated with either FITC (fluorescein isothiocyanate), PE (Phycoerythrin), or APC (allophycocyanin) against the following antigens were used: CD3 (UCHT1), CD4 (13B8.2), CD8 (B9.11), CD40 (MAB89), CD80 (MAB104), CD83 (HB15a), CD86 (HA5.2B7) (all available from Immunotech/Beckman Coulter, Marseille, France), CD19 (HIB19), CD20 (2H7), CD34 (581), IL-3Ra/CD123 (9F5), CD11c (B-ly6) CD14 (M5E2), CD24, CD22a, CD38, CD138 (all available from BD Pharmingen, San Diego, Calif., USA), CD45 (HI30), CD45RA (MEM56), HLA-DR (TU36) (all available from Caltag, Burlingame, Calif., USA), TLR2 (TL2.1), TLRR4 (HTA125), TCRab (IP26), (all available from Bioscience, San Diego, Calif.), BDCA-1, BDCA-2, BDCA-4, CD25 (4E3) (all available from Miltenyi Biotec, Bergisch Gladbach, Germany), IgM (Jackson Immunoresearch, West Grove, Pa., USA), CCR7 (3D12, provided by M. Lipp, Berlin, Germany). The IOTest Beta Mark was used for Vb analysis (Immunotech/Beckman Coulter). Streptavidin conjugated FITC, PE, or APC (all BD Pharmingen) were used for visualization of biotinylated antibodies. Dead cells were excluded by propidium iodide staining. Appropriate isotype-matched, irrelevant control mAbs were used to determine the level of background staining. Cells were analyzed using a FACS Calibur and sorted using a FACSAria (Becton Dickinson Immunocytometry Systems, Mountain View, Calif., USA).

Example 1

Figure 2:
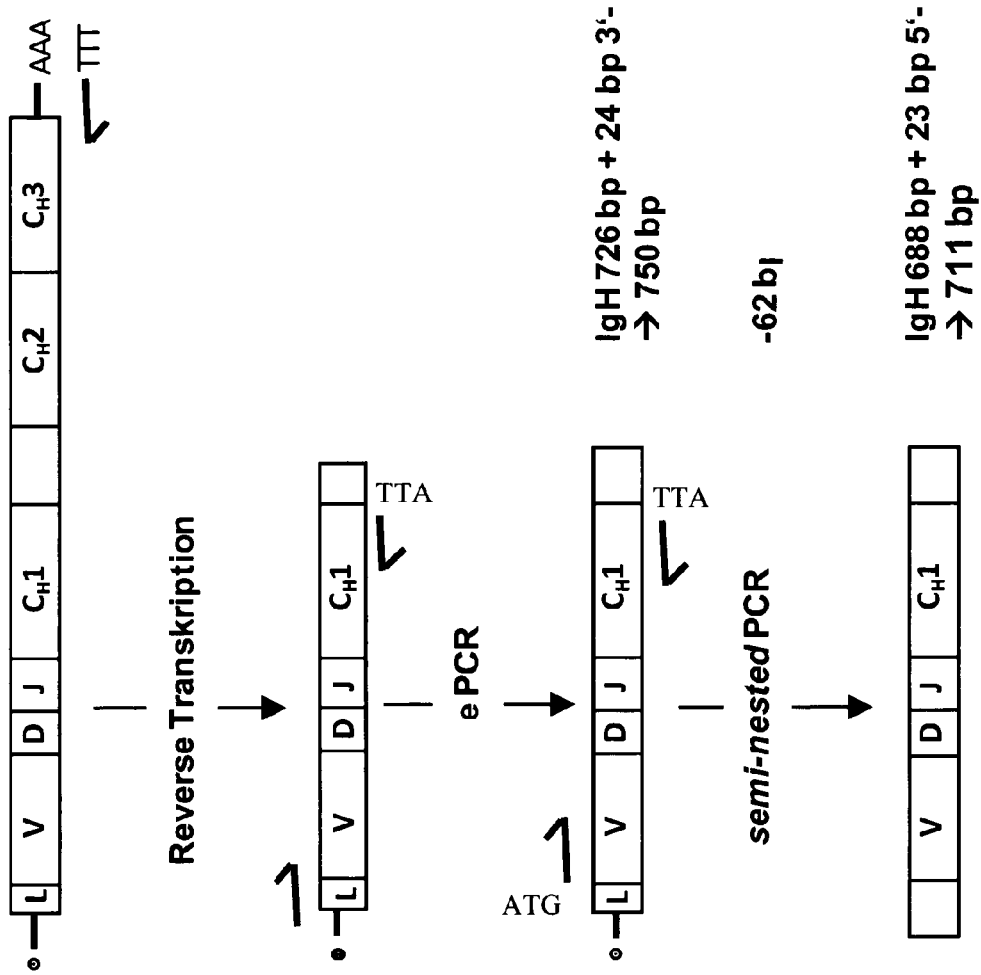
FIG. 2 Scheme for the polymerase chain reaction for the immunoglobulin light chain with a first and a second primer set.

Amplification of IgG Genes from Humanized Immunized Mice's Single B Cell by a Polymerase Chain Reaction with One Fixed Primer Set and One Changed Primer Set Single B-cells of a mouse having a human immunoglobulin locus have been obtained as outlined above. The 3'-primer of the first and second primer set employed in the polymerase chain reaction were identical. The 5'-primer of the first and second primer set different insofar as the primer of the first 5'-primer set bound in the region encoding the leader peptide and the primer of the second 5'-primer set bound in the FR1 region. A scheme of this polymerase chain reaction is given in FIG. 2.

The employed sets of primer for the first polymerase chain reaction are denoted in the following list:

| Ig heavy chain primer | Ig light chain (κ) primer | Ig light chain (λ) primer |
|---|---|---|
| VHL-1 | V$_κ$L-1 | V$_λ$L-1 |
| V$_H$L-2 | V$_κ$L-2 | V$_λ$L-2 |
| V$_H$L-3 | V$_κ$L-3 | V$_λ$L-3 |
| V$_H$L-4 | V$_κ$L-4 | huC$_λ$-II |
| VHL-1 | V$_κ$L-1 | V$_λ$L-1 |
| V$_H$L-5 | huC$_κ$-II | |
| V$_H$L-6 | | |
| huC$_H$-II | | |

The employed sets of primer for the second polymerase chain reaction are denoted in the following list:

| IgG heavy chain primer | | IgG light chain (κ) primer | | IgG light chain (λ) primer | |
|---|---|---|---|---|---|
| V$_H$-1a | SEQ ID NO: 128 | V$_κ$L-1a | SEQ ID NO: 53, 54 | V$_λ$L-1a | SEQ ID NO: 72 |
| V$_H$-1b | SEQ ID NO: 129 | V$_κ$L-1b | SEQ ID NO: 55, 56 | V$_λ$L-1b | SEQ ID NO: 73, 74 |
| V$_H$-1c | SEQ ID NO: 130 | V$_κ$L-1c | SEQ ID NO: 57, 58 | V$_λ$L-1c | SEQ ID NO: 75 |
| V$_H$-1d | SEQ ID NO: 131 | V$_κ$L-1d | SEQ ID NO: 59 | V$_λ$L-2 | SEQ ID NO: 76 |
| V$_H$-2a | SEQ ID NO: 132 | V$_κ$L-2a | SEQ ID NO: 60 | V$_λ$L-3a | SEQ ID NO: 77, 78 |
| V$_H$-2b | SEQ ID NO: 133 | V$_κ$L-2b | SEQ ID NO: 61, 62 | V$_λ$L-3b | SEQ ID NO: 79 |
| V$_H$-3a | SEQ ID NO: 134 | V$_κ$L-3a | SEQ ID NO: 63, 64 | V$_λ$L-3c | SEQ ID NO: 80 |
| V$_H$-3b | SEQ ID NO: 135 | V$_κ$L-3b | SEQ ID NO: 65 | V$_λ$L-3d | SEQ ID NO: 81 |
| V$_H$-3c | SEQ ID NO: 136 | V$_κ$L-3c | SEQ ID NO: 66 | V$_λ$L-4 | SEQ ID NO: 82, 83 |
| V$_H$-4a | SEQ ID NO: 137 | V$_κ$L-4a | SEQ ID NO: 67 | V$_λ$L-5 | SEQ ID NO: 84, 85 |
| V$_H$-4b | SEQ ID NO: 138 | V$_κ$L-5a | SEQ ID NO: 68 | V$_λ$L-6 | SEQ ID NO: 86 |
| V$_H$-5a | SEQ ID NO: 139 | V$_κ$L-6a | SEQ ID NO: 69 | V$_λ$L-7 | SEQ ID NO: 87, 88 |
| V$_H$-6a | SEQ ID NO: 140 | V$_κ$L-6b | SEQ ID NO: 70 | V$_λ$L-8 | SEQ ID NO: 89 |
| V$_H$-7a | SEQ ID NO: 141 | huC$_κ$-2 | SEQ ID NO: 115 | V$_λ$L-4/9 | SEQ ID NO: 90, 91 |
| huC$_H$-2 | SEQ ID NO: 104, 105, 106 | | | V$_λ$L-10 | SEQ ID NO: 92 |
| | | | | huC$_λ$-2 | SEQ ID NO: 120, 121, 122, 123, 124, 125 |

Figure 3:
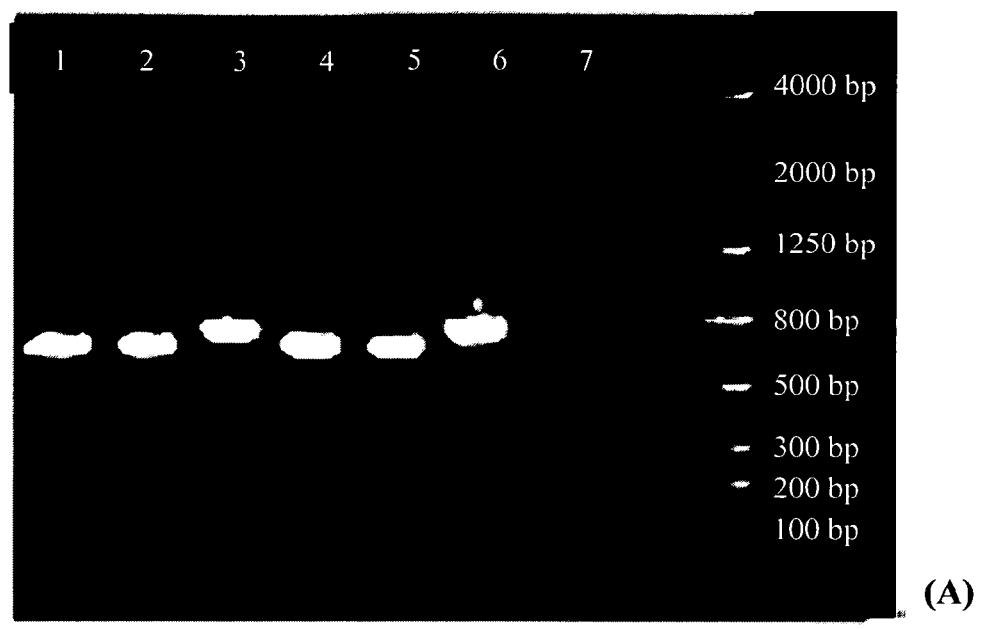
FIG. 3 Agarose gel analysis of the amplified nucleic acid after the first (A) and the second (B) polymerase chain reaction with different primer sets; (A) 1—IgG HC and IgG LC(κ) 55° C.; 2—IgG LC(κ) 55° C.; 3—IgG HC 55° C.; 4—IgG HC and IgG LC(κ) 50° C.; 5—IgG LC(κ) 50° C.; 6—IgG HC 50° C.; 7—H$_2$O PCRI; (B) 1—IgG LC(κ) 55° C.; 2—IgG HC and IgG LC(κ) 55° C.; 3—IgG HC 55° C.; 4—IgG HC and IgG LC(κ) 50° C.; 5—IgG LC(κ) 50° C.; 6—IgG HC 50° C.; 7—H$_2$O PCRII; 8—H$_2$O PCRI.
Figure 3:
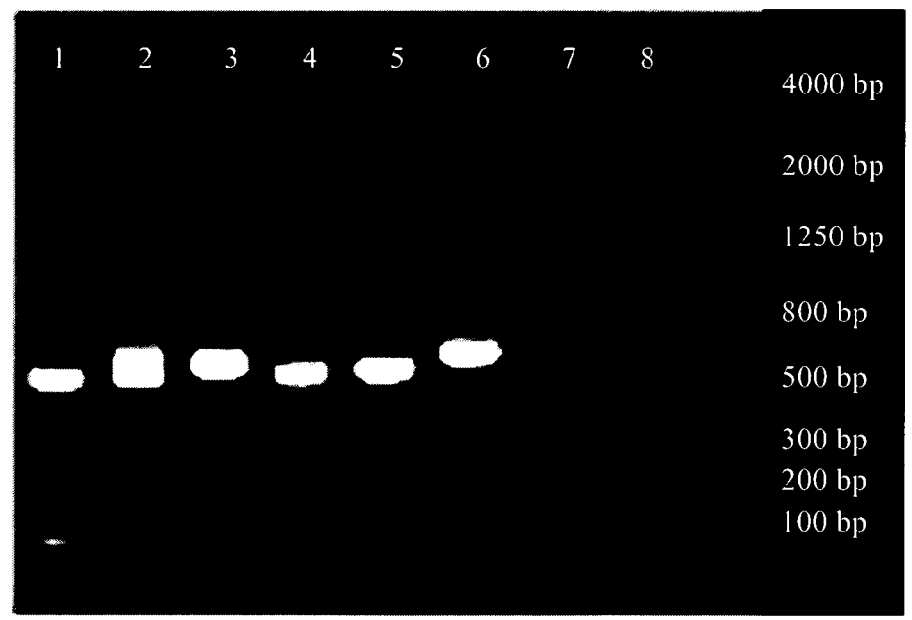

In FIG. 3 the agarose gel of the amplified nucleic acid fragments obtained in this polymerase chain reaction is shown. The samples were analyzed after 40 amplification cycles with an annealing temperature of 50° C. and 55° C., respectively. The blanks (water) were negative and the size of the fragments correlated well to the expected sizes of 750 bp (IgG HC) and 665 bp (IgG LC), respectively, after the first polymerase chain reaction and of 711 bp and 688 bp, respectively, after the second polymerase chain reaction.

Example 2

Figure 4:
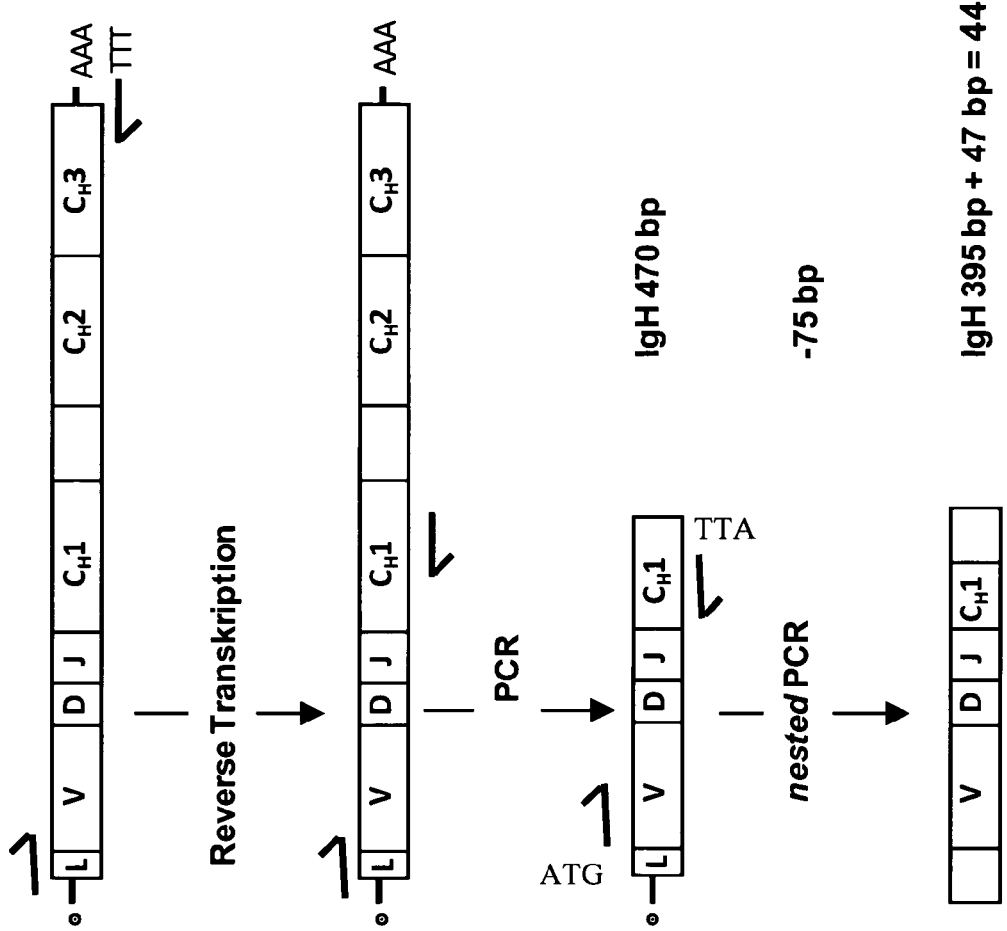
FIG. 4 Scheme for the polymerase chain reaction for the immunoglobulin heavy chain with a different second primer set in the two polymerase chain reactions.

Amplification of IgG Genes from Humanized Immunized Mice's Single B Cell by a Polymerase Chain Reaction with Two Changed Primer Sets Single B-cells of a mouse having a human immunoglobulin locus have been obtained as outlined above. The 5'-primer and the 3'-primer of the first and second primer set were different to each other insofar as the primer of each of the second sets bound in a more inward region of the nucleic acid. A scheme of this polymerase chain reaction is given in FIG. 4.

The employed sets of primer for the first polymerase chain reaction are denoted in the following list:

| Ig heavy chain primer | | Ig light chain (κ) primer | | Ig light chain (λ) primer | |
|---|---|---|---|---|---|
| $V_HL$-1 | SEQ ID NO: 05, 06 | $V_\kappa L$-1 | SEQ ID NO: 16 | $V_\lambda L$-1 | SEQ ID NO: 21 |
| $V_HL$-2 | SEQ ID NO: 07, 08 | $V_\kappa L$-2 | SEQ ID NO: 17 | $V_\lambda L$-2 | SEQ ID NO: 22 |
| $V_HL$-3 | SEQ ID NO: 09 | $V_\kappa L$-3 | SEQ ID NO: 18 | $V_\lambda L$-3 | SEQ ID NO: 23, 24, 25, 26 |
| $V_HL$-4 | SEQ ID NO: 10, 11 | $V_\kappa L$-4 | SEQ ID NO: 19 | $huC_\lambda$-II | SEQ ID NO: 27, 28 |
| $V_HL$-5 | SEQ ID NO: 12 | $huC_\kappa$-II | SEQ ID NO: 20 | | |
| $V_HL$-6 | SEQ ID NO: 13 | | | | |
| $huC_H$II | SEQ ID NO: 14, 15 | | | | |

The employed sets of primer for the second polymerase chain reaction are denoted in the following list:

| IgG heavy chain primer | | IgG light chain (κ) primer | | IgG light chain (λ) primer | |
|---|---|---|---|---|---|
| $V_HL$-1a | SEQ ID NO: 29, 30 | $V_\kappa L$-1a | SEQ ID NO: 53, 54 | $V_\lambda L$-1a | SEQ ID NO: 72 |
| $V_HL$-1b | SEQ ID NO: 31 | $V_\kappa L$-1b | SEQ ID NO: 55, 56 | $V_\lambda L$-1b | SEQ ID NO: 73, 74 |
| $V_HL$-1c | SEQ ID NO: 32, 33 | $V_\kappa L$-1c | SEQ ID NO: 57, 58 | $V_\lambda L$-1c | SEQ ID NO: 75 |
| $V_HL$-1d | SEQ ID NO: 34, 35 | $V_\kappa L$-1d | SEQ ID NO: 59 | $V_\lambda L$-2a | SEQ ID NO: 76 |
| $V_HL$-2a | SEQ ID NO: 36 | $V_\kappa L$-2a | SEQ ID NO: 60 | $V_\lambda L$-3a | SEQ ID NO: 77, 78 |
| $V_HL$-2b | SEQ ID NO: 37, 38 | $V_\kappa L$-2b | SEQ ID NO: 61, 62 | $V_\lambda L$-3b | SEQ ID NO: 79 |
| $V_HL$-3a | SEQ ID NO: 39, 40 | $V_\kappa L$-3a | SEQ ID NO: 63, 64 | $V_\lambda L$-3c | SEQ ID NO: 80 |
| $V_HL$-3b | SEQ ID NO: 41 | $V_\kappa L$-3b | SEQ ID NO: 65 | $V_\lambda L$-3d | SEQ ID NO: 81 |
| $V_HL$-3c | SEQ ID NO: 42 | $V_\kappa L$-3c | SEQ ID NO: 66 | $V_\lambda L$-4a | SEQ ID NO: 82, 83 |
| $V_HL$-4a | SEQ ID NO: 43, 44 | $V_\kappa L$-4a | SEQ ID NO: 67 | $V_\lambda L$-5a | SEQ ID NO: 84, 85 |
| $V_HL$-4b | SEQ ID NO: 45 | $V_\kappa L$-5a | SEQ ID NO: 68 | $V_\lambda L$-6a | SEQ ID NO: 86 |
| $V_HL$-5a | SEQ ID NO: 46, 47 | $V_\kappa L$-6a | SEQ ID NO: 69 | $V_\lambda L$-7a | SEQ ID NO: 87, 88 |
| $V_HL$-6a | SEQ ID NO: 48 | $V_\kappa L$-6b | SEQ ID NO: 70 | $V_\lambda L$-8a | SEQ ID NO: 89 |
| $V_HL$-7a | SEQ ID NO: 49, 50 | $huC_\kappa$-III | SEQ ID NO: 71 | $V_\lambda L$-4/9a | SEQ ID NO: 90, 91 |
| $huC_H$III | SEQ ID NO: 51, 52 | | | $V_\lambda L$-10a | SEQ ID NO: 92 |
| | | | | $huC_\lambda$-III | SEQ ID NO: 93 |

Figure 5:
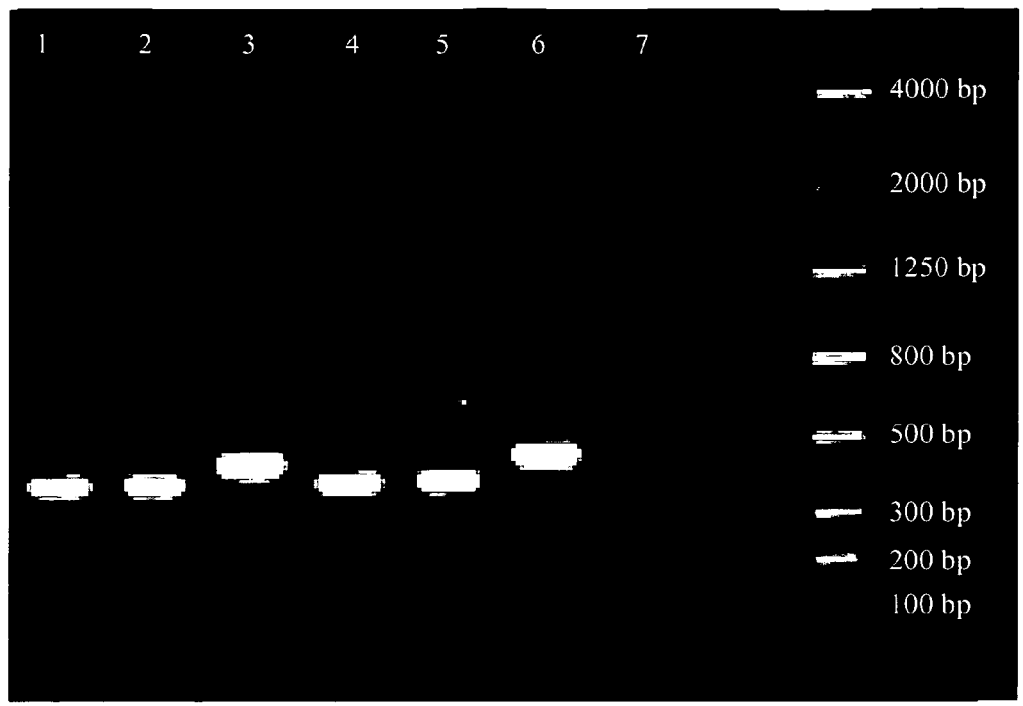
FIG. 5 Agarose gel analysis of the amplified nucleic acid after the first (A) and the second (B) polymerase chain reaction with different primer sets; (A) 1—IgG HC and IgG LC(κ) 55° C.; 2—IgG LC(κ) 55° C.; 3—IgG HC 55° C.; 4—IgG HC and IgG LC(κ) 50° C.; 5—IgG LC(κ) 50° C.; 6—IgG HC 50° C.; 7—$H_2O$ PCRI; (B) 1—IgG HC and IgG LC(κ) 55° C.; 2—IgG LC(κ) 55° C.; 3—IgG HC 55° C.; 4—IgG HC and IgG LC(κ) 50° C.; 5—IgG LC(κ) 50° C.; 6—IgG HC 50° C.; 7—$H_2O$ PCRII; 8—$H_2O$ PCRI.
Figure 5:

In FIG. 5 the agarose gel of the amplified nucleic acid fragments obtained in this polymerase chain reaction is shown. The samples were analyzed after 40 amplification cycles with an annealing temperature of 50° C. and 55° C., respectively. The blanks (water) were negative and the size of the fragments correlated well to the expected sizes of 471 bp (IgG HC) and 413 bp (IgG LC), respectively, after the first polymerase chain reaction and of 442 bp and 399 bp, respectively, after the second polymerase chain reaction.

Example 3

Figure 6:
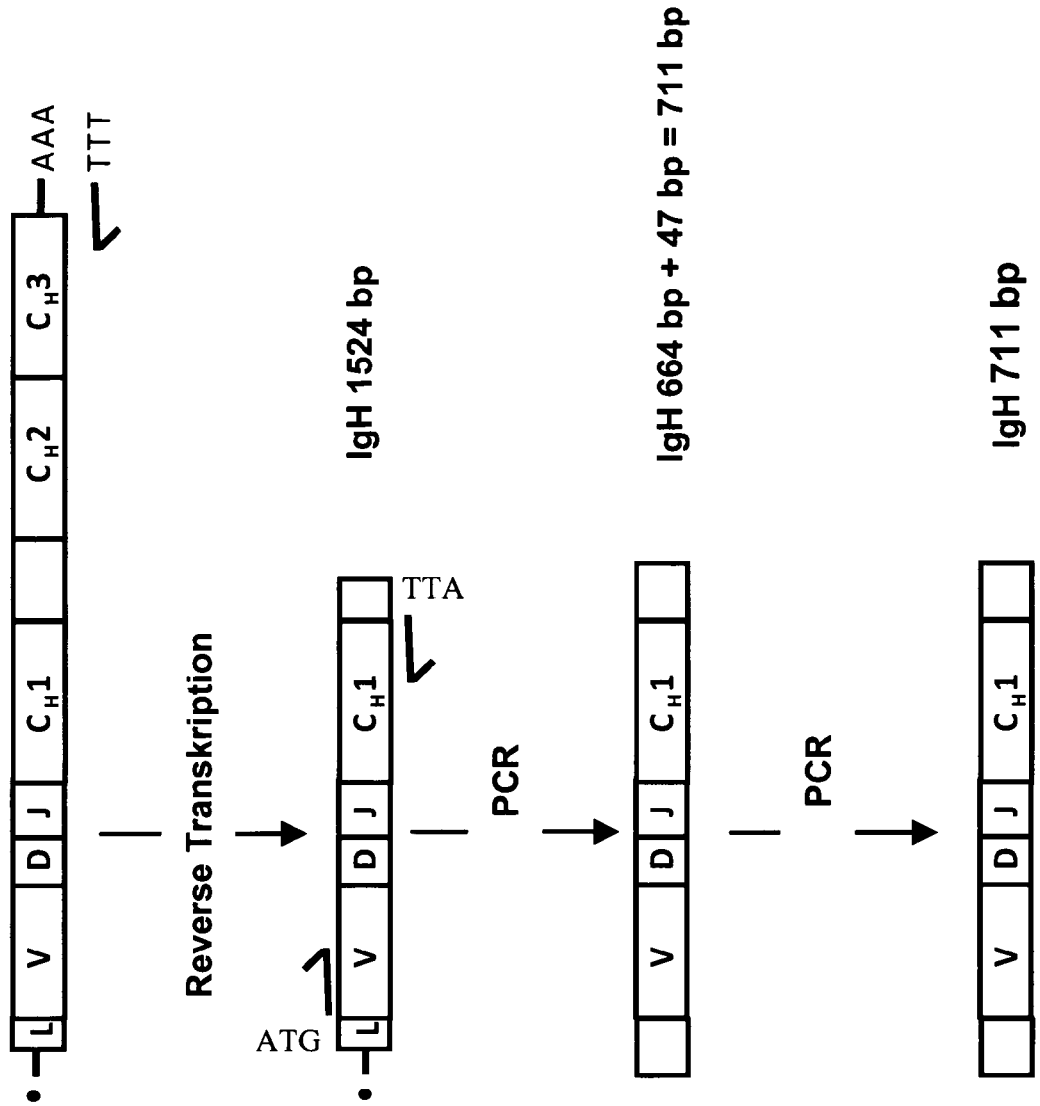
FIG. 6 Scheme for the polymerase chain reaction for the immunoglobulin heavy chain with identical primer set in the two polymerase chain reactions.

Amplification of IgG Genes from Humanized Immunized Mice's Single B Cell by a Polymerase Chain Reaction with Two Identical Primer Sets Single B-cells of a mouse having a human immunoglobulin locus have been obtained as outlined above. The 5'-primer and the 3'-primer of the first and second primer set were identical. A scheme of this polymerase chain reaction is given in FIG. 6.

The employed sets of primer for the first and second polymerase chain reaction are denoted in the following list:

| Ig heavy chain primer | | Ig light chain (κ) primer | | Ig light chain (λ) primer | |
|---|---|---|---|---|---|
| $huV_H$-1 | SEQ ID NO: 94 | $huV_\kappa$-1 | SEQ ID NO: 107, 108, 109, 110 | $huV_\lambda$-1 | SEQ ID NO: 116 |
| $huV_H$-2 | SEQ ID NO: 95 | $huV_\kappa$-2 | SEQ ID NO: 111, 112 | $huV_\lambda$-2 | SEQ ID NO: 117 |
| $huV_H$-3 | SEQ ID NO: 96, 97, 98, 99 | $huV_\kappa$-3 | SEQ ID NO: 113 | $huV_\lambda$-3 | SEQ ID NO: 118, 119 |
| $huV_H$-4 | SEQ ID NO: 100, 101, 102, 103 | $huV_\kappa$-4 | SEQ ID NO: 114 | $huC_\lambda$-2 | SEQ ID NO: 120, 121, 122, 123, 124, 125 |
| $huC_H$-2 | SEQ ID NO: 104, 105, 106 | $huC_\kappa$-2 | SEQ ID NO: 115 | | |

Figure 7:
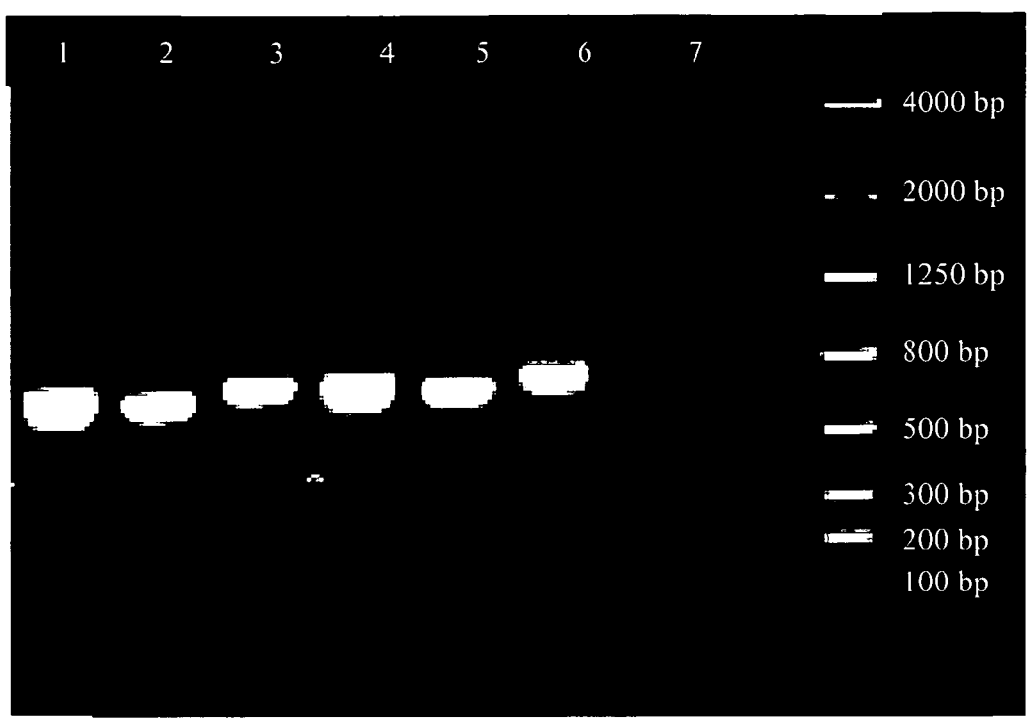
FIG. 7 Agarose gel analysis of the amplified nucleic acid after the first (A) and the second (B) polymerase chain reaction with different primer sets; (A) 1—IgG HC and IgG LC(κ) 55° C.; 2—IgG LC(κ) 55° C.; 3—IgG HC 55° C.; 4—IgG HC and IgG LC(κ) 50° C.; 5—IgG LC(κ) 50° C.; 6—IgG HC 50° C.; 7—$H_2O$ PCRI; (B) 1—IgG LC(κ) 55° C.; 2—IgG HC and IgG LC(κ) 55° C.; 3—IgG HC 55° C.; 4—IgG HC and IgG LC(κ) 50° C.; 5—IgG LC(κ) 50° C.; 6—IgG HC 50° C.; 7—$H_2O$ PCRII; 8—$H_2O$ PCRI.
Figure 7:
Figure 8:
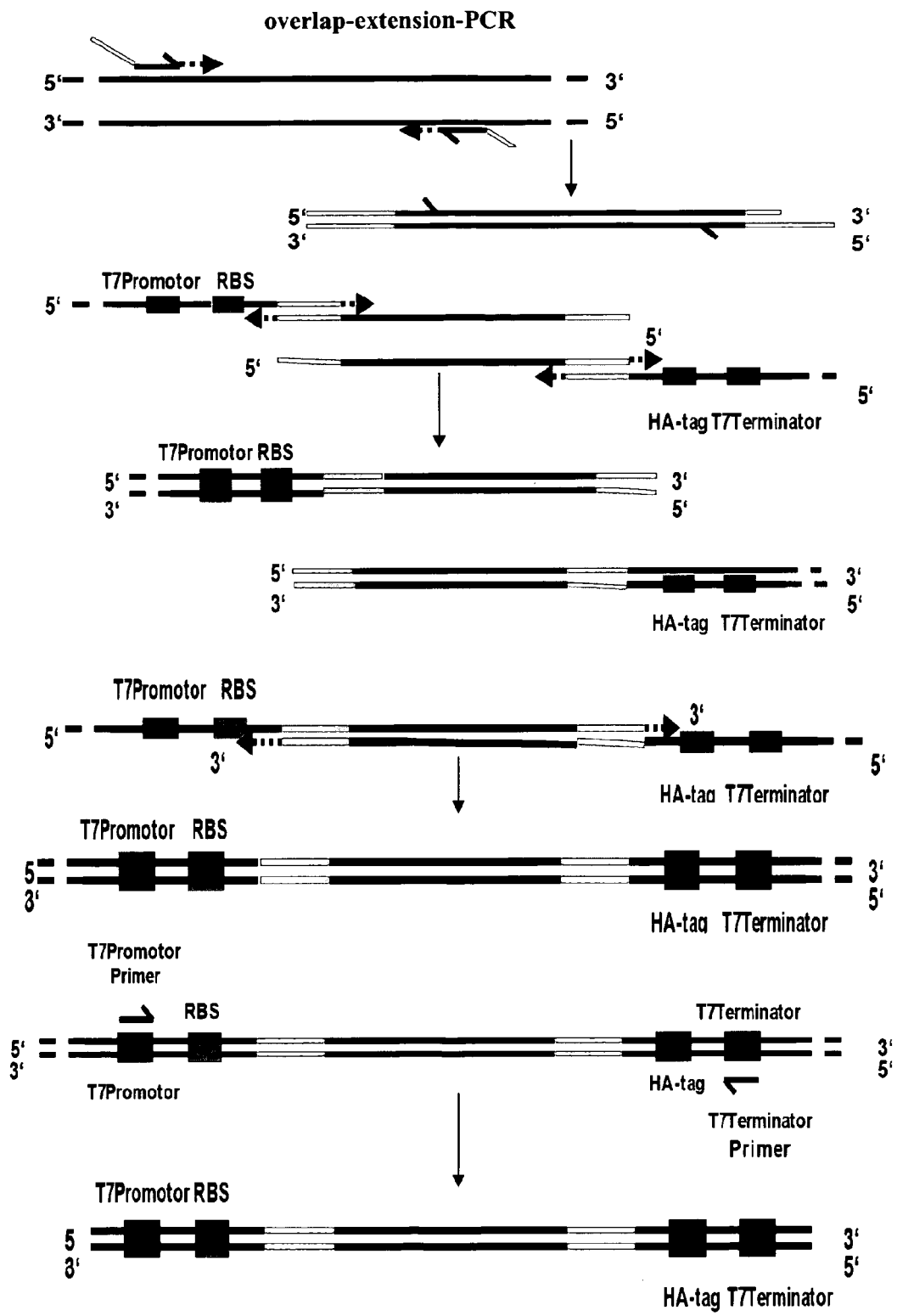
FIG. 8 Scheme of overlapping extension PCR exemplified with a C-terminal HA-tag.

In FIG. 7 the agarose gel of the amplified nucleic acid fragments obtained in this polymerase chain reaction is shown. The samples were analyzed after 40 amplification cycles with an annealing temperature of 50° C. and 55° C., respectively. The blanks (water) were negative and the size of the fragments correlated well to the expected sizes of 711 bp (IgG HC) and 688 bp (IgG LC), respectively, after the first and second polymerase chain reaction.

Example 4

Generation of Linear Template for In Vitro Translation

For the first polymerase chain reaction gene specific primer have been designed comprising the necessary overlapping sequences to the regulatory DNA regions of the T7 phage. For the second polymerase chain reaction the product of the first PCR was combined with nucleic acid fragments comprising the regulatory sequences and encoding the tag-sequence, respectively. A 3'-terminal extension was achieved by hybridization with the nucleic acid fragments comprising the regulatory elements. This linear expression construct is further amplified with the help of two terminal primer. These primer comprise the following sequence: 5'-CTTTAAGAAG-GAGATATACC+ATG+15-20 bp of the gene-specific sequence (5'-primer, SEQ ID NO: 126) or 5'-ATCG-TATGGGTAGCTGGTCCC+TTA+15-20 bp of the gene-specific sequence (3'-primer, SEQ ID NO: 127).

Figure 9:
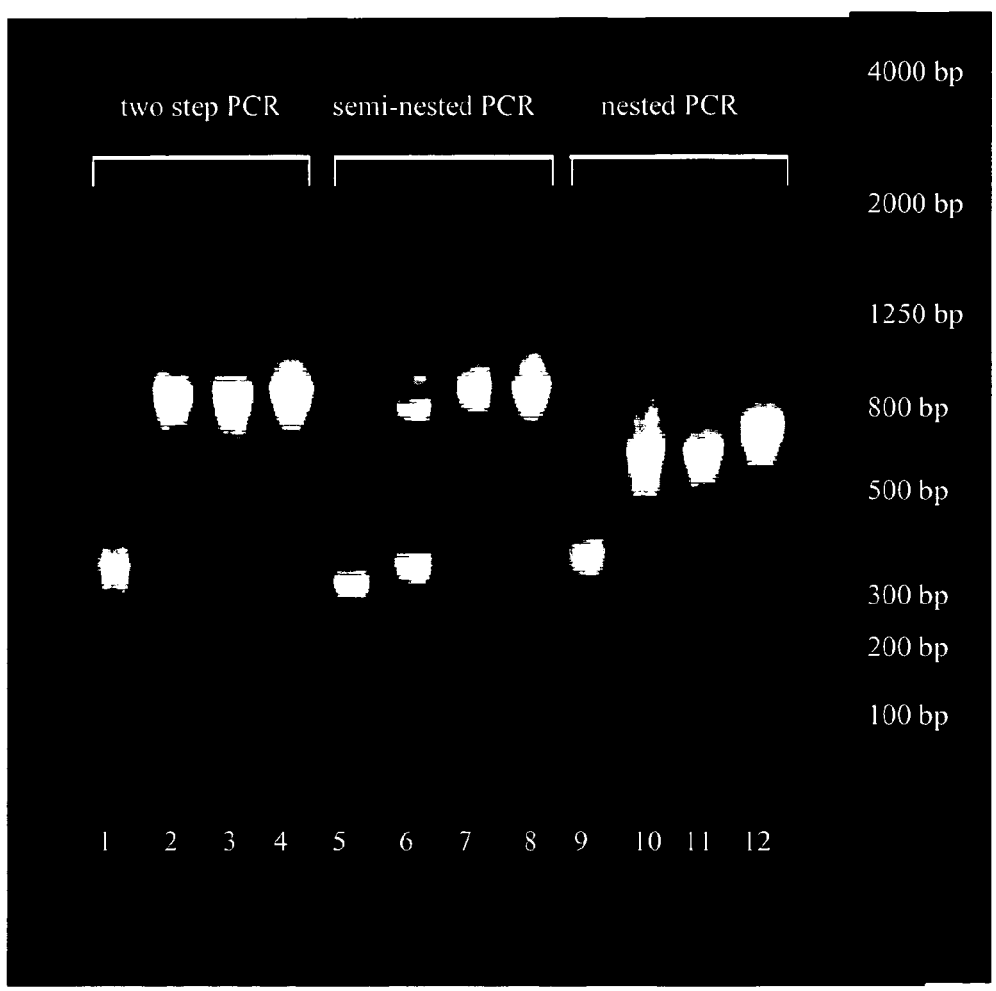
FIG. 9 Agarose gel analysis of the linear expression constructs of the three different polymerase chain reactions of examples 1 to 3.

In FIG. 9 lanes 1, 5 and 9 represent the blank water controls. The heavy chain nucleic acid are contained in lanes 4, 8, and 12, and the kappa light chains in lanes 3, 7, and 11. Lanes 2, 6, and 10 show combined samples of both chains. All nucleic acids have the expected size (see Table 38).

TABLE 38

Size of the linear expression constructs.

| immunoglobulin chain | two fixed primer sets | one fixed primer set | two variable primer sets |
|---|---|---|---|
| IgG HC | ~1110 bp | ~1110 bp | ~822 bp |
| IgG LC(κ) | ~1089 bp | ~1089 bp | ~799 bp |

Example 5

In Vitro Translation and Hufab Specific ELISA

In vitro translation is carried out as outlined above.

Figure 10:
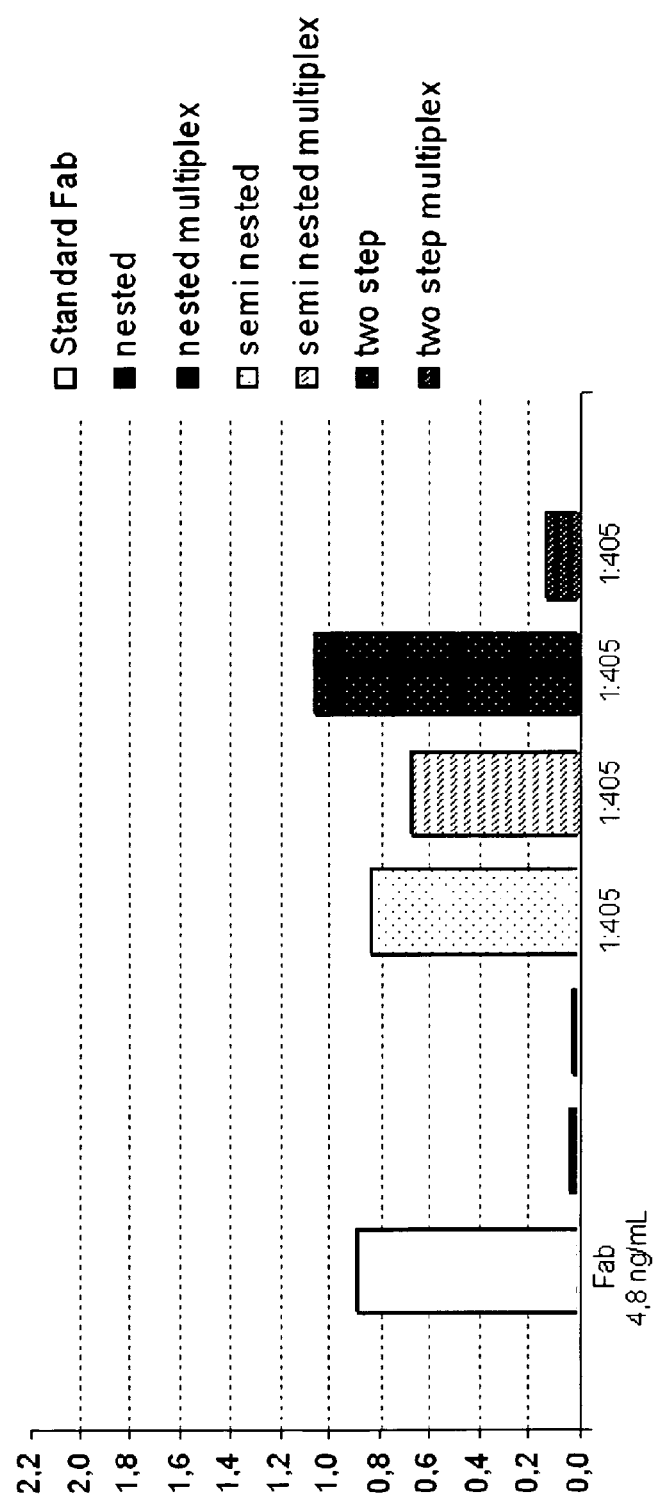
FIG. 10 Comparison of the result of the three polymerase chain reactions according to the invention after in vitro translation (determination at 450 nm, reference wavelength at 620 nm, background substracted).

As can be seem from FIG. 10 nucleic acids obtained with a two-step polymerase chain reaction with two variable primer sets does not provide for a linear expression construct which allows the in vitro production of the encoded Fab immunoglobulin fragment. In contrast the two-step polymerase chain reaction with one fixed and one variable set of primer employed in separated successive polymerase chain reactions allows for the subsequent provision of a linear expression construct and the in vitro translation of IgG HC and IgG LC comprising immunoglobulin Fab fragment.

In contrast to this is the two-step polymerase chain reaction comprising one fixed set of primer more efficient in the multiplex format as the polymerase chain reaction employing two fixed sets of primer. By employing only one fixed set of primer up to 5-times higher optical densities can be achieved.

Example 6

Figure 11:
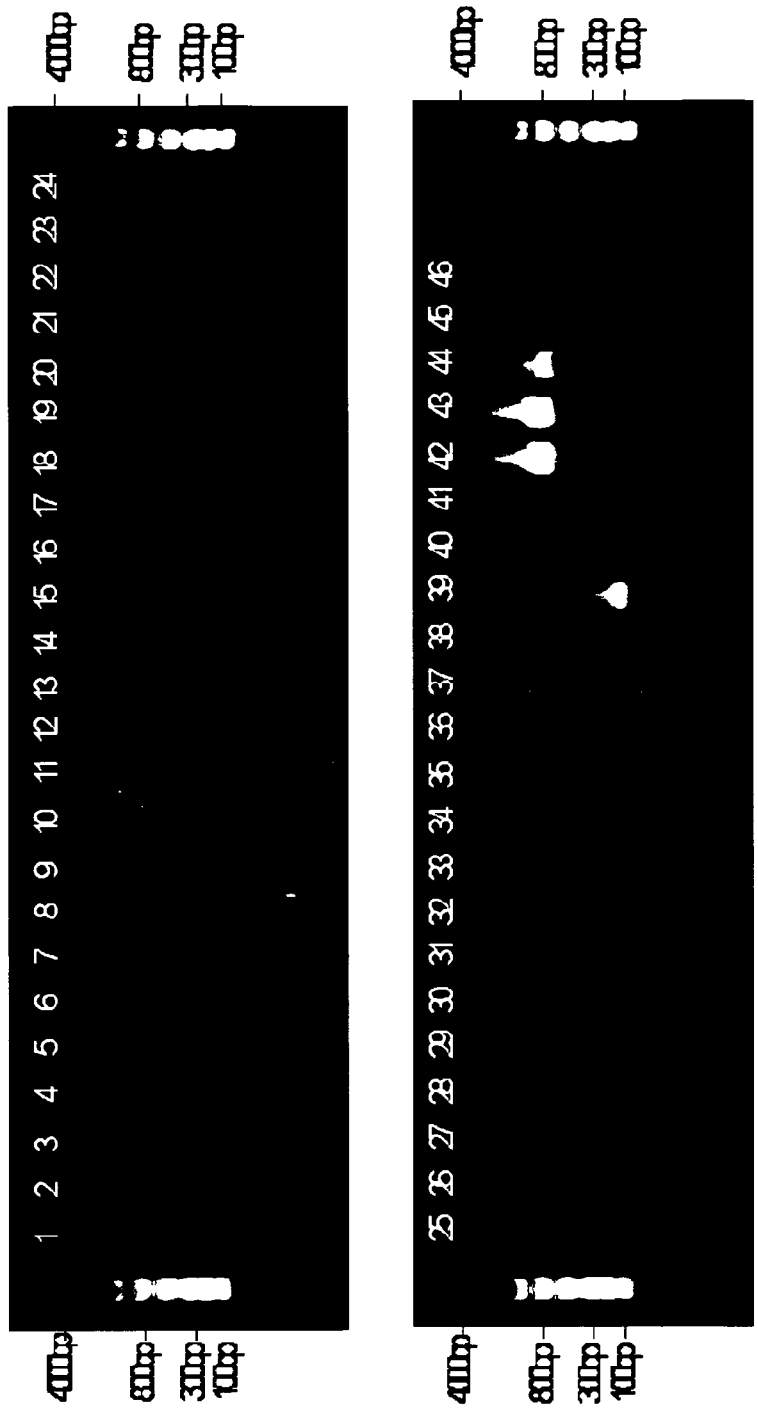
FIG. 11 Agarose gel analysis of the amplified nucleic acid after the first the second polymerase chain reaction with two identical sets of primer; 1—no RT, 2—37 single cells, 38—$H_2O$ cDNA, 39—control mRNA, 40—$H_2O$ control mRNA, 41—$H_2O$ PCRII, 42—IgG HC/IgG LC(κ), 43—IgG HC, 44—IgG LC(κ), 45—$H_2O$ PCRI, 46—GFP, 46—$H_2O$ GFP.
Figure 12:
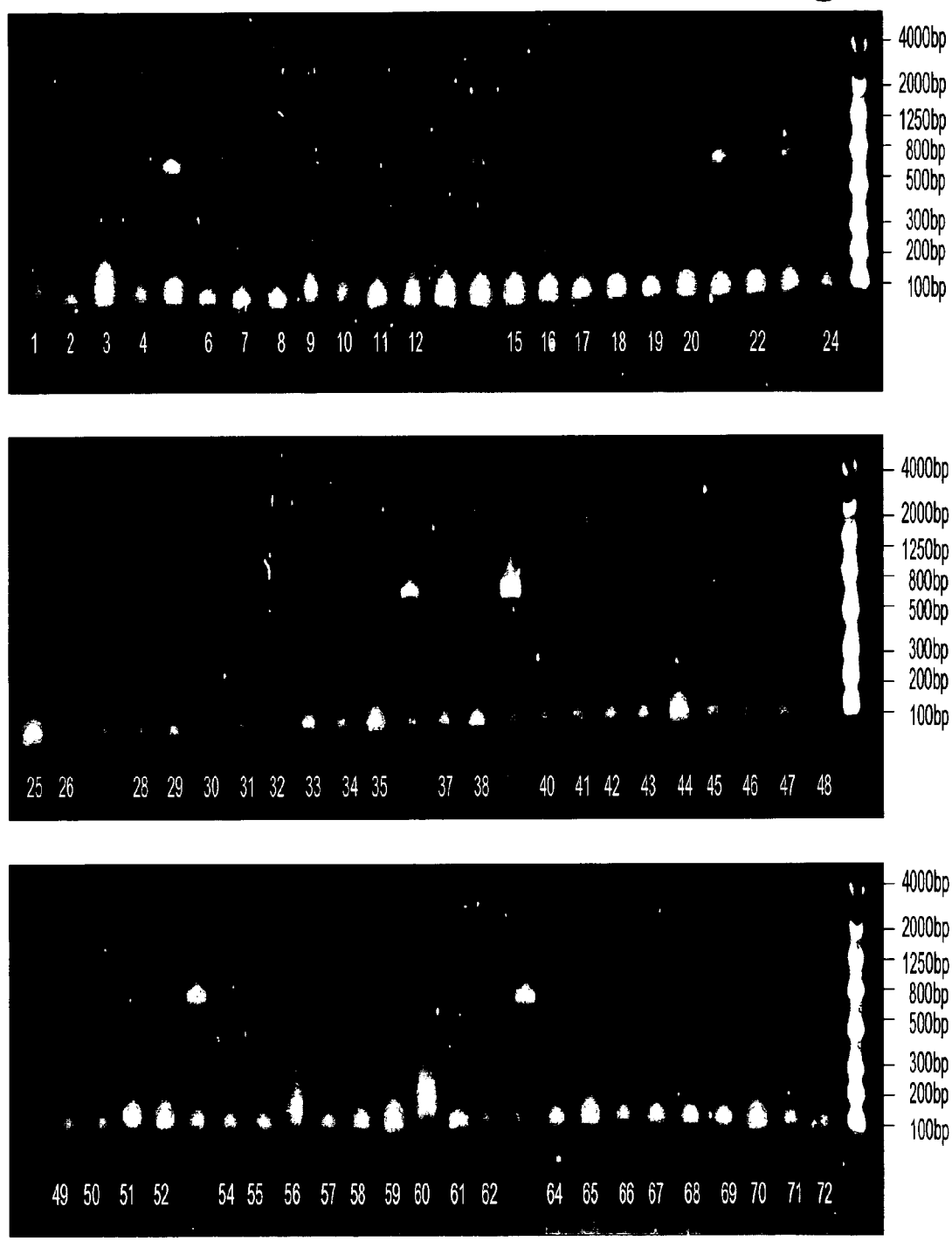
FIG. 12 Agarose gel analysis of the amplified nucleic acid after the second polymerase chain reaction with one variable and one fixed set of primer.

In Vitro Translation and Hufab Specific ELISA with a Nucleic Acid Obtained from a from Single Cell Two-step polymerase chain reaction with identical primer sets As can be seen from FIG. 11 the control samples yielded no signal in an agarose gel. Single deposited B-cells also showed no signal. IgG HC and IgG LC(κ) could be amplified from control samples.

Figure 13:
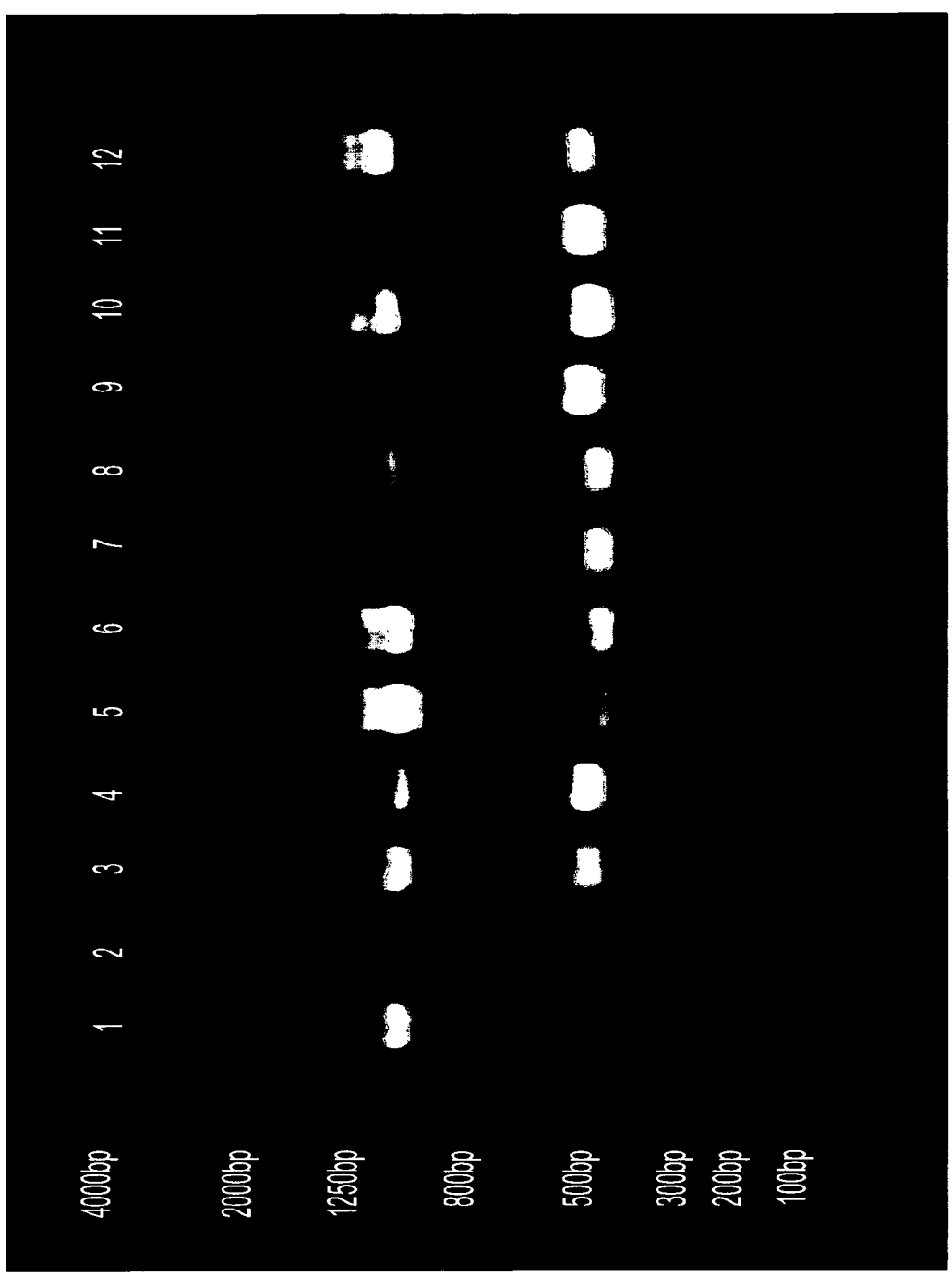
FIG. 13 Agarose gel analysis of the linear expression constructs obtained from nucleic acid after the second polymerase chain reaction with one variable and one fixed set of primer.
Figure 14:
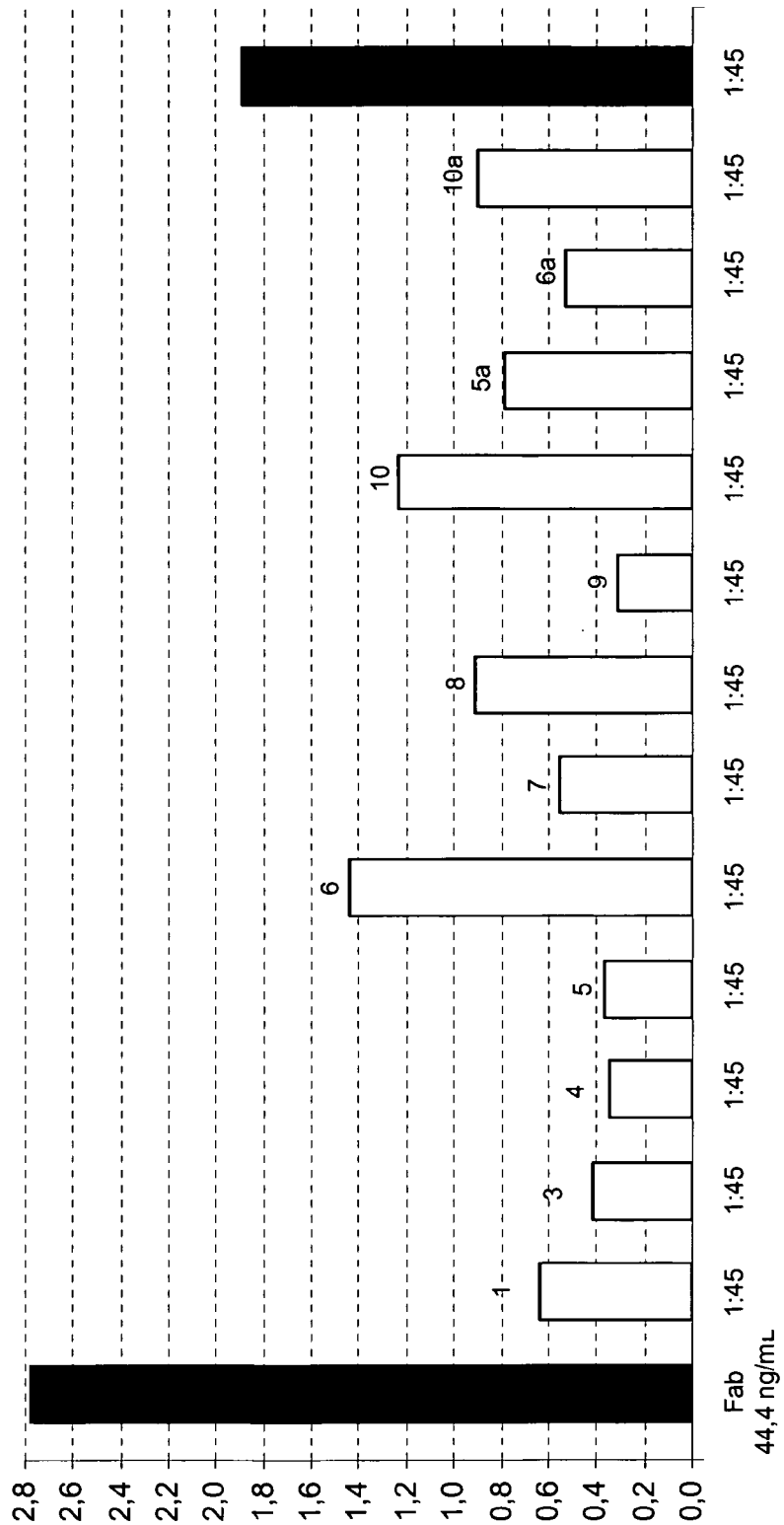
FIG. 14 Result of the in vitro translation of an IgG specific two-step polymerase chain reaction of a single cell with one fixed set of primer and one variable set of primer.
Figure 15:
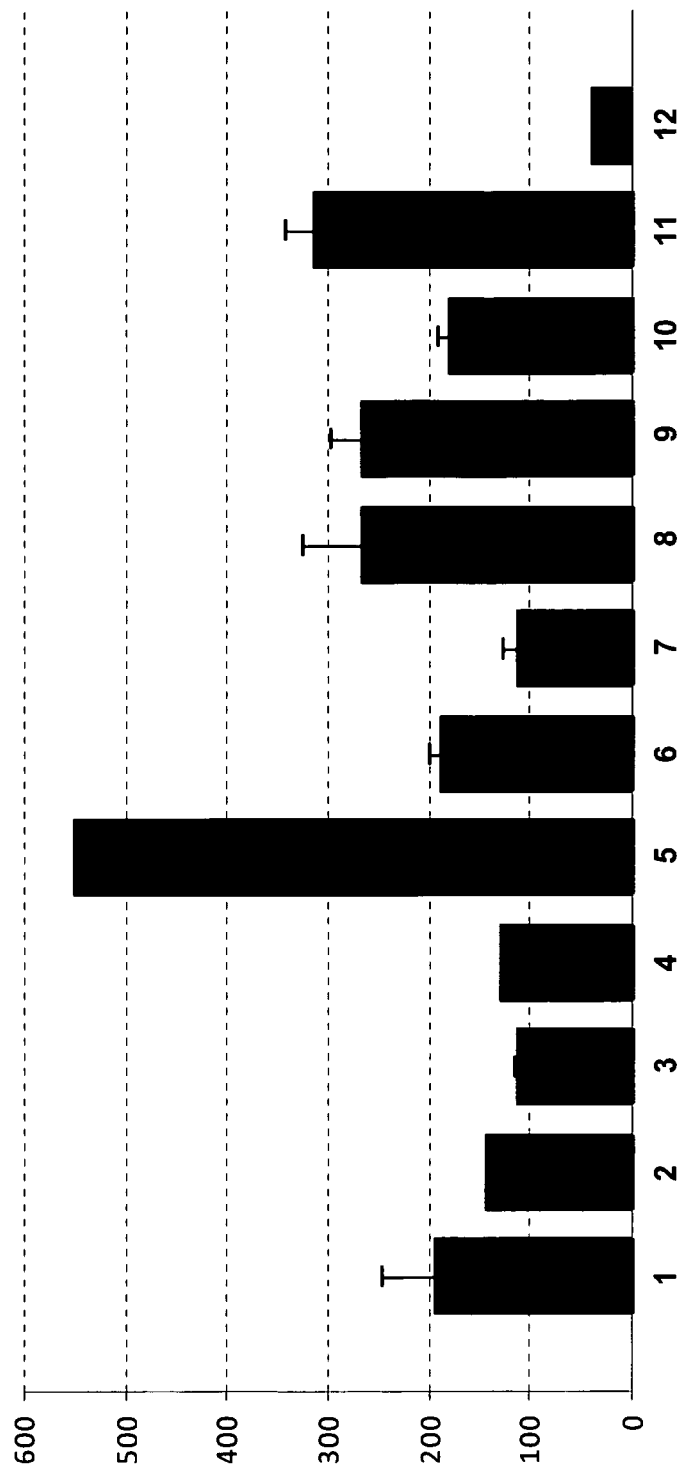
FIG. 15 Human Fab immunoglobulin fragments after single cell polymerase chain reaction and in vitro translation; 1-8 human Fab fragments after in vitro translation of IgG HC and IgG LC(κ) obtained from a single cell and addition of IgG HC control sample, 9-11 human Fab fragments after in vitro translation of IgG HC and IgG LC(κ) obtained from a single cell, 12 human Fab fragments after in vitro translation of IgG HC and IgG LC(λ) obtained from a single cell.

Two-Step Polymerase Chain Reaction with One Fixed Set of Primer and One Variable Set of Primer As can be seen from FIG. 13 all nucleic acids, except for sample 2, obtained with a two-step polymerase chain reaction with one fixed set of primer and one variable set of primer allowed for providing a linear expression construct for the production of IgG HC and IgG LC. Thus, these multiplex polymerase chain reaction are well suited.

Figure 16:
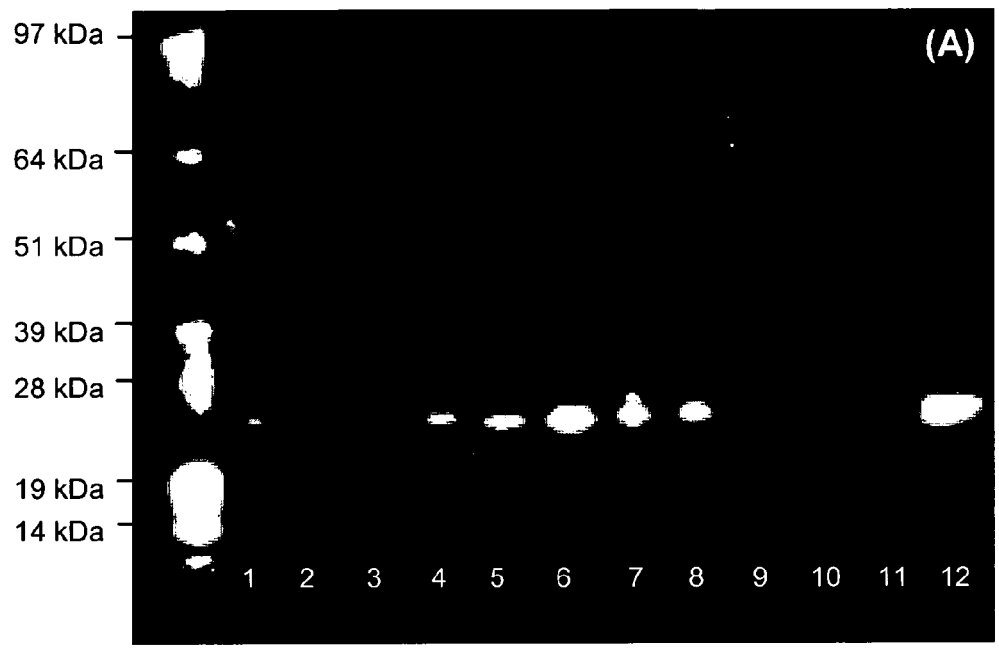
FIG. 16 Western blot analysis after a two-step polymerase chain reaction with one fixed set of primer and one variable set of primer and in vitro translation; (A) 1—IgG HC/IgG LC from a single cell combined with IgG HC, 2-4 IgG HC/IgG LC from a single cell, 5-7 IgG HC/IgG LC(κ) control, 8—IgG HC and IgG LC(κ) control, 9—negative control, 10—standard Fab 0.5 ng/ml, 11—standard Fab 50 ng/ml, 12—standard Fab 5 μg/ml; (B) 1—standard Fab 5 μg/ml, 2—standard Fab 50 ng/ml, 3—standard Fab 0.5 ng/ml, 3—negative control, 5-12 IgG HC/IgG LC from a single cell combined with IgG HC.
Figure 16:
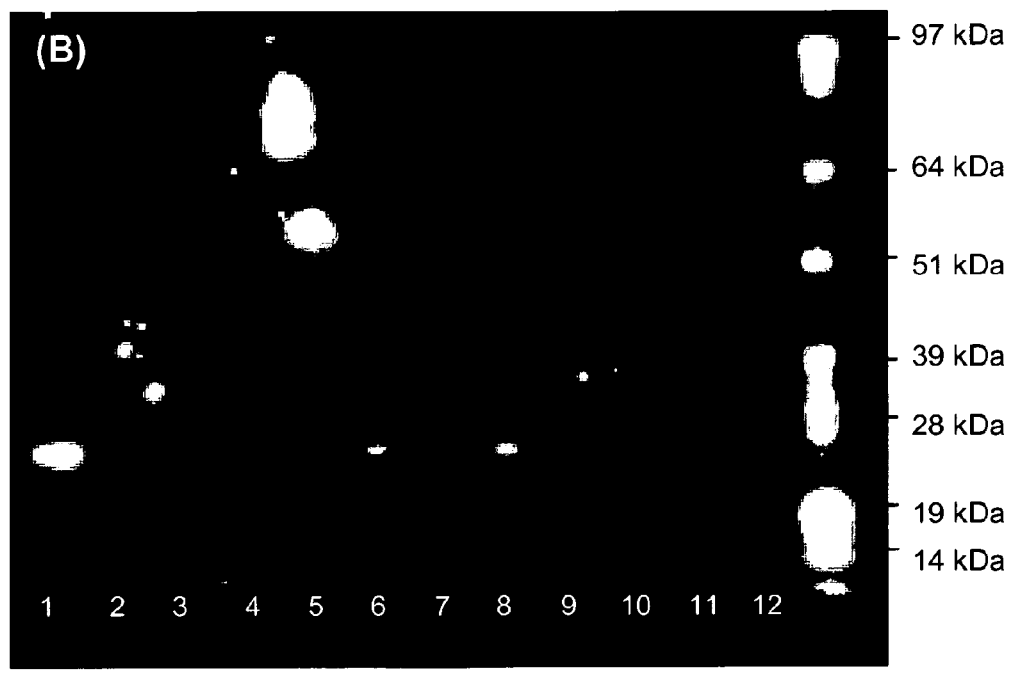

The concentrations of the obtained human kappa Fab immunoglobulin fragments are between 100 and 550 ng/ml. Lanes 9 to 11 of FIG. 16 show IgG HC and IgG LC(κ) obtained from a single cell without the addition of IgG HC positive control. Here the obtained amount of human Fab immunoglobulin fragment was between 180 and 330 ng/ml.

The invention claimed is:

1. A method for obtaining a nucleic acid from a single cell, wherein said nucleic acid encodes an immunoglobulin variable domain selected from a heavy chain variable domain, a kappa light chain variable domain, and a lambda light chain variable domain, comprising: (a) performing a first polymerase chain reaction (PCR) to obtain a first PCR product; and (b) performing a second PCR with the first PCR product, whereby the distance of the binding locations of the primers employed in the second PCR is reduced compared to the distance in the first PCR, wherein:
  i) for obtaining the nucleic acid encoding the immunoglobulin heavy chain variable domain, the first PCR is performed with 5' primers comprising the nucleic acids of SEQ ID NO: 05 and/or 06, 07 and/or 08, 09, 10 and/or 11, 12, and 13, and with a 3' primer comprising the nucleic acid of SEQ ID NO:104 or 105 or 106, and the second PCR is performed with 5' primers comprising the nucleic acids of SEQ ID NO: 128, 129, 130, 131, 132, 133, 134, 135, 136, 137, 138, 139, 140, and 141 and/or 142 and with a 3' primer comprising the nucleic acid of SEQ ID NO: 104 or 105 or 106 or 143, and
  ii) for obtaining the nucleic acid encoding the immunoglobulin kappa light chain variable domain, the first PCR is performed with 5' primers comprising the nucleic acids of SEQ ID NO: 16, 17, 18, and 19, and with a 3' primer comprising the nucleic acid of SEQ ID NO: 115, and the second PCR is performed with 5' primers comprising the nucleic acids of SEQ ID NO: 53 and/or 54, 55 and/or 56, 57 and/or 58, 59, 60, 61 and/or 62, 63 and/or 64, 65, 66, 67, 68, 69, 70, and 144, and with a 3' primer(s) comprising the nucleic acid(s) of SEQ ID NO: 115 and/or 145, and
  iii) for obtaining the nucleic acid encoding the immunoglobulin lambda light chain variable domain, the first PCR is performed with 5' primers comprising the nucleic acids of SEQ ID NO: 21, 22, 23 and/or 24 and/or 25 and/or 26, and with a 3' primer(s) comprising the nucleic acid(s) of SEQ ID NO:120 and/or 121 and/or 122 and/or 123 and/or 124 and/or 125, and the second PCR is performed with 5' primers comprising the nucleic acids of SEQ ID NO: 72, 73 and/or 74, 75, 76, 77 and/or 78, 79, 80, 81, 82 and/or 83, 84 and/or 85, 86, 87 and/or 88, 89, 90 and/or 91, and 92, and a 3' primer(s) comprising the nucleic acid(s) of SEQ ID NO: 120 and/or 121 and/or 122 and/or 123 and/or 124 and/or 125.

2. The method of claim 1, wherein the 3' primer(s) in the second PCR is/are the same as in the first PCR and at least one 5'-primer is changed, and whereby in the second PCR the number of nucleotides between the 5'-end of each of the 5'-primer and the 3'-end of the 3'-primer is reduced compared to the number of nucleotides between the 5'-end of each of the 5'-primer and the 3'-end of the 3'-primer in the first PCR, when bound to the nucleic acid to be amplified.

3. The method of claim 1, wherein the primers employed in the second PCR provide for overhangs encoding the translational start codon ATG for the 5'-primers and/or the translational stop codon TTA for the 3'-primer.

4. The method of claim 1, wherein said method comprises the first step of: providing a single cell and obtaining the mRNA of said cell.

5. The method of claim 4, wherein said method further comprises the following second step: —obtaining cDNA from said mRNA with a reverse transcriptase PCR.

6. The method of claim 1, wherein the single cell is a B-cell, a plasmablast, or a plasma cell.

7. The method of claim 1, wherein said immunoglobulin is a human immunoglobulin.

8. The method of claim 1, wherein said immunoglobulin is an immunoglobulin of the class G (IgG).

* * * * *

SEQUENCE LISTING

```
<160> NUMBER OF SEQ ID NOS: 145

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 327
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 3
<211> LENGTH: 107
<212> TYPE: PRT
<213> ORGANISM: Homo sapiens

<400> SEQUENCE: 3

Arg Thr Val Ala Ala Pro Ser Val Phe Ile Phe Pro Pro Ser Asp Glu
1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 4
<211> LENGTH: 104
<212> TYPE: PRT
<213> ORGANISM: Homo sapiens

<400> SEQUENCE: 4

Pro Lys Ala Ala Pro Ser Val Thr Leu Phe Pro Pro Ser Ser Glu Glu
1               5                  10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
```

Thr Val Ala Pro Thr Glu Cys Ser
         100

<210> SEQ ID NO 5
<211> LENGTH: 21
<212> TYPE: DNA
<213> ORGANISM: Homo sapiens

<400> SEQUENCE: 5
tcaccatgga ctgcacctgg a                                    21

<210> SEQ ID NO 6
<211> LENGTH: 21
<212> TYPE: DNA
<213> ORGANISM: Homo sapiens

<400> SEQUENCE: 6
tcaccatgga ctggacctgg a                                    21

<210> SEQ ID NO 7
<211> LENGTH: 22
<212> TYPE: DNA
<213> ORGANISM: Homo sapiens

<400> SEQUENCE: 7
ccatggacac actttgctcc ac                                   22

<210> SEQ ID NO 8
<211> LENGTH: 22
<212> TYPE: DNA
<213> ORGANISM: Homo sapiens

<400> SEQUENCE: 8
ccatggacac actttgttcc ac                                   22

<210> SEQ ID NO 9
<211> LENGTH: 23
<212> TYPE: DNA
<213> ORGANISM: Homo sapiens

<400> SEQUENCE: 9
tcaccatgga gtttgggctg agc                                  23

<210> SEQ ID NO 10
<211> LENGTH: 25
<212> TYPE: DNA
<213> ORGANISM: Homo sapiens

<400> SEQUENCE: 10
agaacatgaa acacctgtgg ttctt                                25

<210> SEQ ID NO 11
<211> LENGTH: 25
<212> TYPE: DNA
<213> ORGANISM: Homo sapiens

<400> SEQUENCE: 11
agaacatgaa acatctgtgg ttctt                                25

<210> SEQ ID NO 12
<211> LENGTH: 20
<212> TYPE: DNA

```
<213> ORGANISM: Homo sapiens

<400> SEQUENCE: 12
atggggtcaa ccgccatcct                                             20

<210> SEQ ID NO 13
<211> LENGTH: 23
<212> TYPE: DNA
<213> ORGANISM: Homo sapiens

<400> SEQUENCE: 13
acaatgtctg tctccttcct cat                                         23

<210> SEQ ID NO 14
<211> LENGTH: 19
<212> TYPE: DNA
<213> ORGANISM: Artificial
<220> FEATURE:
<223> OTHER INFORMATION: huCH-II

<400> SEQUENCE: 14
gccaggggga agaccgatg                                              19

<210> SEQ ID NO 15
<211> LENGTH: 19
<212> TYPE: DNA
<213> ORGANISM: Homo sapiens

<400> SEQUENCE: 15
gccaggggga agacggatg                                              19

<210> SEQ ID NO 16
<211> LENGTH: 21
<212> TYPE: DNA
<213> ORGANISM: Homo sapiens

<400> SEQUENCE: 16
gctcagctcc tggggctcct g                                           21

<210> SEQ ID NO 17
<211> LENGTH: 21
<212> TYPE: DNA
<213> ORGANISM: Homo sapiens

<400> SEQUENCE: 17
ctggggctgc taatgctctg g                                           21

<210> SEQ ID NO 18
<211> LENGTH: 21
<212> TYPE: DNA
<213> ORGANISM: Homo sapiens

<400> SEQUENCE: 18
ttcctcctgc tactctggct c                                           21

<210> SEQ ID NO 19
<211> LENGTH: 21
<212> TYPE: DNA
<213> ORGANISM: Homo sapiens

<400> SEQUENCE: 19
cagacccagg tcttcatttc t                                           21
```

```
<210> SEQ ID NO 20
<211> LENGTH: 24
<212> TYPE: DNA
<213> ORGANISM: Homo sapiens

<400> SEQUENCE: 20
tttcaactgc tcatcagatg gcgg                                              24

<210> SEQ ID NO 21
<211> LENGTH: 20
<212> TYPE: DNA
<213> ORGANISM: Homo sapiens

<400> SEQUENCE: 21
cctctcctcc tcaccctcct                                                   20

<210> SEQ ID NO 22
<211> LENGTH: 18
<212> TYPE: DNA
<213> ORGANISM: Homo sapiens

<400> SEQUENCE: 22
ctcctcactc agggcaca                                                     18

<210> SEQ ID NO 23
<211> LENGTH: 19
<212> TYPE: DNA
<213> ORGANISM: Homo sapiens

<400> SEQUENCE: 23
atggcctgga tccctctcc                                                    19

<210> SEQ ID NO 24
<211> LENGTH: 19
<212> TYPE: DNA
<213> ORGANISM: Homo sapiens

<400> SEQUENCE: 24
atggcctgga ccctctcc                                                     19

<210> SEQ ID NO 25
<211> LENGTH: 19
<212> TYPE: DNA
<213> ORGANISM: Homo sapiens

<400> SEQUENCE: 25
atggcctgga tcgctctcc                                                    19

<210> SEQ ID NO 26
<211> LENGTH: 19
<212> TYPE: DNA
<213> ORGANISM: Homo sapiens

<400> SEQUENCE: 26
atggcctgga ccgctctcc                                                    19

<210> SEQ ID NO 27
<211> LENGTH: 20
<212> TYPE: DNA
<213> ORGANISM: Homo sapiens

<400> SEQUENCE: 27
agctcctcag aggagggcgg                                                   20
```

<210> SEQ ID NO 28
<211> LENGTH: 20
<212> TYPE: DNA
<213> ORGANISM: Homo sapiens

<400> SEQUENCE: 28
agctcctcag aggagggtgg                                                    20

<210> SEQ ID NO 29
<211> LENGTH: 38
<212> TYPE: DNA
<213> ORGANISM: Homo sapiens

<400> SEQUENCE: 29
ctttaagaag gagatatacc atggtgcagc tggtgcag                                38

<210> SEQ ID NO 30
<211> LENGTH: 38
<212> TYPE: DNA
<213> ORGANISM: Homo sapiens

<400> SEQUENCE: 30
ctttaagaag gagatatacc atggttcagc tggtgcag                                38

<210> SEQ ID NO 31
<211> LENGTH: 41
<212> TYPE: DNA
<213> ORGANISM: Homo sapiens

<400> SEQUENCE: 31
ctttaagaag gagatatacc atgcaggtcc agcttgtgca g                            41

<210> SEQ ID NO 32
<211> LENGTH: 41
<212> TYPE: DNA
<213> ORGANISM: Homo sapiens

<400> SEQUENCE: 32
ctttaagaag gagatatacc atggaggtcc agctggtaca g                            41

<210> SEQ ID NO 33
<211> LENGTH: 41
<212> TYPE: DNA
<213> ORGANISM: Homo sapiens

<400> SEQUENCE: 33
ctttaagaag gagatatacc atgcaggtcc agctggtaca g                            41

<210> SEQ ID NO 34
<211> LENGTH: 41
<212> TYPE: DNA
<213> ORGANISM: Homo sapiens

<400> SEQUENCE: 34
ctttaagaag gagatatacc atgcaaatgc agctggtgca g                            41

<210> SEQ ID NO 35
<211> LENGTH: 41
<212> TYPE: DNA
<213> ORGANISM: Homo sapiens

<400> SEQUENCE: 35
ctttaagaag gagatatacc atgcagatgc agctggtgca g                            41

<210> SEQ ID NO 36
<211> LENGTH: 41
<212> TYPE: DNA
<213> ORGANISM: Homo sapiens

<400> SEQUENCE: 36
ctttaagaag gagatatacc atgcagatca ccttgaagga g            41

<210> SEQ ID NO 37
<211> LENGTH: 41
<212> TYPE: DNA
<213> ORGANISM: Homo sapiens

<400> SEQUENCE: 37
ctttaagaag gagatatacc atgcaggtca ccttgaagga g            41

<210> SEQ ID NO 38
<211> LENGTH: 41
<212> TYPE: DNA
<213> ORGANISM: Homo sapiens

<400> SEQUENCE: 38
ctttaagaag gagatatacc atgcaggtca ccttgaggga g            41

<210> SEQ ID NO 39
<211> LENGTH: 41
<212> TYPE: DNA
<213> ORGANISM: Homo sapiens

<400> SEQUENCE: 39
ctttaagaag gagatatacc atggaagtgc agctggtgga g            41

<210> SEQ ID NO 40
<211> LENGTH: 41
<212> TYPE: DNA
<213> ORGANISM: Homo sapiens

<400> SEQUENCE: 40
ctttaagaag gagatatacc atggaggtgc agctggtgga g            41

<210> SEQ ID NO 41
<211> LENGTH: 41
<212> TYPE: DNA
<213> ORGANISM: Homo sapiens

<400> SEQUENCE: 41
ctttaagaag gagatatacc atgcaggtgc agctggtgga g            41

<210> SEQ ID NO 42
<211> LENGTH: 41
<212> TYPE: DNA
<213> ORGANISM: Homo sapiens

<400> SEQUENCE: 42
ctttaagaag gagatatacc atggaggtgc agctgttgga g            41

<210> SEQ ID NO 43
<211> LENGTH: 41
<212> TYPE: DNA
<213> ORGANISM: Homo sapiens

<400> SEQUENCE: 43
ctttaagaag gagatatacc atgcagctgc agctgcagga g            41

<210> SEQ ID NO 44
<211> LENGTH: 41
<212> TYPE: DNA
<213> ORGANISM: Homo sapiens

<400> SEQUENCE: 44
ctttaagaag gagatatacc atgcaggtgc agctgcagga g            41

<210> SEQ ID NO 45
<211> LENGTH: 41
<212> TYPE: DNA
<213> ORGANISM: Homo sapiens

<400> SEQUENCE: 45
ctttaagaag gagatatacc atgcaggtgc agctacagca g            41

<210> SEQ ID NO 46
<211> LENGTH: 41
<212> TYPE: DNA
<213> ORGANISM: Homo sapiens

<400> SEQUENCE: 46
ctttaagaag gagatatacc atggaagtgc agctggtgca g            41

<210> SEQ ID NO 47
<211> LENGTH: 41
<212> TYPE: DNA
<213> ORGANISM: Homo sapiens

<400> SEQUENCE: 47
ctttaagaag gagatatacc atggaggtgc agctggtgca g            41

<210> SEQ ID NO 48
<211> LENGTH: 41
<212> TYPE: DNA
<213> ORGANISM: Homo sapiens

<400> SEQUENCE: 48
ctttaagaag gagatatacc atgcaggtac agctgcagca g            41

<210> SEQ ID NO 49
<211> LENGTH: 41
<212> TYPE: DNA
<213> ORGANISM: Homo sapiens

<400> SEQUENCE: 49
ctttaagaag gagatatacc atgcaggtcc agctggtgca a            41

<210> SEQ ID NO 50
<211> LENGTH: 41
<212> TYPE: DNA
<213> ORGANISM: Homo sapiens

<400> SEQUENCE: 50
ctttaagaag gagatatacc atgcaggtgc agctggtgca a            41

<210> SEQ ID NO 51
<211> LENGTH: 45
<212> TYPE: DNA
<213> ORGANISM: Homo sapiens

<400> SEQUENCE: 51

```
atcgtatggg tagctggtcc cttagaccga tgggcccttg gtgga          45
```

<210> SEQ ID NO 52
<211> LENGTH: 45
<212> TYPE: DNA
<213> ORGANISM: Homo sapiens

<400> SEQUENCE: 52

```
atcgtatggg tagctggtcc cttagacgga tgggcccttg gtgga          45
```

<210> SEQ ID NO 53
<211> LENGTH: 41
<212> TYPE: DNA
<213> ORGANISM: Homo sapiens

<400> SEQUENCE: 53

```
ctttaagaag gagatatacc atgaacatcc agatgaccca g              41
```

<210> SEQ ID NO 54
<211> LENGTH: 41
<212> TYPE: DNA
<213> ORGANISM: Homo sapiens

<400> SEQUENCE: 54

```
ctttaagaag gagatatacc atggacatcc agatgaccca g              41
```

<210> SEQ ID NO 55
<211> LENGTH: 41
<212> TYPE: DNA
<213> ORGANISM: Homo sapiens

<400> SEQUENCE: 55

```
ctttaagaag gagatatacc atggacatcc agttgaccca g              41
```

<210> SEQ ID NO 56
<211> LENGTH: 41
<212> TYPE: DNA
<213> ORGANISM: Homo sapiens

<400> SEQUENCE: 56

```
ctttaagaag gagatatacc atggccatcc agttgaccca g              41
```

<210> SEQ ID NO 57
<211> LENGTH: 41
<212> TYPE: DNA
<213> ORGANISM: Homo sapiens

<400> SEQUENCE: 57

```
ctttaagaag gagatatacc atggccatcc agatgaccca g              41
```

<210> SEQ ID NO 58
<211> LENGTH: 41
<212> TYPE: DNA
<213> ORGANISM: Homo sapiens

<400> SEQUENCE: 58

```
ctttaagaag gagatatacc atggccatcc ggatgaccca g              41
```

<210> SEQ ID NO 59
<211> LENGTH: 41
<212> TYPE: DNA
<213> ORGANISM: Homo sapiens

```
<400> SEQUENCE: 59
ctttaagaag gagatatacc atggtcatct ggatgaccca g          41

<210> SEQ ID NO 60
<211> LENGTH: 41
<212> TYPE: DNA
<213> ORGANISM: Homo sapiens

<400> SEQUENCE: 60
ctttaagaag gagatatacc atggatattg tgatgaccca g          41

<210> SEQ ID NO 61
<211> LENGTH: 41
<212> TYPE: DNA
<213> ORGANISM: Homo sapiens

<400> SEQUENCE: 61
ctttaagaag gagatatacc atggatattg tgatgactca g          41

<210> SEQ ID NO 62
<211> LENGTH: 41
<212> TYPE: DNA
<213> ORGANISM: Homo sapiens

<400> SEQUENCE: 62
ctttaagaag gagatatacc atggatgttg tgatgactca g          41

<210> SEQ ID NO 63
<211> LENGTH: 41
<212> TYPE: DNA
<213> ORGANISM: Homo sapiens

<400> SEQUENCE: 63
ctttaagaag gagatatacc atggaaattg tgttgacaca g          41

<210> SEQ ID NO 64
<211> LENGTH: 41
<212> TYPE: DNA
<213> ORGANISM: Homo sapiens

<400> SEQUENCE: 64
ctttaagaag gagatatacc atggaaattg tgttgacgca g          41

<210> SEQ ID NO 65
<211> LENGTH: 41
<212> TYPE: DNA
<213> ORGANISM: Homo sapiens

<400> SEQUENCE: 65
ctttaagaag gagatatacc atggaaatag tgatgacgca g          41

<210> SEQ ID NO 66
<211> LENGTH: 41
<212> TYPE: DNA
<213> ORGANISM: Homo sapiens

<400> SEQUENCE: 66
ctttaagaag gagatatacc atggaaattg taatgacaca g          41

<210> SEQ ID NO 67
<211> LENGTH: 41
<212> TYPE: DNA
<213> ORGANISM: Homo sapiens
```

```
<400> SEQUENCE: 67
ctttaagaag gagatatacc atggacatcg tgatgaccca g          41

<210> SEQ ID NO 68
<211> LENGTH: 41
<212> TYPE: DNA
<213> ORGANISM: Homo sapiens

<400> SEQUENCE: 68
ctttaagaag gagatatacc atggaaacga cactcacgca g          41

<210> SEQ ID NO 69
<211> LENGTH: 41
<212> TYPE: DNA
<213> ORGANISM: Homo sapiens

<400> SEQUENCE: 69
ctttaagaag gagatatacc atggaaattg tgctcactca g          41

<210> SEQ ID NO 70
<211> LENGTH: 41
<212> TYPE: DNA
<213> ORGANISM: Homo sapiens

<400> SEQUENCE: 70
ctttaagaag gagatatacc atggatgttg tgatgacaca g          41

<210> SEQ ID NO 71
<211> LENGTH: 44
<212> TYPE: DNA
<213> ORGANISM: Homo sapiens

<400> SEQUENCE: 71
atcgtatggg tagctggtcc cttaaagatg aagacagatg gtgc       44

<210> SEQ ID NO 72
<211> LENGTH: 41
<212> TYPE: DNA
<213> ORGANISM: Homo sapiens

<400> SEQUENCE: 72
ctttaagaag gagatatacc atgcagtctg tgctgactca g          41

<210> SEQ ID NO 73
<211> LENGTH: 41
<212> TYPE: DNA
<213> ORGANISM: Homo sapiens

<400> SEQUENCE: 73
ctttaagaag gagatatacc atgcagtctg tgctgacgca g          41

<210> SEQ ID NO 74
<211> LENGTH: 41
<212> TYPE: DNA
<213> ORGANISM: Homo sapiens

<400> SEQUENCE: 74
ctttaagaag gagatatacc atgcagtctg tgttgacgca g          41

<210> SEQ ID NO 75
<211> LENGTH: 41
<212> TYPE: DNA
```

-continued

<213> ORGANISM: Homo sapiens

<400> SEQUENCE: 75
ctttaagaag gagatatacc atgcagtctg tcgtgacgca g    41

<210> SEQ ID NO 76
<211> LENGTH: 41
<212> TYPE: DNA
<213> ORGANISM: Homo sapiens

<400> SEQUENCE: 76
ctttaagaag gagatatacc atgcagtctg ccctgactca g    41

<210> SEQ ID NO 77
<211> LENGTH: 41
<212> TYPE: DNA
<213> ORGANISM: Homo sapiens

<400> SEQUENCE: 77
ctttaagaag gagatatacc atgtcctatg agctgactca g    41

<210> SEQ ID NO 78
<211> LENGTH: 41
<212> TYPE: DNA
<213> ORGANISM: Homo sapiens

<400> SEQUENCE: 78
ctttaagaag gagatatacc atgtcctatg tgctgactca g    41

<210> SEQ ID NO 79
<211> LENGTH: 41
<212> TYPE: DNA
<213> ORGANISM: Homo sapiens

<400> SEQUENCE: 79
ctttaagaag gagatatacc atgtcctatg agctgacaca g    41

<210> SEQ ID NO 80
<211> LENGTH: 41
<212> TYPE: DNA
<213> ORGANISM: Homo sapiens

<400> SEQUENCE: 80
ctttaagaag gagatatacc atgtcttctg agctgactca g    41

<210> SEQ ID NO 81
<211> LENGTH: 41
<212> TYPE: DNA
<213> ORGANISM: Homo sapiens

<400> SEQUENCE: 81
ctttaagaag gagatatacc atgtcctatg agctgatgca g    41

<210> SEQ ID NO 82
<211> LENGTH: 41
<212> TYPE: DNA
<213> ORGANISM: Homo sapiens

<400> SEQUENCE: 82
ctttaagaag gagatatacc atgcagcctg tgctgactca a    41

<210> SEQ ID NO 83
<211> LENGTH: 41

```
<212> TYPE: DNA
<213> ORGANISM: Homo sapiens

<400> SEQUENCE: 83
ctttaagaag gagatatacc atgcagcttg tgctgactca a         41

<210> SEQ ID NO 84
<211> LENGTH: 41
<212> TYPE: DNA
<213> ORGANISM: Homo sapiens

<400> SEQUENCE: 84
ctttaagaag gagatatacc atgcagcctg tgctgactca g         41

<210> SEQ ID NO 85
<211> LENGTH: 41
<212> TYPE: DNA
<213> ORGANISM: Homo sapiens

<400> SEQUENCE: 85
ctttaagaag gagatatacc atgcaggctg tgctgactca g         41

<210> SEQ ID NO 86
<211> LENGTH: 41
<212> TYPE: DNA
<213> ORGANISM: Homo sapiens

<400> SEQUENCE: 86
ctttaagaag gagatatacc atgaattta tgctgactca g          41

<210> SEQ ID NO 87
<211> LENGTH: 41
<212> TYPE: DNA
<213> ORGANISM: Homo sapiens

<400> SEQUENCE: 87
ctttaagaag gagatatacc atgcagactg tggtgactca g         41

<210> SEQ ID NO 88
<211> LENGTH: 41
<212> TYPE: DNA
<213> ORGANISM: Homo sapiens

<400> SEQUENCE: 88
ctttaagaag gagatatacc atgcaggctg tggtgactca g         41

<210> SEQ ID NO 89
<211> LENGTH: 41
<212> TYPE: DNA
<213> ORGANISM: Homo sapiens

<400> SEQUENCE: 89
ctttaagaag gagatatacc atgcagactg tggtgaccca g         41

<210> SEQ ID NO 90
<211> LENGTH: 41
<212> TYPE: DNA
<213> ORGANISM: Homo sapiens

<400> SEQUENCE: 90
ctttaagaag gagatatacc atgcagcctg tgctgactca g         41

<210> SEQ ID NO 91
```

```
<210> SEQ ID NO 91
<211> LENGTH: 41
<212> TYPE: DNA
<213> ORGANISM: Homo sapiens

<400> SEQUENCE: 91
ctttaagaag gagatatacc atgctgcctg tgctgactca g          41

<210> SEQ ID NO 92
<211> LENGTH: 41
<212> TYPE: DNA
<213> ORGANISM: Homo sapiens

<400> SEQUENCE: 92
ctttaagaag gagatatacc atgcaggcag ggctgactca g          41

<210> SEQ ID NO 93
<211> LENGTH: 40
<212> TYPE: DNA
<213> ORGANISM: Homo sapiens

<400> SEQUENCE: 93
atcgtatggg tagctggtcc cttagggaac agagtgaccg            40

<210> SEQ ID NO 94
<211> LENGTH: 43
<212> TYPE: DNA
<213> ORGANISM: Homo sapiens

<400> SEQUENCE: 94
ctttaagaag gagatatacc atgcaggtgc agctggtgca gtc        43

<210> SEQ ID NO 95
<211> LENGTH: 46
<212> TYPE: DNA
<213> ORGANISM: Homo sapiens

<400> SEQUENCE: 95
ctttaagaag gagatatacc atgcaggtca acttaaggga gtctgg     46

<210> SEQ ID NO 96
<211> LENGTH: 42
<212> TYPE: DNA
<213> ORGANISM: Homo sapiens

<400> SEQUENCE: 96
ctttaagaag gagatatacc atgaggtgca gctgctgcag tc         42

<210> SEQ ID NO 97
<211> LENGTH: 42
<212> TYPE: DNA
<213> ORGANISM: Homo sapiens

<400> SEQUENCE: 97
ctttaagaag gagatatacc atgaggtgca gctgctggag tc         42

<210> SEQ ID NO 98
<211> LENGTH: 42
<212> TYPE: DNA
<213> ORGANISM: Homo sapiens

<400> SEQUENCE: 98
ctttaagaag gagatatacc atgaggtgca gctggtgcag tc         42
```

<210> SEQ ID NO 99
<211> LENGTH: 42
<212> TYPE: DNA
<213> ORGANISM: Homo sapiens

<400> SEQUENCE: 99
ctttaagaag gagatatacc atgaggtgca gctggtggag tc         42

<210> SEQ ID NO 100
<211> LENGTH: 43
<212> TYPE: DNA
<213> ORGANISM: Homo sapiens

<400> SEQUENCE: 100
ctttaagaag gagatatacc atgcaggtac agctgcagca gtc        43

<210> SEQ ID NO 101
<211> LENGTH: 43
<212> TYPE: DNA
<213> ORGANISM: Homo sapiens

<400> SEQUENCE: 101
ctttaagaag gagatatacc atgcaggtac agctgcagga gtc        43

<210> SEQ ID NO 102
<211> LENGTH: 43
<212> TYPE: DNA
<213> ORGANISM: Homo sapiens

<400> SEQUENCE: 102
ctttaagaag gagatatacc atgcaggtgc agctgcagca gtc        43

<210> SEQ ID NO 103
<211> LENGTH: 43
<212> TYPE: DNA
<213> ORGANISM: Homo sapiens

<400> SEQUENCE: 103
ctttaagaag gagatatacc atgcaggtgc agctgcagga gtc        43

<210> SEQ ID NO 104
<211> LENGTH: 67
<212> TYPE: DNA
<213> ORGANISM: Homo sapiens

<400> SEQUENCE: 104
atcgtatggg tagctggtcc cttagtggtg gtggtggtgg tgaactctct tgtccacctt    60
ggtgttg                                                              67

<210> SEQ ID NO 105
<211> LENGTH: 67
<212> TYPE: DNA
<213> ORGANISM: Homo sapiens

<400> SEQUENCE: 105
atcgtatggg tagctggtcc cttagtggtg gtggtggtgg tgaactgtct tgtccacctt    60
ggtgttg                                                              67

<210> SEQ ID NO 106
<211> LENGTH: 67
<212> TYPE: DNA
<213> ORGANISM: Homo sapiens

```
<400> SEQUENCE: 106
atcgtatggg tagctggtcc cttagtggtg gtggtggtgg tgaactttct tgtccacctt    60
ggtgttg                                                              67

<210> SEQ ID NO 107
<211> LENGTH: 44
<212> TYPE: DNA
<213> ORGANISM: Homo sapiens

<400> SEQUENCE: 107
ctttaagaag gagatatacc atggacatcc agatgaccca gtct                    44

<210> SEQ ID NO 108
<211> LENGTH: 44
<212> TYPE: DNA
<213> ORGANISM: Homo sapiens

<400> SEQUENCE: 108
ctttaagaag gagatatacc atggacatcg agatgaccca gtct                    44

<210> SEQ ID NO 109
<211> LENGTH: 44
<212> TYPE: DNA
<213> ORGANISM: Homo sapiens

<400> SEQUENCE: 109
ctttaagaag gagatatacc atggacatcg agatgaccca gtct                    44

<210> SEQ ID NO 110
<211> LENGTH: 44
<212> TYPE: DNA
<213> ORGANISM: Homo sapiens

<400> SEQUENCE: 110
ctttaagaag gagatatacc atggacatcg tgatgaccca gtct                    44

<210> SEQ ID NO 111
<211> LENGTH: 46
<212> TYPE: DNA
<213> ORGANISM: Homo sapiens

<400> SEQUENCE: 111
ctttaagaag gagatatacc atggatattg tgatgactca gtctcc                  46

<210> SEQ ID NO 112
<211> LENGTH: 46
<212> TYPE: DNA
<213> ORGANISM: Homo sapiens

<400> SEQUENCE: 112
ctttaagaag gagatatacc atggatattg tgctgactca gtctcc                  46

<210> SEQ ID NO 113
<211> LENGTH: 46
<212> TYPE: DNA
<213> ORGANISM: Homo sapiens

<400> SEQUENCE: 113
ctttaagaag gagatatacc atggaaattg tgttgacgca gtctcc                  46

<210> SEQ ID NO 114
<211> LENGTH: 45
```

<212> TYPE: DNA
<213> ORGANISM: Homo sapiens

<400> SEQUENCE: 114
ctttaagaag gagatatacc atggaaacga cactcacgca gtctc        45

<210> SEQ ID NO 115
<211> LENGTH: 46
<212> TYPE: DNA
<213> ORGANISM: Homo sapiens

<400> SEQUENCE: 115
atcgtatggg tagctggtcc cttaacactc tcccctgttg aagctc        46

<210> SEQ ID NO 116
<211> LENGTH: 43
<212> TYPE: DNA
<213> ORGANISM: Homo sapiens

<400> SEQUENCE: 116
ctttaagaag gagatatacc atgcagtctg tgctgactca gcc        43

<210> SEQ ID NO 117
<211> LENGTH: 43
<212> TYPE: DNA
<213> ORGANISM: Homo sapiens

<400> SEQUENCE: 117
ctttaagaag gagatatacc atgcagtctg ccctgactca gcc        43

<210> SEQ ID NO 118
<211> LENGTH: 43
<212> TYPE: DNA
<213> ORGANISM: Homo sapiens

<400> SEQUENCE: 118
ctttaagaag gagatatacc atgtcctatg agctgacaca gcc        43

<210> SEQ ID NO 119
<211> LENGTH: 43
<212> TYPE: DNA
<213> ORGANISM: Homo sapiens

<400> SEQUENCE: 119
ctttaagaag gagatatacc atgtcctatg agctgactca gcc        43

<210> SEQ ID NO 120
<211> LENGTH: 46
<212> TYPE: DNA
<213> ORGANISM: Homo sapiens

<400> SEQUENCE: 120
atcgtatggg tagctggtcc cttatgaaca ttccgcaggg gcaact        46

<210> SEQ ID NO 121
<211> LENGTH: 46
<212> TYPE: DNA
<213> ORGANISM: Homo sapiens

<400> SEQUENCE: 121
atcgtatggg tagctggtcc cttatgaaca ttctgcaggg gcaact        46

<210> SEQ ID NO 122

```
<211> LENGTH: 46
<212> TYPE: DNA
<213> ORGANISM: Homo sapiens

<400> SEQUENCE: 122
atcgtatggg tagctggtcc cttatgaaca ttccgtaggg gcaact          46

<210> SEQ ID NO 123
<211> LENGTH: 46
<212> TYPE: DNA
<213> ORGANISM: Homo sapiens

<400> SEQUENCE: 123
atcgtatggg tagctggtcc cttatgaaca ttccgcaggg gctact          46

<210> SEQ ID NO 124
<211> LENGTH: 46
<212> TYPE: DNA
<213> ORGANISM: Homo sapiens

<400> SEQUENCE: 124
atcgtatggg tagctggtcc cttatgaaca ttctgtaggg gcaact          46

<210> SEQ ID NO 125
<211> LENGTH: 46
<212> TYPE: DNA
<213> ORGANISM: Homo sapiens

<400> SEQUENCE: 125
atcgtatggg tagctggtcc cttatgaaca ttctgtaggg gctact          46

<210> SEQ ID NO 126
<211> LENGTH: 23
<212> TYPE: DNA
<213> ORGANISM: Homo sapiens

<400> SEQUENCE: 126
ctttaagaag gagatatacc atg                                   23

<210> SEQ ID NO 127
<211> LENGTH: 24
<212> TYPE: DNA
<213> ORGANISM: Homo sapiens

<400> SEQUENCE: 127
atcgtatggg tagctggtcc ctta                                  24

<210> SEQ ID NO 128
<211> LENGTH: 41
<212> TYPE: DNA
<213> ORGANISM: Homo sapiens

<400> SEQUENCE: 128
ctttaagaag gagatatacc atgcaggtkc agctggtgca g               41

<210> SEQ ID NO 129
<211> LENGTH: 41
<212> TYPE: DNA
<213> ORGANISM: Homo sapiens

<400> SEQUENCE: 129
ctttaagaag gagatatacc atgcaggtcc agcttgtgca g               41
```

<210> SEQ ID NO 130
<211> LENGTH: 41
<212> TYPE: DNA
<213> ORGANISM: Homo sapiens

<400> SEQUENCE: 130
ctttaagaag gagatatacc atgsaggtcc agctggtaca g         41

<210> SEQ ID NO 131
<211> LENGTH: 41
<212> TYPE: DNA
<213> ORGANISM: Homo sapiens

<400> SEQUENCE: 131
ctttaagaag gagatatacc atgcaratgc agctggtgca g         41

<210> SEQ ID NO 132
<211> LENGTH: 41
<212> TYPE: DNA
<213> ORGANISM: Homo sapiens

<400> SEQUENCE: 132
ctttaagaag gagatatacc atgcagatca ccttgaagga g         41

<210> SEQ ID NO 133
<211> LENGTH: 41
<212> TYPE: DNA
<213> ORGANISM: Homo sapiens

<400> SEQUENCE: 133
ctttaagaag gagatatacc atgcaggtca ccttgargga g         41

<210> SEQ ID NO 134
<211> LENGTH: 41
<212> TYPE: DNA
<213> ORGANISM: Homo sapiens

<400> SEQUENCE: 134
ctttaagaag gagatatacc atggargtgc agctggtgga g         41

<210> SEQ ID NO 135
<211> LENGTH: 41
<212> TYPE: DNA
<213> ORGANISM: Homo sapiens

<400> SEQUENCE: 135
ctttaagaag gagatatacc atgcaggtgc agctggtgga g         41

<210> SEQ ID NO 136
<211> LENGTH: 41
<212> TYPE: DNA
<213> ORGANISM: Homo sapiens

<400> SEQUENCE: 136
ctttaagaag gagatatacc atggaggtgc agctgttgga g         41

<210> SEQ ID NO 137
<211> LENGTH: 41
<212> TYPE: DNA
<213> ORGANISM: Homo sapiens

<400> SEQUENCE: 137
ctttaagaag gagatatacc atgcagstgc agctgcagga g         41

<210> SEQ ID NO 138
<211> LENGTH: 41
<212> TYPE: DNA
<213> ORGANISM: Homo sapiens

<400> SEQUENCE: 138
ctttaagaag gagatatacc atgcaggtgc agctacagca g    41

<210> SEQ ID NO 139
<211> LENGTH: 41
<212> TYPE: DNA
<213> ORGANISM: Homo sapiens

<400> SEQUENCE: 139
ctttaagaag gagatatacc atggargtgc agctggtgca g    41

<210> SEQ ID NO 140
<211> LENGTH: 41
<212> TYPE: DNA
<213> ORGANISM: Homo sapiens

<400> SEQUENCE: 140
ctttaagaag gagatatacc atgcaggtac agctgcagca g    41

<210> SEQ ID NO 141
<211> LENGTH: 41
<212> TYPE: DNA
<213> ORGANISM: Homo sapiens

<400> SEQUENCE: 141
ctttaagaag gagatatacc atgcaggtac agctggtgca a    41

<210> SEQ ID NO 142
<211> LENGTH: 48
<212> TYPE: DNA
<213> ORGANISM: Artificial
<220> FEATURE:
<223> OTHER INFORMATION: VH-lfp

<400> SEQUENCE: 142
ctttaagaag gagatatacc atgaactbtc ttgtccacct tggtgttg    48

<210> SEQ ID NO 143
<211> LENGTH: 49
<212> TYPE: DNA
<213> ORGANISM: Artificial
<220> FEATURE:
<223> OTHER INFORMATION: VH-rfp

<400> SEQUENCE: 143
atcgtatggg tagctggtcc cttaaactbt cttgtccacc ttggtgttg    49

<210> SEQ ID NO 144
<211> LENGTH: 45
<212> TYPE: DNA
<213> ORGANISM: Artificial
<220> FEATURE:
<223> OTHER INFORMATION: VL(k)-lfp

<400> SEQUENCE: 144
ctttaagaag gagatatacc atgacactct cccctgttga agctc    45

<210> SEQ ID NO 145
<211> LENGTH: 46

```
<212> TYPE: DNA
<213> ORGANISM: Artificial
<220> FEATURE:
<223> OTHER INFORMATION: VL(k)-rfp

<400> SEQUENCE: 145
atcgtatggg tagctggtcc cttaacactc tcccctgttg aagctc                    46
```